(12) United States Patent
Wagner et al.

(10) Patent No.: US 9,018,370 B2
(45) Date of Patent: Apr. 28, 2015

(54) DERIVATIVES OF URIDINE PHOSPHATE AND THEIR USES IN PROTEIN BINDING ASSAYS

(75) Inventors: Gerd Wagner, London (GB); Thomas Pesnot, Coulsdon (GB)

(73) Assignee: King's College London of Strand, London (GB)

( * ) Notice: Subject to any disclaimer, the term of this patent is extended or adjusted under 35 U.S.C. 154(b) by 284 days.

(21) Appl. No.: 13/504,997

(22) PCT Filed: Nov. 1, 2010

(86) PCT No.: PCT/GB2010/051830
§ 371 (c)(1),
(2), (4) Date: Apr. 30, 2012

(87) PCT Pub. No.: WO2011/051733
PCT Pub. Date: May 5, 2011

(65) Prior Publication Data
US 2012/0219963 A1 Aug. 30, 2012

(30) Foreign Application Priority Data
Oct. 30, 2009 (GB) .................................. 0919070.3

(51) Int. Cl.
*C07H 19/10* (2006.01)
*C12M 1/34* (2006.01)
*C12N 9/12* (2006.01)
*G01N 33/573* (2006.01)

(52) U.S. Cl.
CPC ...................................... *C07H 19/10* (2013.01)

(58) Field of Classification Search
CPC ........................................................ C07H 19/10
USPC ...................................... 536/26.8; 435/288.4
See application file for complete search history.

(56) References Cited

U.S. PATENT DOCUMENTS 5,985,849 A * 11/1999 Kindon et al. .................. 514/51

OTHER PUBLICATIONS

Cahova et al, Angew. Chemie, Int. Ed, 2008, 47, 2059-62.*
By Cahova et al, Angew. Chem. Int. Ed. 2008, 47, 2059-62.*
Chang et al , J. Med. Chem. 1988, 31(9), 1141-47.*
Srivatsan et al, Chemistry-An Asian Journal, Apr. 6, 2009, 4, 419-27.*
Pesnot et al, Organic and Biomolecular Chemistry, 2008, 6, 2884-91.*
International Search Report dated Jul. 11, 2011 and Written Opinion dated Apr. 30, 2012 in related application PCT/GB2010/051830, 20 pages.
Cahova, H. et al., Aminophenyl- and Nitrophenyl-Labeled Nucleoside Triphosphates: Synthesis, Enzymatic Incorporation, and Electrochemical Detection, Angewandte Chemie International Edition, vol. 47, No. 11, pp. 2059-2062, Feb. 7, 2008.
Chang, et al., Linear free energy relationship studies of enzyme active site bindiing: thymidylate synthase, J. Med. Chem., vol. 31, No. 6, pp. 1141-1147, Jun. 1988.
Laman, et al., 5-Quinone derivatives of 2'-deoxyuridine 5'-phosphaste;inhibition and inactivation of thymidylate synthase, antitumor cell, and antiviral studies, J. Med. Chem., vol. 30, No. 2, pp. 409-419, Feb. 1987.
Presnot, T. et al., Novel derivatives of UDP-glucose: concise synthesis and fluorescent properties, Org. Biomol. Chem., vol. 6, No. 16, pp. 2884-2891, Jun. 18, 2008.
Presnot et al., A Novel Fluorescent Probe for Retaining Galactosyltranferases, Chembiochem., vol. 11, No. 10, pp. 1392-1398, Jun. 8, 2010.
Presnot, et al., Structural and mechanistic basis for a new mode of glycosyltransferase inhibition, Nature Chemical Biology, vol. 6, pp. 321-323, Apr. 4, 2010.
International Preliminary Report on Patentability in related application PCT/GB2010/051830 mailed May 10, 2012, 18 pages.
Alfaro et al: ABO(H) Blood Group A and B Glycosyltransferases Recognize Substrate via Specific Conformational Changes; J. Biol. Chem., vol. 283, pp. 10097-10108 (2008).
Berg et al: The glycosyltransferases of *Mycobacterium tuberculosis*-roles in the synthesis of arabinogalactan, lipoarabinomannan and other glycoconjugates; Glycobiology; vol. 17, pp. 35R-56R (2007).
Breton et al: Structures and mechanisms of glycosyltransferases; Glycobiology; vol. 16, pp. 29R-37R (2006).
Deng et al: A pH-sehnsitive assay for galactosyltransferase; Anal. Biochem; vol. 330, pp. 219-226 (2004).
Dube et al: Glycans in cancer and inflammation: potential for therapeutics and diagnostics; Nat. Rev. Drug Discov. vol. 4, pp. 477-488 (2005).
Endo et al: Cloning and expression of Beta1,-4-galactosyltransferase gene from Heliocobacter pylori; Glycobiology; vol. 10, pp. 809-813 (2000).
Gosselin et al: A Continuous Spectrophotometric Assay for Glycosyltransferases; Anal. Biochem; vol. 220, pp. 92-97 (1994).
Gross et al: Discovery of O-GlcNAc transferase inhibitors; J. Am. Chem. Soc., vol. 127, pp. 14588-14589 (2005).
Helm et al: Identification of Active-site Inhibitors of MurG Using a Generalizable, High-Throughput Glycosyltransferase Screen; J. Am. Chem. Soc; vol. 125, pp. 11168-11169 (2003).
Keshvara et al: Immunological-based assay methods for glycosyltransferase enzymes; Glycobiology, vol. 3, pp. 416-418 (1993).
Kochanowski et al: Intracellular nucleotide an nucleotide sugar contents of cultured CHO cells determined by a fast, sensitive and high-resolution ion-pair RP-HPLC; Anal. Biochem, vol. 348, pp. 243-251 (2006).

(Continued)

Primary Examiner — Ganapathy Krishnan
(74) Attorney, Agent, or Firm — James H. Velema, Esq.; Lathrop & Gage LLP

(57) ABSTRACT

The present invention relates to compounds and their use in competitive protein binding assays, for example for use with glycosyl transferase and/or glycoprocessing proteins. The present application also provides kits and apparatuses for use in the assays. In particular, the present invention provides a compound of the formula (I): wherein n is 1, 2 or 3; $R_1$ is selected from —OH, —OPO$_3$H, —OR$_4$, —NHR$_4$, R$_6$; $R_2$ and $R_3$ are each independently selected from —H, —OH, optionally substituted —O-alkyl and —O-alkanoyl; $R_4$ is selected from an optionally substituted mono or polysaccharide, -alkyl, -alkenyl, -alkynyl, and L-Z, where L is a linking agent and Z is a binding agent; $R_6$ is an optionally substituted hydrocarbon group; A is either (i) a substituted heteroaryl group, the substituent on the heteroaryl group having a double bond conjugated to the heteroaryl group, or (ii) a substituted aryl group, the substituent on the aryl group having a double bond conjugated to the aryl group.

32 Claims, 15 Drawing Sheets

(56) References Cited

OTHER PUBLICATIONS

Lairson et al: Glycosyltransferases: structures, functions and mechanisms; Ann.. Rev. Biochem; vol. 77, pp. 521-555 (2008).
Marth et al: Mammalian glycosylation in immunity; Nat. Rev. Immunol.; vol. 8, pp. 874-887 (2008).
Mizyed et al: UDP-N-acetylmuramic acid (UDP-MurNAc) is a potent inhibitor of MurA (enolpyruvyl-UDP-GlcNAc synthase); Biochemistry; vol. 44, pp. 4011-4017 (2005).
Nagahori et al: Glycosyltransferase Microarray Displayed on the Glycolipid LB Membrane; Adv. Synth. Catal.; vol. 345, pp. 729-734 (2003).
Namdjou et al: A beta-1,4-galactosyltransferase from Heliobacter pylori is an efficient and versatile biocatalyst displaying a novel activity for thioglycoside synthesis; Chem. Bio. Chem; vol. 9, pp. 1632-1640 (2008).
Palcic et al: Assays for Glycosyltransferases; Trends Glycosci. Glycotechnol.; vol. 13, pp. 361-370 (2001).
Palcic et al: Synthetic Neoglycoconjugates in Glycosyltransferase Assay and Purification; Methods Enzymol., vol. 247, pp. 215-227 (1994).
Park et al: Carbohydrate Microarrays for Assaying Galactosyltransferase Activity; Org. Lett.; vol. 9, pp. 1675-1678 (2007).
Persson et al: Structural Effects of Naturally Occurring Human Blood Group B Galactosyltransferase Mutations Adjacent to the DXD Motif; J. Biol. Chem.; vol. 282, pp. 9564-9570 (2007).
Poolman et al: Carbohydrate utilization in *Streptococcus thermophilus*: characterization of the genes for aldose 1-epimerase (mutarotase) and UDPglucose 4-epimerase; J. Bacteriol.; vol. 172(7), pp. 4037-4047 (1990).
Qian et al: Glycosyltransferase Inhibitors; Carbohydrates in Chemistry & Biology; B. Ernest, G. Hart, P. Sinay (eds) pp. 293-328 (2000).
Rexach et al: Chemical approaches to understanding O-GlcNAc glycosylation in the brain; Nat. Chem. Biol.; vol. 4, pp. 97-106 (2008).
Rich et al: Glycosyltransferase-Catalyzed Synthesis of Thiooligosaccharides; Angew. Chem. Int. Ed., 43, 613-615 (2004).
Schuman et al: Glycosyltransferase structure and function; Top. Curr. Chem.; vol. 272, pp. 217-257 (2008).
Sinkeldam et al: Fluorescent Analogs of Biomolecular Building Blocks: Design, Properties and Applications; Chem Rev.; vol. 110, pp. 2579-2619 (2010).
Sujino et al: Enzymatic Synthesis of Oligosaccharide Analogues: Evaluation of UDP-Gal Analogues as Donors for Three Retaining α-Galactosyltransferases; J. Am. Chem. Soc,; vol. 122, pp. 1261-1269 (2000).
Taniguchi et al: Glycosyltransferase Assays Using Pyridylaminated Acceptors: N-Acetylglucosaminyltransferase III, IV, and V; J. Methods Enzymol; vol. 179, pp. 397 (1989).
Verdon et al: An Enzyme-Linked Immunosorbent Assay for Lactose Synthase (Galactosyltransferase) in Serum and Its Application as a Tumor Marker in Ovarian Carcinoma; Clin. Chem.; vol. 29, pp. 1928-1923 (1983).
Von Ahsen et al: A miniaturized high-throughput screening assay for fucosyltransferase VII; Anal. Biochem.; vol. 372, pp. 96-105 (2008).
Weadge et. al. "Chemistry of glycosyltransferases" Wiley Encyclopedia of Chemical Biology, (DOI 10.1002/9780470048672. wecb213) pp. 1-13 (2008).
Wongkongkatep et al: Label-Free, Real-Time Glycosyltransferase Assay Based on a Fluorescent Artificial Chemosensor; Angewwandte Chem; vol. 118, pp. 665-668 (2006).

\* cited by examiner

Scheme 1

(i) morpholine, dipyridyl disulfide, PPh$_3$, DMSO, 1h, rt; (ii) Gal-1-P, tetrazole, DMF, rt, 5h; (iii) R-B(OH)$_2$, Na$_2$Cl$_4$Pd, TPPTS, Cs$_2$CO$_3$, H$_2$O, 50°C, 1h. For substituents R see Table 1.

a: 2M HNO$_3$, CH$_2$Cl$_2$, I$_2$, 80 °C, 12h; b: R-B(OH)$_2$, Cs$_2$CO$_3$, TPPTS, Na$_2$Cl$_4$Pd, H$_2$O, 60 °C, 1h; c: morpholine, PPh$_3$, Dipyridine disulfide, DMSO, rt, 1h. d: K$_2$P$_2$O$_7$ (R' = pyrophosphate) or Na$_3$PO$_4$ (R' = phosphate), tetrazole, MeCN, rt, 2h Scheme 1

Conditions: (i) Ac$_2$O, pyridine, rt, overnight; (ii) HBr (33% in AcOH), 0 °C, 2h; (iii) diethyl vinylphosphonate, n-Bu$_3$SnCl, NaCNBH$_3$, reflux, radical initiator, solvent, 1 to 4 days; (iv) Me$_3$SiBr, pyridine, CH$_3$CN, 0 °C, 3h; (v) H$_2$O/MeOH/Et$_3$N, rt, 16h.

Scheme 2

Conditions: (i) morpholine, dipyridyldisulfide, Ph$_3$P, DMSO, rt, 2h; (ii) Gal-1-phosphonate; tetrazole (5 equiv.), DMF, rt, 4 days; (iii) 5-formylthien-2-ylboronic acid, Cs$_2$CO$_3$, TPPTS, Na$_2$Cl$_4$Pd, H$_2$O, 17h/40 °C or 2h/55°C.

DERIVATIVES OF URIDINE PHOSPHATE AND THEIR USES IN PROTEIN BINDING ASSAYS

RELATED APPLICATIONS

This application is a 35 U.S.C. §371 filing of International Application No. PCT/GB2010/051830 filed Nov. 1, 2010, which claims priority to United Kingdom Patent Application No. 0919070.3 filed Oct. 30, 2009. The entire contents of each of the above documents are incorporated herein by reference.

FIELD OF THE INVENTION

The present invention relates to compounds and their use in competitive protein binding assays, for example for use with glycosyl transferase and/or glycoprocessing proteins. The present application also provides kits and apparatuses for use in the assays.

BACKGROUND TO THE INVENTION

In all domains of life, the biosynthesis of complex glyco-conjugates requires the concerted action of a multitude of glycosyltransferases (GTs), enzymes that catalyse the transfer of a mono- or oligosaccharide from a glycosyl donor, e.g. a sugar-nucleotide, to a suitable acceptor, e.g. a glycan, peptide or lipid. These functions are further described in Weadge, J. T. & Palcic, M. M. Chemistry of glycosyltransferases. *Wiley Encyclopedia of Chemical Biology*. DOI 10.1002/9780470048672.wecb213, 1-13 (2008); Lairson, L. L., Henrissat, B., Davies, G. J. & Withers, S. G. Glycosyltransferases: structures, functions and mechanisms. *Annu. Rev. Biochem.* 77, 521-555 (2008); Schuman, B., Alfaro, J. A. & Evans, S. V. Glycosyltransferase structure and function. *Top. Curr. Chem.* 272, 217-257 (2008); Breton, C., Snajdrova, L., Jeanneau, C., Koca, J. & Imberty, A. Structures and mechanisms of glycosyltransferases. *Glycobiology* 16, 29R-37R (2006).

GTs play a key role in many fundamental biological processes underpinning human health and disease, such as cell signalling, cellular adhesion, carcinogenesis, and cell wall biosynthesis in humanpathogens. This is further described in Marth, J. D. & Grewal, P. K. Mammalian glycosylation in immunity. *Nat. Rev. Immunol.* 8, 874-887 (2008); Rexach, J. E., Clark, P. M. & Hsieh-Wilson, L. C. Chemical approaches to understanding O-GlcNAc glycosylation in the brain. *Nat. Chem. Biol.* 4, 97-106 (2008); Dube, D. H. & Bertozzi, C. R. Glycans in cancer and inflammation: potential for therapeutics and diagnostics. *Nat. Rev. Drug. Discov.* 4, 477-488 (2005); Berg, S., Kaur, D., Jackson, M. & Brennan, P. J. The glycosyltransferases of *Mycobacterium tuberculosis*—roles in the synthesis of arabinogalactan, lipoarabinomannan, and other glycoconjugates. *Glycobiology* 17, 35R-56R (2007).

The development of small molecular glycosyltransferase inhibitors is therefore of considerable scientific interest in chemical glycobiology and drug discovery. Thus, GT inhibitors are sought after as molecular tools for the interrogation of glycosylation pathways, for mechanistic studies on carbohydrate-active enzymes, and as lead compounds in several important therapeutic areas, including infectious diseases, inflammation and cancer. This is further described in Qian, X. & Palcic, M. M. Glycosyltransferase Inhibitors. In: B. Ernst, G. Hart, P. Sinaÿ (Eds.) *Carbohydrates in Chemistry & Biology*, p 293-328 (Wiley-VCH, Weinheim, 2000).

A number of methods have been developed to study glycosyltransferases (GTs), as isolated enzymes and in living organisms. These methods allow the monitoring of GT activity during and after enzyme purification and can be used for studies of enzyme mechanisms, inhibition measurements, high throughput screening (HTS) and applications in biocatalysis. Enzymatic bioassays can be designed as either a functional or a binding assay. Functional assays provide information, qualitatively and quantitatively, about the progress of an enzymatically catalysed reaction and about the influence of a chemical of interest on said enzymatic reaction. Thus, the biological activity of a molecule towards an enzyme can be determined, e.g. whether said molecule behaves as an inhibitor or a substrate. Functional bioassays for GTs are most commonly based on monitoring either the depletion of the substrates (i.e. sugar-nucleotide and acceptor) or the formation of the products (i.e. nucleoside diphosphate or glycosylated acceptor).

Ideally, GT functional assays are carried out in real time with saturated substrate concentrations. However, this is often difficult to achieve practically because of the elevated cost and limited availability of many GT substrates. Binding bioassays, on the other hand, do not necessarily require both enzymatic substrates since they are exclusively designed to quantify the binding affinity of a molecule for an enzyme, and do not rely on an enzymatic reaction. Since they can be developed as HTS assays, binding affinity bioassays are especially useful in medicinal chemistry projects to determine the binding activity of small molecular inhibitors.

Due to the complexities of assaying GTs, an extensive range of methods have been employed for the development of both functional and binding assays (Palcic, M. M.; Sujino, K. *Trends Glycosci. Glycotechnol.* 2001, 13, 361.) Thus, methods based on different principles of detection such as radiochemistry, chromatography, immunology and spectrophotometry have been designed. Functional assays include chromatographic, spectrophotometric and radiochemical assays. The use of chromatographic methods in functional assays is further described in Taniguchi, N.; Nishikawa, A.; Fujii, S.; Gu, J. *Methods Enzymol.* 1989, 179, 397. Examples of multi-enzyme assay methods using mammalian glycosyltransferases can be found in Gosselin, S.; Alhussaini, M.; Streiff, M. B.; Takabayashi, K.; Palcic, M. M. *Anal. Biochem.* 1994, 220, 92. Such methods were later adapted for use in microplates allowing high-throughput inhibitor screening. However, these assays often require large quantities of enzymes, limiting their application to highly abundant or cloned enzyme sources.

Radiochemical assays have also been used as functional assays for GTs since they are highly sensitive and enable the detection of low levels of enzymes (Palcic, M. M.; Pierce, M.; Hindsgaul, O. *Methods Enzymol.* 1994, 247, 215). Typically, the non-continuous assay involves the incubation of the enzyme with radiolabelled sugar-nucleotide and acceptor. After quenching the reaction, several methods exist for the separation of the unreacted radiolabelled donor from the radiolabelled glycosylated product. These include electrophoresis, ion-exchange chromatography, TLC and size exclusion chromatography for glycoproteins. More recently, von Ahsen and coworkers engineered radiochemical assays with suitable conditions for the high throughput screening of drug-like glycosidic acceptor inhibitors. (Von Ahsen, O.; Voigtmann, U.; Klotz, M.; Nifantiev, N.; Schottelius, A.; Ernst, A.; Müller-Tiemann, B; Parczyk, K. *Anal. Biochem.* 2008, 372, 96.) Their screening of nearly 800,000 compounds enabled the identification of 233 hits, mostly specific to Fucosyltransferase VII, a promising drug target for the treatment of inflammatory skin diseases. The main limitations of this radiochemical assay include hazards associated with the use and disposal of radioactive material and its lack of versatility, since it was exclusively designed for FucTVII.

Other methods available for functional GT assays include Enzyme-Linked Immunosorbant Assays (ELISA), an example of which is described in Verdon, B.; Berger, E. G.; Salchli, S.; Goldhirsch, A.; Gerber, A. Clin. Chem. 1983, 29, 1928. With highly specific antibodies or lectins, immunological assay methods have the advantage of identifying reaction products and being suitable for high throughput screening. Palcic and co-workers also developed a procedure analogous to the ELISA called the ELFIA (Enzyme-Linked Immuno-Fluorescent Assay). In this procedure, originally developed for assaying blood group A and B transferases, BSA-conjugates are coated onto nitrocellulose membranes rather than microplates. Advantageously, this provides a much faster assay than the ELISA technology (Keshvara, L. M.; Gosselin, S.; Palcic, M. M. Glycobiology 1993, 3, 416). Immunological assays based on fluorescence such as "Transcreener Assays" commercialised by BellBrook Laboratories are also available for high throughput GT inhibitor evaluation. Immunological assays are, however, unsuitable for detailed kinetic or mechanistic studies since the acceptor substrate can only be immobilised in low concentrations. Moreover, the availability of antibody or acceptor conjugate can also be a limitation especially for HTS evaluation of large libraries of inhibitors. Many other methods were designed for quantitative GT assays in both isolated enzymes and cells. One of the most recent assays relies on pH measurements and was first reported by Deng and Chen (Deng, C.; Chem, R. R. Anal. Biochem. 2004, 330, 219.) The pH-based assay relies on the detecting the absorbance change of a pH indicator, phenol red, in response to the proton release that accompanies the galactose transfer. Advantageously, the pH-based assay does not require any expensive specialised equipment or labelled substrate, and therefore was successfully applied by Palcic and Persson to automated HTS with mutated GTB enzymes.

Carbohydrate microarrays, often called "lab-on-a-chip", were also designed for GT activity and the analysis of glycan-protein or glycan-cell interactions as well as for the detection of pathogens (see Nagahori, N.; Niikura, K.; Sadamoto, R.; Taniguchi, M.; Yamagishi, A.; Monde, and K.; Nishimura, S. I. Adv. Synth. Catal. 2003, 345, 729. 46) Park, S.; Shin, I. Org. Lett. 2007, 9, 1675.)

A label-free, real-time glycosyltransferase assay based on exogenic fluorophores such as 8-anilino-1-naphtalene-sulfonate (ANS) or artificial zinc-chelated chemosensors has also been developed (see Mizyed, S.; Oddone, A.; Byczynski, B.; Hugues, D. W.; Berti, P. J. Biochemistry 2005, 44, 4011 and Wongkongkatep, J.; Miyahara, Y.; Ojida, A.; Hamachi, I. Angew. Chem. 2006, 118, 681). Attractively, these continuous assays are not limited to specific acceptors, donors or enzymes since their principle of detection only requires cleavage of the donor anomeric linkage. On the other hand, this specific mode of detection makes them unsuitable to assay enzymes other than GTs, and provides only indirect information about the GT reaction, from the formation of the secondary reaction product.

GT ligand-displacement assays, or binding assays, based on fluorescein-labelled sugar-nucleotides have previously been used successfully for the HTS of two GlcNAc transferases, MurG and OGT (see Helm, J. S, Hu, Y., Chen, L., Gross, B. & Walker, S. Identification of Active-Site Inhibitors of MurG Using a Generalizable, High-Throughput Glycosyltransferase Screen. J. Am. Chem. Soc. 125, 11168-11169 (2003). and Gross, B. J., Kraybill, B. C. & Walker, S. Discovery of O-GlcNAc transferase inhibitors. J. Am. Chem. Soc. 127, 14588-14589 (2005)). However, for each of these two enzymes an individual, tailor-made fluorophore had to be developed. This limited applicability is a significant drawback, especially as the preparation of each fluorophore required multi-step synthesis.

The present invention aims to provide an alternative to the prior art methods, and may overcome or mitigate at least one problem associated with one or more of the prior art methods, even if not expressly mentioned herein.

SUMMARY OF THE INVENTION

The present invention provides in a first aspect a compound of the formula (I):

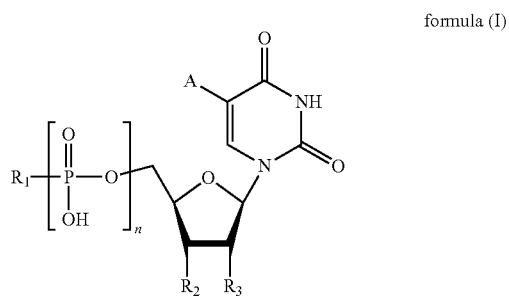

formula (I)

wherein
n is 1, 2 or 3;
$R_1$ is selected from —OH, —OPO$_3$H, —OR$_4$, —NHR$_4$, R$_6$;
$R_2$ and $R_3$ are each independently selected from —H, —OH, optionally substituted —O-alkyl and —O-alkanoyl;
$R_4$ is selected from an optionally substituted mono or polysaccharide, -alkyl, -alkenyl, -alkynyl, and L-Z, where L is a linking agent and Z is a binding agent;
$R_6$ is an optionally substituted hydrocarbon group
A is either (i) a substituted heteroaryl group, the substituent on the heteroaryl group having a double bond conjugated to the heteroaryl group, or (ii) a substituted aryl group, the substituent on the aryl group having a double bond conjugated to the aryl group.

The present invention further provides in a first aspect a compound of the formula (I):

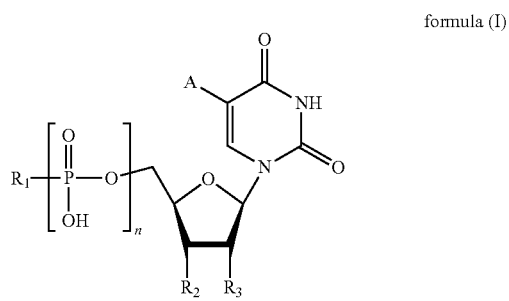

formula (I)

wherein
n is 1, 2 or 3;
$R_1$ is selected from —OH, —OPO$_3$H, —OR$_4$, —NHR$_4$;
$R_2$ and $R_3$ are each independently selected from —H, —OH, optionally substituted —O-alkyl and —O-alkanoyl;
$R_4$ is selected from an optionally substituted mono or polysaccharide, -alkyl, -alkenyl, -alkynyl, and L-Z, where L is a linking agent and Z is a binding agent;

A is either (i) a substituted heteroaryl group, the substituent on the heteroaryl group having a double bond conjugated to the heteroaryl group, or (ii) a substituted aryl group, the substituent on the aryl group having a double bond conjugated to the aryl group.

The present invention provides in a second aspect a method for determining the binding affinity of a substance to a protein selected from a glycosyltransferase protein and a glycoprocessing protein, the method comprising:
contacting in a liquid medium the materials:
   a protein selected from a glycosyltransferase protein and a glycoprocessing protein;
   a compound of formula (I) according to the first aspect; and
   a substance; and, after the contacting,
   measuring the luminescence of the materials in the liquid medium.

The present invention further provides in a second aspect a method for determining the binding affinity of a substance to a glycosyltransferase protein, the method comprising:
contacting in a liquid medium the materials:
   a glycosyltransferase protein;
   a compound of formula (I) according to the first aspect; and
   a substance; and, after the contacting,
measuring the luminescence of the materials in the liquid medium.

The present invention provides in a third aspect use of a compound of formula (I) of the first aspect in determining the binding affinity of a substance to a protein selected from a glycosyltransferase protein and a glycoprocessing protein.

The present invention further provides in a third aspect use of a compound of formula (I) of the first aspect in determining the binding affinity of a substance to a glycosyltransferase protein.

The present invention provides in a fourth aspect a kit for use in the method of the second aspect comprising:
one or more containers comprising:
   a compound of formula (I) according to the first aspect,
   and instructions on how to carry out a method for determining the binding affinity of a substance to a protein, wherein the protein is selected from a glycosyltransferase protein and a glycoprocessing protein, using the compound of formula (I).

The present invention further provides in a fourth aspect a kit for use in the method of the second aspect comprising:
one or more containers comprising:
   a compound of formula (I) according to the first aspect,
   and instructions on how to carry out a method for determining the binding affinity of a substance to a glycosyltransferase protein using the compound of formula (I).

The present invention provides in a fifth aspect an apparatus for use in the method according to the second aspect the apparatus comprising
   a container containing a compound of formula (I) according to the first aspect, and optionally one or more of a liquid medium, a protein selected from a glycosyltransferase protein and a glycoprocessing protein, and a substance, and wherein the container is adapted such that fluorescence of the compound of formula (I) can be measured.

The present invention further provides in a fifth aspect an apparatus for use in the method according to the second aspect the apparatus comprising
   a container containing a compound of formula (I) according to the first aspect, and optionally one or more of a liquid medium, a glycosyltransferase protein, and a substance, and wherein the container is adapted such that fluorescence of the compound of formula (I) can be measured.

The present invention provides in a sixth aspect a composition comprising a compound of formula (I) according to the first aspect and a protein selected from a glycosyltransferase protein and a glycoprocessing protein.

The present invention further provides in a sixth aspect a composition comprising a compound of formula (I) according to the first aspect and a glycosyltransferase protein.

The compounds of the present invention have been found to have a number of advantages. They can bind to a range of glycosyltransferases, have a high binding affinity and high fluorescence, and are therefore very effective in screening assays. The Examples below illustrate the binding of compounds of the present invention to a range of glycosyltransferases, and the unexpectedly high fluorescence of the compounds (see for example Table I and the difference between the quantum yield of compound 3d, 5-(5-Formylthien-2-yl)-UDP-α-D-galactose, and the unsubstituted phenyl analogue, 3a). The compounds of the present invention are particularly suitable in the high throughput screening of a number of test substances to determine if those substances can bind to one or more types of glycosyltransferases. Compounds of the present invention have also been found to bind to glycoprocessing enzymes, for example a UDP-Gal-4' epimerase. This is also illustrated in the Examples below.

DETAILED DESCRIPTION OF THE INVENTION

Figure 1:
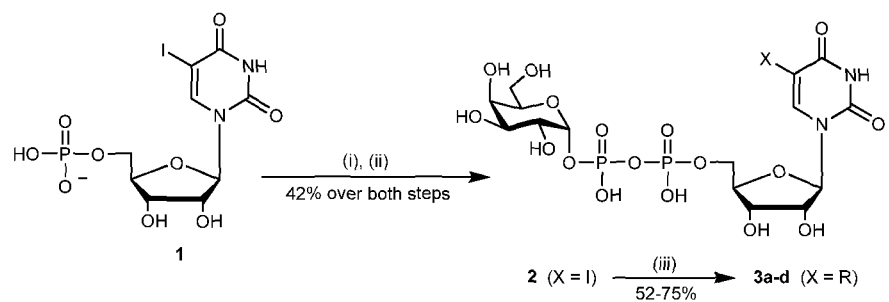
FIG. 1 shows scheme 1, which illustrates the synthesis of 5-substituted UDP-α-D-galactose derivatives 3a-d; (i) morpholine, dipyridyl disulfide, PPh$_3$, DMSO, 1 h, rt; (ii) Gal-1-P, tetrazole, DMF, rt, 5 h; (iii) R—B(OH)$_2$, Na$_2$Cl$_4$Pd, TPPTS, Cs$_2$CO$_3$, H$_2$O, 50° C. For identity of R in FIG. 1, see Table 1 below.

The present invention provides the aspects described above.

As described above, the present invention provides in a first aspect a compound of the formula (I):

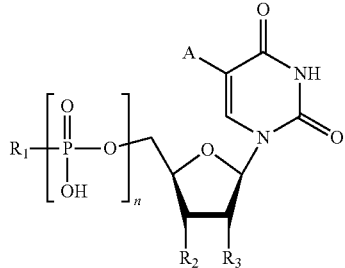

formula (I)

wherein n is 1, 2 or 3;

$R_1$ is selected from —OH, —OPO$_3$H, —OR$_4$, —NHR$_4$;

$R_2$ and $R_3$ are each independently selected from —H, —OH, optionally substituted —O-alkyl and —O-alkanoyl;

$R_4$ is selected from an optionally substituted mono or polysaccharide, -alkyl, -alkenyl, -alkynyl, and -L-Z, where L is a linking agent and Z is a binding agent;

$R_6$ is an optionally substituted hydrocarbon group;

A is either (i) a substituted heteroaryl group, the substituent on the heteroaryl group having a double bond conjugated to the heteroaryl group, or (ii) a substituted aryl group, the substituent on the aryl group having a double bond conjugated to the aryl group.

In an embodiment, the present invention provides in a first aspect a compound of the formula (I):

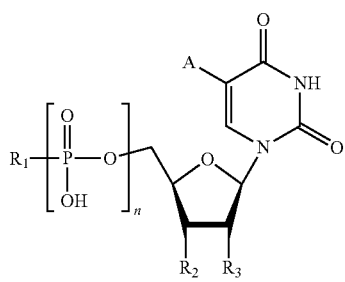

formula (I)

wherein n is 1, 2 or 3;

$R_1$ is selected from —OH, —OPO$_3$H, —OR$_4$, —NHR$_4$;

$R_2$ and $R_3$ are each independently selected from —H, —OH, optionally substituted —O-alkyl and —O-alkanoyl;

$R_4$ is selected from an optionally substituted mono or polysaccharide, -alkyl, -alkenyl, -alkynyl, and L-Z, where L is a linking agent and Z is a binding agent;

A is either (i) a substituted heteroaryl group, the substituent on the heteroaryl group having a double bond conjugated to the heteroaryl group, or (ii) a substituted aryl group, the substituent on the aryl group having a double bond conjugated to the aryl group.

In an embodiment, the present invention provides in a first aspect a compound of the formula (I):

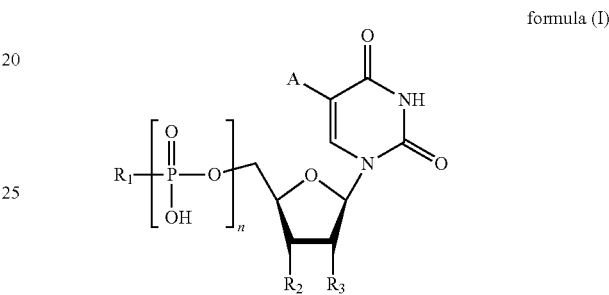

formula (I)

wherein n is 1, 2 or 3;

$R_1$ is $R_6$, $R_2$ and $R_3$ are each independently selected from —H, —OH, optionally substituted —O-alkyl and —O-alkanoyl;

$R_6$ is an optionally substituted hydrocarbon group;

A is either (i) a substituted heteroaryl group, the substituent on the heteroaryl group having a double bond conjugated to the heteroaryl group, or (ii) a substituted aryl group, the substituent on the aryl group having a double bond conjugated to the aryl group.

$R_2$ and $R_3$ are each independently selected from —H, —OH, optionally substituted —O-alkyl and —O-alkanoyl. In optionally substituted alkyl, alkyl may be selected from $C_{1-20}$ alkyl; optionally $C_{1-10}$ alkyl; optionally —$C_{1-5}$ alkyl. In optionally substituted alkanoyl, alkanoyl may be selected from $C_{1-20}$ alkanoyl; optionally $C_{1-10}$ alkanoyl; optionally —$C_{1-5}$ alkanoyl.

$R_4$, if present, is selected from an optionally substituted mono or polysaccharide, -alkyl, -alkenyl, -alkynyl, and -L-Z, where L is a linking agent and Z is a binding agent. For the avoidance of doubt, "optionally substituted" refers to all of mono or polysaccharide, -alkyl, -alkenyl and -alkynyl. The -alkyl, -alkenyl and -alkynyl may be selected from —$C_{1-20}$ alkyl, —$C_{2-20}$ alkenyl and —$C_{2-20}$ alkynyl; optionally —$C_{1-10}$ alkyl, —$C_{2-10}$ alkenyl and —$C_{2-10}$ alkynyl; optionally —$C_{1-5}$ alkyl, —$C_{2-5}$ alkenyl and —$C_{2-5}$ alkynyl.

A is either (i) a substituted heteroaryl group, the substituent on the heteroaryl group having a double bond conjugated to the heteroaryl group, or (ii) a substituted aryl group, the substituent on the aryl group having a double bond conjugated to the aryl group. A is preferably a substituted heteroaryl group, the substituent on the heteroaryl group having a double bond conjugated to the heteroaryl group. If A is a substituted heteroaryl group, "A" may comprise any type of heteroaryl ring, including, but not limited to, a 5- or 6-membered heteroaryl ring. The heteroaryl group contains one or more heteroatoms in the heteroaryl ring, optionally two or more heteroatoms in the heteroaryl ring. The one or more heteroatoms may, for example, be independently selected from S, O, and N. The heteroaryl ring in the substituted heteroaryl group may be selected from thiophene, furan, pyrrole, pyrazole, triazole, isoxazole, oxazole, thiazole, isothiazole, oxadiazoles (including 1,2,3-oxadiazole, 1,2,4-oxadiazole, 1,2,5-oxadiazols, 1,3,4-oxadiazole), pyridine, pyridazine, pyrimidine, pyrazine, triazine, as-triazine and v-triazine. The uracyl and substituent on the aryl or heteroaryl group may be attached to any atom on the aryl heteroaryl ring; preferably one or both of the uracyl and substituent on the aryl or heteroaryl ring is/are attached to a carbon atom of the aryl or heteroaryl ring.

The substituent on the aryl or heteroaryl group is one in which a double bond is conjugated to the aryl or heteroaryl group. The substituent may, for example, have a carbon-carbon double bond, one carbon of which is covalently bonded to an atom of the aryl or heteroaryl group, for example a carbon atom of the aryl or heteroaryl group. This substituent may, for example, be a carbon-oxygen double bond, the carbon of which is covalently bonded to an atom of the aryl or heteroaryl group, for example a carbon atom of the aryl or heteroaryl group. The substituent may be an alkenyl group. The alkenyl group may be selected from $C_{2-20}$ alkenyl; optionally $C_{2-10}$ alkenyl; optionally $-C_{2-5}$ alkenyl. The substituent on the heteroaryl group may be selected from acyl or alkenyl in which the C—C double bond is between $C_1$ and $C_2$, $C_1$ being the carbon in the alkenyl group covalently bonded to the heteroaryl ring. The substituent may be a substituent of the formula $-C(=X)-R_5$, wherein X is selected from O, S, NH and N-alkyl, preferably O. The alkyl in N-alkyl includes, but is not limited to, $C_{1-20}$ alkyl; optionally $C_{1-10}$ alkyl; optionally $-C_{1-5}$ alkyl. $R_5$ is preferably selected from —H and optionally substituted -alkyl, -alkenyl and -alkynyl; optionally $-C_{1-20}$ alkyl, $-C_{2-20}$ alkenyl and $-C_{2-20}$ alkynyl; optionally $-C_{1-10}$ alkyl, $-C_{2-10}$ alkenyl and $-C_{2-10}$ alkynyl; optionally $-C_{1-5}$ alkyl, $-C_{2-5}$ alkenyl and $-C_{2-5}$ alkynyl. The substituent may comprise from 1 to 20 carbons, optionally from 1 to 10 carbons, optionally 1 to 5 carbons. The substituent may be covalently bonded to the aryl ring of the aryl group or heteroaryl ring of the heteroaryl group at two or more atoms, such that the substituent and the aryl ring or heteroaryl ring may together form a further ring. The aryl or heteroaryl group may have one or more further substituents, which do not have a double bond conjugated to the aryl or heteroaryl group. Such further substituents may be as described below.

Z is a binding agent. Z is preferably a group that can bind to a solid substrate, for example a wall or base of a container, for example a well of a plate, for example a microwell or microtitre plate, or the surface of a bead, for example a polymeric bead. Such groups are known to those skilled in the art. Z may, for example, comprise one member of a specific binding pair. The other member of the binding pair may be bound to the surface of a solid substrate, which may be as described herein. The binding pair may, for example, be selected from biotin:avidin or streptavidin, antibody:antigen or protein A, receptor:ligand, nucleic acid:nucleic acid (e.g. DNA:DNA), wheatgerm agglutin (WGA):N-acetyl β glucosamine residues or glycoproteins, glutathione:GST (glutathione-S-transferase) and copper:histidine tag. Other suitable binding pairs are known to the skilled person. Alternatively, the binding can be achieved by electrostatic interaction, for example by creating a positively charged species on Z which is bound to a negatively charged species on the solid substrate. Preferably, Z is biotin. This allows binding of Z to a substrate having avidin or streptavidin bound to its surface. Binding agents are described in a number of prior art references, one of which is EP-A-1269192, which is incorporated herein by reference.

L is a linking agent. L is not particularly restricted. It may be any group capable of linking the binding agent Z to the remaining part of the molecule in formula (I). Such groups are known to the skilled person. It may, for example, be or contain a group selected from alkylene, alkenylene and alkynylene; optionally $-C_{1-20}$ alkylene, $-C_{2-20}$ alkenylene and $-C_{2-20}$ alkynylene; optionally $-C_{1-10}$ alkylene, $-C_{2-10}$ alkenylene and $-C_{2-10}$ alkynylene; optionally $-C_{1-5}$ alkylene, $-C_{2-5}$ alkenylene and $-C_{2-5}$ alkynylene. It may be or contain a polymeric group. The polymeric group may, for example, be a water-soluble polymeric group, for example a polyethylene glycol (PEG) or polyvinylpyrrolidone. Examples of water-soluble linking agents are described in EP-A-1269192, which is incorporated herein by reference.

In an embodiment, L-Z may be selected from C(O)-alkylene-NH-(biotinyl), C(O)-alkenylene-NH-(biotinyl), and C(O)-alkynylene-NH-(biotinyl); and wherein optionally alkylene, alkenylene and alkynylene are selected from $-C_{1-20}$ alkylene, $-C_{2-20}$ alkenylene and $-C_{2-20}$ alkynylene; optionally $-C_{1-10}$ alkylene, $-C_{2-10}$ alkenylene and $-C_{2-10}$ alkynylene; optionally $-C_{1-5}$ alkylene, $-C_{2-5}$ alkenylene and $-C_{2-5}$ alkynylene.

The compound of formula (I) may be a compound of the formula (II):

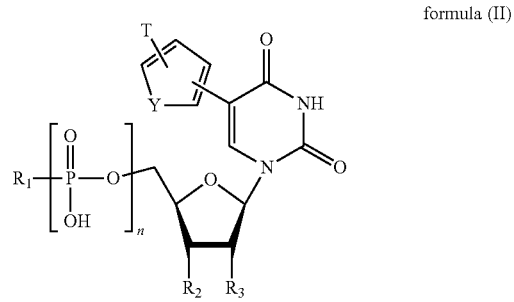

formula (II)

wherein
n, $R_1$, $R_2$ and $R_3$ are as defined above for formula (I);
Y is selected from O, S, NH, and N-alkyl;
T is a substituent as defined above.

T may be selected from alkenyl (preferably alkenyl in which the C—C double bond is between $C_1$ and $C_2$, $C_1$ being the carbon in the alkenyl group covalently bonded to the heteroaryl ring) and a group of the formula $-C(=X)-R_5$, wherein X is selected from O, S, NH and N-alkyl, preferably O. The alkyl in N-alkyl includes, but is not limited to, $C_{1-20}$ alkyl; optionally $C_{1-10}$ alkyl; optionally $-C_{1-5}$ alkyl. $R_5$ is preferably selected from —H and optionally substituted -alkyl, -alkenyl and -alkynyl; optionally $-C_{1-20}$ alkyl, $-C_{2-20}$ alkenyl and $-C_{2-20}$ alkynyl; optionally $-C_{1-10}$ alkyl, $-C_{2-10}$ alkenyl and $-C_{2-10}$ alkynyl; optionally $-C_{1-5}$ alkyl, $-C_{2-5}$ alkenyl and $-C_{2-5}$ alkynyl.

The uracyl group and T group may be attached at any position on the 5-membered heterocyclic ring in formula (II). Taking the nomenclature for the heterocyclic ring wherein Y in formula I is the 1-position, and, proceeding anticlockwise, the adjacent carbon atom is the 2-position, the next adjacent carbon atom is the 3-position, and so on, the uracyl group may, for example, be at the 2-position and the T group may be at the 3-, 4- or 5-position. Using this same nomenclature, in another embodiment, the uracyl group may, for example, be at the 3-position, and the T group may be at the 2-, 4- or 5-position of the 5-membered heterocyclic ring. Preferably, the uracyl group is in the 2-position and the T group is at the 5-position.

In the compounds of formula (I) and (II), n is preferably 2.

In the compounds of formula (I) and (II), $R_1$ is preferably selected from —OH, —OPO$_3$H, —OR$_4$, and —NHR$_4$, wherein preferably $R_4$ is selected from an optionally substituted monosaccharide.

The optionally substituted monosaccharide may be selected from selected from glucose, galactose, galactosamine, glucosamine; xylose, fucose and glucuronic acid, and acylated derivatives thereof. The monosaccharide may be an L or D-monosaccharide, and is preferably a D-monosaccharide. The monosaccharide may be an α- or β-monosaccharide. Preferably, the saccharide is an α-D-monosaccharide.

In the compounds of formula (I) and (II), $R_2$ and $R_3$ are each preferably selected from —OH and optionally substituted —O-alkyl and —O-alkanoyl.

In formula (I), one or more heteroatoms in the heteroaryl group is/are preferably S. In the compound of formula (II), Y is preferably S.

In an embodiment, in formula (I) or (II) $R_1$ is $R_6$; wherein $R_6$ is an optionally substituted hydrocarbon group; the optionally substituted hydrocarbon group may be selected from an optionally substituted alkyl group, an optionally substituted alkene group and an optionally substituted alkyne group, preferably an optionally substituted alkyl group. $R_6$ may be a hydrocarbon group substituted with $R_4$ as defined above. $R_6$ may be a hydrocarbon group substituted with an optionally substituted mono or polysaccharide, and -L-Z, where L is a linking agent and Z is a binding agent. Preferably $R_6$ is a hydrocarbon group substituted with an optionally substituted mono or polysaccharide. The optionally substituted mono or polysaccharide may be covalently bonded to the hydrocarbon group via any type of glycosidic bond, for example an O-glycosidic bond, a n N-glycosidic bond, an S-glycosidic bond and a C-glycosidic bond. If the hydrocarbon group is covalently bonded to the mono or polysaccharide via a C-glycosidic bond, preferably a carbon of the hydrocarbon replaces the O that would have been present in an analogous O-glycosidic bond. $R_6$ is preferably an optionally substituted $C_{1\ to\ 10}$ hydrocarbon group, more preferably an optionally substituted $C_{1\ to\ 5}$ hydrocarbon group, more preferably an optionally substituted $C_{1\ to\ 3}$ hydrocarbon group, most preferably a $C_2$ hydrocarbon group. $R_6$ is preferably an optionally substituted $C_{1\ to\ 10}$ alkyl group, more preferably an optionally substituted $C_{1\ to\ 5}$ alkyl group, more preferably an optionally substituted $C_{1\ to\ 3}$ alkyl group, most preferably an optionally substituted $C_2$ alkyl group.

Figure 9:
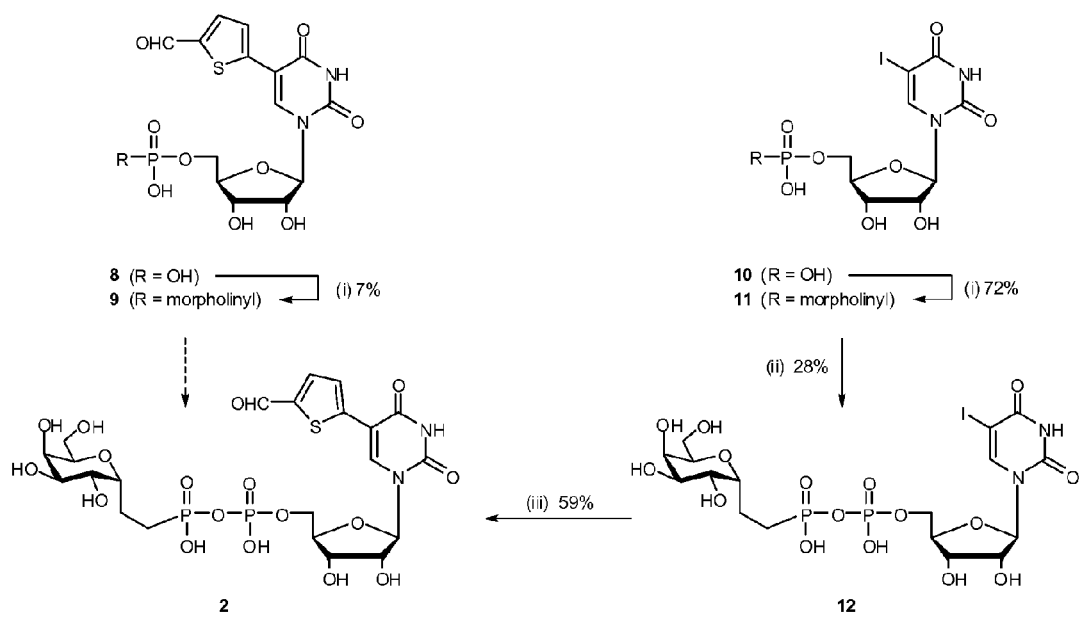

In an embodiment, n is 1 or 2, preferably 2, $R_1$ is optionally substituted $C_{1\ to\ 3}$ alkyl, preferably an optionally substituted $C_2$ alkyl. Preferably, $R_1$ is $C_{1\ to\ 3}$ alkyl substituted with a mono or polysaccharide, and wherein the $C_{1\ to\ 3}$ alkyl is linked to the mono or polysaccharide by a C-glycosidic bond. Preferably, a carbon of the $C_{1\ to\ 3}$ alkyl replaces the O that would have been present in an analogous O-glycosidic bond. The mono or polysaccharide may be as described herein, for example as on page 14 above. In an embodiment, the compound of formula (I) is compound 2 as shown in FIG. 9.

The above embodiments in which $R_1$ is $R_6$, wherein $R_6$ is an optionally substituted hydrocarbon group, have been found to be surprisingly hydrolytically stable.

The term "alkyl" or "alkan", by itself or as part of another substituent, means, unless otherwise stated, a straight or branched chain, or cyclic (a cycloalkyl)hydrocarbon radical, or combination thereof, which may be fully saturated and optionally may be substituted. Each alkyl may independently be a C1-20 alkyl, optionally a C1-10 alkyl, optionally a C1-5 alkyl, optionally C1-3 alkyl, optionally C1-2 alkyl. Examples of saturated hydrocarbon radicals include, but are not limited to, groups such as methyl, ethyl, n-propyl, isopropyl, n-butyl, t-butyl, isobutyl sec-butyl, cyclohexyl, (cyclohexyl)methyl, cyclopropylmethyl, homologs and isomers of, for example, n-pentyl, n-hexyl, n-heptyl, n-octyl, and the like. The term "alkyl," unless otherwise noted, optionally includes derivatives of alkyl.

The term "alkylene" means, unless otherwise stated, a straight or branched chain, or cyclic (a cycloalkylene) divalent hydrocarbon radical, or combination thereof, which may be fully saturated and optionally may be substituted. Unless otherwise stated, "alkylene" means optionally substituted alkylene. Each alkyl may independently be a C1-20 alkylene, optionally a C1-10 alkylene, optionally a C1-5 alkylene, optionally C1-3 alkylene, optionally C1-2 alkylene. Examples of saturated hydrocarbon radicals include, but are not limited to, groups such as methylene, ethylene, n-propylene, and isopropylene.

The term "cycloalkyl" refers to any cyclic alkyl ring. Each cycloalkyl may independently be a C3-8 cycloalkyl, optionally a C5-7 cycloalkyl, optionally a C6 cycloalkyl. Examples of cycloalkyl groups include cyclopropyl, cyclobutyl, cyclopentyl and cyclohexyl. Unless otherwise stated, "cycloalkyl" means optionally substituted cycloalkyl.

The term "acyl" refers to a group of the formula —C(=O)—R, in which R is selected from H and optionally substituted-alkyl, -alkenyl, -alkynyl. The alkyl, -alkenyl and -alkynyl may be selected from —$C_{1-20}$ alkyl, —$C_{2-20}$ alkenyl and —$C_{2-20}$alkynyl; optionally —$C_{1-10}$ alkyl, —$C_{2-10}$ alkenyl and —$C_{2-10}$alkynyl; optionally —$C_{1-5}$ alkyl, —$C_{2-5}$ alkenyl and —$C_{2-5}$ alkynyl.

The term "alkenyl" as a group or part of a group refers to any linear or branched chain hydrocarbon radical containing at least one carbon-carbon double bond, which may occur at any point along the chain. Unless otherwise stated, "alkenyl" means optionally substituted alkenyl. Each alkenyl may independently be a C2-20 alkenyl, optionally a C2-10 alkenyl, optionally a C2-5 alkenyl, optionally C2-3 alkenyl. E- and Z-forms are both included, where applicable. Examples of alkenyl groups include vinyl, allyl, butenyl and pentenyl.

The term "alkenylene" refers to any linear or branched chain divalent hydrocarbon radical containing at least one carbon-carbon double bond, which may occur at any point along the chain. Unless otherwise stated, "alkenylene" means optionally substituted alkenylene. Each alkenylene may independently be a C2-20 alkenylene, optionally a C2-10 alkenylene, optionally a C2-5 alkenylene, optionally C2-3 alkenylene. E- and Z-forms are both included, where applicable. Examples of alkenylene groups include vinylene, allylene, butenylene and pentenylene.

The term "alkynyl" as a group or part of a group refers to any linear or branched chain hydrocarbon containing at least one carbon-carbon triple bond, which may occur at any point along the chain. Unless otherwise stated, "alkynyl" means optionally substituted alkynyl. Each alkynyl may independently be a C2-20 alkynyl, optionally a C2-10 alkynyl, optionally a C2-5 alkynyl, optionally C2-3 alkynyl. Examples of suitable alkynyl groups include ethynyl, propynyl, butynyl and pentynyl.

The term "alkynylene" refers to any linear or branched chain divalent hydrocarbon radical containing at least one carbon-carbon triple bond, which may occur at any point along the chain. Unless otherwise stated, "alkynylene" means optionally substituted alkynylene. Each alkynylene may independently be a C2-20 alkynylene, optionally a C2-10 alkynylene, optionally a C2-5 alkynylene, optionally C2-3 alkynylene. Examples of suitable alkynylene groups include ethynylene, propynylene, butynylene and pentynylene.

Where a compound or group is described as "optionally substituted," the compound or group may be unsubstituted or one or more substituents may be present. Furthermore, optional substituents may be attached to the compounds or groups which they substitute in a variety of ways, either directly or through a connecting group such as amine, amide, ester, ether, thioether, sulfonamide, sulfamide, sulfoxide, urea, thiourea and urethane. As appropriate, an optional substituent may itself be substituted by another substituent, either directly to the former or through a connecting group such as those exemplified above. Substituents may each independently be selected from alkyl, alkenyl, alkynyl, —O-alkyl, —O-alkanoyl, halogen, heterocyclyl, alkoxycarbonyl, hydroxy, mercapto, nitro, acyloxy, hydroxy, thiol, acyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

Optionally substituted mono- or polysaccharides include, but are not limited to, mono- and polysaccharides in which at least one hydroxy group has been replaced with one or more substituents, which may be as described above.

The term "halogen" or "halo" means fluorine, chlorine, bromine and iodine (alternatively referred to as fluoro, chloro, bromo and iodo, respectively).

The term "aryl" as a group or part of a group, includes, but is not limited to, phenyl or naphthyl. The term "heteroaryl" as a group or part of a group includes, but is not limited to, a 5- or 6-membered aromatic ring containing one or more heteroatoms, optionally 1, 2 or 3 heteroatoms, and the heteroatoms may be selected from N, O and S, attached through a ring carbon or nitrogen. Examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl and tetrazolyl.

The term "heterocyclyl" as a group or part of a group means a 5- to 7-membered saturated or unsaturated non-aromatic ring having one or more heteroatoms, for example 1, 2, 3 or 4 heteroatoms, optionally selected from N, O and S, attached through a ring carbon or nitrogen.

The compound of formula (I) may be bound to a solid substrate. The compound of formula (I) may, for example, contain the group L-Z, as described above, and Z is bound to the solid substrate. The solid substrate may be any suitable substrate for carrying out a solid phase assay, including, but not limited to a polymeric substrate, for example a substrate comprising polystyrene. The substrate may comprise the wall or base of a well of a multi-well plate or microtitre plate or a polymeric bead.

The present invention provides in a second aspect a method for determining the binding affinity of a substance to a protein selected from a glycosyltransferase protein and a glycoprocessing protein, the method comprising:
contacting in a liquid medium the materials:
    a protein selected from a glycosyltransferase protein and a glycoprocessing protein;
    a compound of formula (I) according to the first aspect; and
    a substance; and, after the contacting,
    measuring the luminescence of the materials in the liquid medium.

In an embodiment, the present invention provides in a second aspect a method for determining the binding affinity of a substance to a glycosyltransferase protein, the method comprising:
contacting in a liquid medium the materials:
    a glycosyltransferase protein;
    a compound of formula (I); and
    a substance; and, after the contacting,
    measuring the luminescence of the materials in the liquid medium.

In an embodiment, the present invention provides in a second aspect a method for determining the binding affinity of a substance to a glycoprocessing protein, the method comprising:
contacting in a liquid medium the materials:
    a glycoprocessing protein;
    a compound of formula (I); and
    a substance; and, after the contacting,
    measuring the luminescence of the materials in the liquid medium.

As mentioned above, the protein is selected from a glycosyltransferase protein and a glycoprocessing protein. Optionally, the protein is a glycosyltransferase protein. Optionally, the protein is a glycoprocessing protein.

The glycosyltransferase protein may be a Leloir-type enzyme, which are known to the skilled person. Leloir-type enzymes can catalyse glycosyl transfer using sugar nucleotides as the glycosyl donor. The glycosyltransferase protein may be selected from a galactosyltransferase, a N-acetylgalactosyltransferase, a glucosyltransferase, a N-acetylglucosyltransferase, a xylosyltransferase, a glucuronyltransferase, a mannosyltransferase, and a fucosyltransferase.

The glycoprocessing protein may be an enzyme which catalyses the stereochemical or structural isomerisation of a sugar-nucleotide substrate, for example a UDP-monosaccharide, for example UDP-galactose and/or UDP-glucose. In the present application, a glycoprocessing protein is not a glycosyltransferase protein. Optionally, the glycoprocessing protein is an isomerase, for example an isomerase having an EC (Enzyme Commission) number of 5. The isomerase may be selected from isomerases having an EC number of 5.1, 5.2, 5.3, 5.4, 5.5 and 5.99. Most preferably, the isomerase is an isomerase having an EC number of 5.1 and 5.4. Isomerases having an EC number of 5.1 include racemases and epimerases. Isomerases having an EC number of 5.2 include enzymes that catalyze the isomerization of geometric isomers (e.g. cis-trans isomerases). Isomerases having an EC number of 5.3 include intramolecular oxidoreductases. Isomerases having an EC number of 5.4 include intramolecular transferases (mutases). Isomerases having an EC number of 5.5 includes intramolecular lyases. Isomerases having an EC number of 5.99 include other isomerases (including topoisomerases). The isomerase is preferably a protein that binds with and/or can act upon a sugar-nucleotide substrate, for example a UDP-monosaccharide, for example UDP-galactose and/or UDP-glucose. In an embodiment, the glycoprocessing enzyme is a glycosylepimerase or UDP-glucopyranose mutase protein, preferably a galactose epimerase, more preferably a uridinediphosphate (UDP)-galactose-4'-epimerase. For example, the glycosyl epimerase may catalyse the conversion of UDP-Gal into UDP-Glc, as shown below

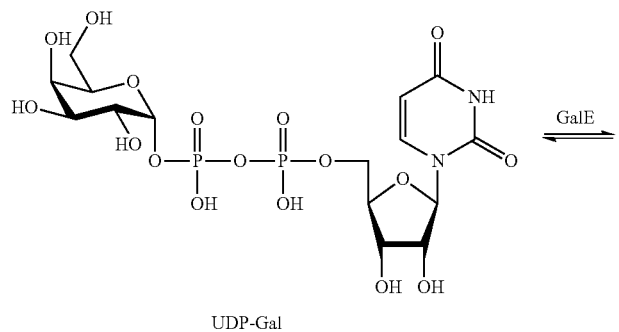

UDP-Gal            UDP-Glc

The glycosyltransferase may be a galactosyltransferase. The glycosyl transferase may be selected from any of the following:

GTB (*H. Sapiens*), the amino acid sequence for which is (SEQ ID NO: 1)
MAEVLRTLAGKPKCHALRPMILFLIMLVLVLFGYGVLSPRSLMPGSLER

GFCMAVREPDHLQRVSLPRMVYPQPKVLTPCRKDVLVVTPWLAPIVWEG

TFNIDILNEQFRLQNTTIGLTVFAIKKYVAFLKLFLETAEKHFMVGHRV

HYYVFTDQPAAVPRVTLGTGRQLSVLEVGAYKRWQDVSMRRMEMISDFC

ERRFLSEVDYLVCVDVDMEFRDHVGVEILTPLFGTLHPSFYGSSREAFT

YERRPQSQAYIPKDEGDFYYMGAFFGGSVQEVQRLTRACHQAMMVDQAN

GIEAVWHDESHLNKYLLRHKPTKVLSPEYLWDQQLLGWPAVLRKLRFTA

VPKNHQAVRNP;

GTA (*H. Sapiens*), the amino acid sequence for which is (SEQ ID NO: 2)
MAEVLRTLAGKPKCHALRPMILFLIMLVLVLFGYGVLSPRSLMPGSLER

GFCMAVREPDHLQRVSLPRMVYPQPKVLTPCRKDVLVVTPWLAPIVWEG

TFNIDILNEQFRLQNTTIGLTVFAIKKYVAFLKLFLETAEKHFMVGHRV

HYYVFTDQPAAVPRVTLGTGRQLSVLEVRAYKRWQDVSMRRMEMISDFC

ERRFLSEVDYLVCVDVDMEFRDHVGVEILTPLFGTLHPGFYGSSREAFT

YERRPQSQAYIPKDEGDFYYLGGFFGGSVQEVQRLTRACHQAMMVDQAN

GIEAVWHDESHLNKYLLRHKPTKVLSPEYLWDQQLLGWPAVLRKLRFTA

VPKNHQAVRNP;

GTA & GTB mutants (e.g. AA(Gly)B), as described in e.g. Persson, M; Letts, J. A.; Hosseini-Maaf, B.; Borisova, S. N.; Palcic, M. M.; Evans, S. V. & Olsson, M. L. *Structural Effects of Naturally Occurring Human Blood Group B Galactosyltransferase Mutations Adjacent to the DXD Motif.* J. Biol. Chem. 282, 9564-9570 (2007), and Alfaro, J. A.; Zheng, R. B.; Persson, M; Letts, J. A.; Polakowski, R.; Bai, Y.; Borisova, S. N.; Seto, N. O. L.; Lowary, T. L.; Palcic, M. M. & Evans, S. V. ABO(H) *Blood Group A and B Glycosyltransferases Recognize Substrate via Specific Conformational Changes.* J. Biol. Chem. 283, 10097-10108 (2008); the amino acid sequences for the enzymes in these documents, each of which may be used in the present invention, are as follows:

ABBB (SEQ ID NO: 3)
MAEVLRTLAGKPKCHALRPMILFLIMLVLVLFGYGVLSPRSLMPGSLER

GFCMAVREPDHLQRVSLPRMVYPQPKVLTPCRKDVLVVTPWLAPIVWEG

TFNIDILNEQFRLQNTTIGLTVFAIKKYVAFLKLFLETAEKHFMVGHRV

HYYVFTDQPAAVPRVTLGTGRQLSVLEVRAYKRWQDVSMRRMEMISDFC

ERRFLSEVDYLVCVDVDMEFRDHVGVEILTPLFGTLHPSFYGSSREAFT

YERRPQSQAYIPKDEGDFYYMGAFFGGSVQEVQRLTRACHQAMMVDQAN

GIEAVWHDESHLNKYLLRHKPTKVLSPEYLWDQQLLGWPAVLRKLRFTA

VPKNHQAVRNP;

AABB (SEQ ID NO: 4)
MAEVLRTLAGKPKCHALRPMILFLIMLVLVLFGYGVLSPRSLMPGSLERGFCMAVREPDH

LQRVSLPRMVYPQPKVLTPCRKDVLVVTPWLAPIVWEGTFNIDILNEQFRLQNTTIGLTV

FAIKKYVAFLKLFLETAEKHFMVGHRVHYYVFTDQPAAVPRVTLGTGRQLSVLEVRAYKR

WQDVSMRRMEMISDFCERRFLSEVDYLVCVDVDMEFRDHVGVEILTPLFGTLHPGFYGSS

REAFTYERRPQSQAYIPKDEGDFYYMGAFFGGSVQEVQRLTRACHQAMMVDQANGIEAVW

HDESHLNKYLLRHKPTKVLSPEYLWDQQLLGWPAVLRKLRFTAVPKNHQAVRNP;

AAGlyB (SEQ ID NO: 5)
MAEVLRTLAGKPKCHALRPMILFLIMLVLVLFGYGVLSPRSLMPGSLERGFCMAVREPDH
LQRVSLPRMVYPQPKVLTPCRKDVLVVTPWLAPIVWEGTFNIDILNEQFRLQNTTIGLTV
FAIKKYVAFLKLFLETAEKHFMVGHRVHYYVFTDQPAAVPRVTLGTGRQLSVLEVRAYKR
WQDVSMRRMEMISDFCERRFLSEVDYLVCVDVDMEFRDHVGVEILTPLFGTLHPGFYGSS
REAFTYERRPQSQAYIPKDEGDFYYGGAFFGGSVQEVQRLTRACHQAMMVDQANGIEAVW
HDESHLNKYLLRHKPTKVLSPEYLWDQQLLGWPAVLRKLRFTAVPKNHQAVRNP;

GTB-M214T (SEQ ID NO: 6)
MAEVLRTLAGKPKCHALRPMILFLIMLVLVLFGYGVLSPRSLMPGSLERGFCMAVREPDH
LQRVSLPRMVYPQPKVLTPCRKDVLVVTPWLAPIVWEGTFNIDILNEQFRLQNTTIGLTV
FAIKKYVAFLKLFLETAEKHFMVGHRVHYYVFTDQPAAVPRVTLGTGRQLSVLEVGAYKR
WQDVSMRRMEMISDFCERRFLSEVDYLVCVDVDTEFRDHVGVEILTPLFGTLHPSFYGSS
REAFTYERRPQSQAYIPKDEGDFYYMGAFFGGSVQEVQRLTRACHQAMMVDQANGIEAVW
HDESHLNKYLLRHKPTKVLSPEYLWDQQLLGWPAVLRKLRFTAVPKNHQAVRNP;

GTB-M214R (SEQ ID NO: 7)
MAEVLRTLAGKPKCHALRPMILFLIMLVLVLFGYGVLSPRSLMPGSLERGFCMAVREPDH
LQRVSLPRMVYPQPKVLTPCRKDVLVVTPWLAPIVWEGTFNIDILNEQFRLQNTTIGLTV
FAIKKYVAFLKLFLETAEKHFMVGHRVHYYVFTDQPAAVPRVTLGTGRQLSVLEVGAYKR
WQDVSMRRMEMISDFCERRFLSEVDYLVCVDVDREFRDHVGVEILTPLFGTLHPSFYGSS
REAFTYERRPQSQAYIPKDEGDFYYMGAFFGGSVQEVQRLTRACHQAMMVDQANGIEAVW
HDESHLNKYLLRHKPTKVLSPEYLWDQQLLGWPAVLRKLRFTAVPKNHQAVRNP;

GTB-M214V (SEQ ID NO: 8)
MAEVLRTLAGKPKCHALRPMILFLIMLVLVLFGYGVLSPRSLMPGSLERGFCMAVREPDH
LQRVSLPRMVYPQPKVLTPCRKDVLVVTPWLAPIVWEGTFNIDILNEQFRLQNTTIGLTV
FAIKKYVAFLKLFLETAEKHFMVGHRVHYYVFTDQPAAVPRVTLGTGRQLSVLEVGAYKR
WQDVSMRRMEMISDFCERRFLSEVDYLVCVDVDVEFRDHVGVEILTPLFGTLHPSFYGSS
REAFTYERRPQSQAYIPKDEGDFYYMGAFFGGSVQEVQRLTRACHQAMMVDQANGIEAVW
HDESHLNKYLLRHKPTKVLSPEYLWDQQLLGWPAVLRKLRFTAVPKNHQAVRNP;

Ggta1 (*B. taurus*) (bovine α-1,3-GalT), the amino acid sequence for which is (SEQ ID NO: 9)
MNVKGKVILSMLVVSTVIVVFWEYIHSPEGSLFWINPSRNPEVGGSSIQKGWWLPRWFNN
GYHEEDGDINEEKEQRNEDESKLKLSDWFNPFKRPEVVTMTKWKAPVVWEGTYNRAVLDN
YYAKQKITVGLTVFAVGRYIEHYLEEFLTSANKHFMVGHPVIFYIMVDDVSRMPLIELGP
LRSFKVFKIKPEKRWQDISMMRMKTIGEHIVAHIQHEVDFLFCMDVDQVFQDKFGVETLG -continued

ESVAQLQAWWYKADPNDFTYERRKESAAYIPFGEGDFYYHAAIFGGTPTQVLNITQECFK

GILKDKKNDIEAQWHDESHLNKYFLLNKPTKILSPEYCWDYHIGLPADIKLVKMSWQTKE

YNVVRNNV;

LgtC (*N. meningitidis*) (*Neisseria* β-1,4-GalT), the amino acid sequence for which is (SEQ ID NO: 10)

MDIVFAADDNYAAYLCVAAKSVEAAHPDTEIRFHVLDAGISEANRAAVAANLRGGGGNIR

FIDVNPEDFAGFPLNIRHISITTYARLKLGEYIADCDKVLYLDIDVLVRDSLTPLWDTDL

GDNWLGACIDLFVERQEGYKQKIGMADGEYYFNAGVLLINLKKWRRHDIFKMSCEWVEQY

KDVMQYQDQDILNGLFKGGVCYANSRFNFMPTNYAFMANWFASRHTDPLYRDRTNTVMPV

AVSHYCGSAKPWHRDCTAWGAERFTELGGSLTTVPEEWRGKLAVPHRMFSTKRMLQRWRR

KLSARFLRKIY;

bovine β-1,4-GalT, the amino acid sequence for which is (SEQ ID NO: 11)

MKFREPLLGGSAAMPGASLQRACRLLVAVCALHLGVTLVYYLAGRDLRRLPQLVGVHPPL

QGSSHGAAAIGQPSGELRLRGVAPPPPLQNSSKPRSRAPSNLDAYSHPGPGPGPGSNLTS

APVPSTTTRSLTACPEESPLLVGPMLIEFNIPVDLKLVEQQNPKVKLGGRYTPMDCISPH

KVAIIIPFRNRQEHLKYWLYYLHPILQRQQLDYGIYVINQAGESMFNRAKLLNVGFKEAL

KDYDYNCFVFSDVDLIPMNDHNTYRCFSQPRHISVAMDKFGFSLPYVQYFGGVSALSKQQ

FLSINGFPNNYWGWGGEDDDIYNRLAFRGMSVSRPNAVIGKCRMIRHSRDKKNEPNPQRF

DRIAHTKETMLSDGLNSLTYMVLEVQRYPLYTKITVDIGTPS;

human β-1,4-GalT, the amino acid sequence for which is (SEQ ID NO: 12)

MRLREPLLSGSAAMPGASLQRACRLLVAVCALHLGVTLVYYLAGRDLSRLPQLVGVSTPL

QGGSNSAAAIGQSSGELRTGGARPPPPLGASSQPRPGGDSSPVVDSGPGPASNLTSVPVP

HTTALSLPACPEESPLLVGPMLIEFNMPVDLELVAKQNPNVKMGGRYAPRDCVSPHKVAI

IIPFRNRQEHLKYWLYYLHPVLQRQQLDYGIYVINQAGDTIFNRAKLLNVGFQEALKDYD

YTCFVFSDVDLIPMNDHNAYRCFSQPRHISVAMDKFGFSLPYVQYFGGVSALSKQQFLTI

NGFPNNYWGWGGEDDDIFNRLVFRGMSISRPNAVVGRCRMIRHSRDKKNEPNPQRFDRIA

HTKETMLSDGLNSLTYQVLDVQRYPLYTQITVDIGTPS;

β-1,4-GalTs, β-1,3-GalTs, α-1,4-GalTs and α-1,3-GalTs from other species, as described in e.g. Namdjou, D. J.; Chen, H. M.; Vinogradov, E.; Brochu, D.; Withers, S. G. & Wakarchuk, W. W. A beta-1,4-galactosyltransferase from *Helicobacter pylori is an efficient and versatile biocatalyst displaying a novel activity for thioglycoside synthesis*. ChemBioChem 9, 1632-1640 (2008); the amino acid sequences for the enzymes in this document, each of which may be used in the present invention, are as follows

*Helicobacter pylori* b1.4-GalT (SEQ ID NO: 13)

MRVFAISLNQKVCDTFGLVFRDTTTLLNSINATHHQAQIFDAIYSKTFEGGLHPLVKKHL

HPYFITQNIKDMGITTNLISEVSKFYYALKYHAKFMSLGELGCYASHYSLWEKCIELNEA

ICILEDDITLKEDFKEGLDFLEKHIQELGYIRLMHLLYDASVKSEPLSHKNHEIQERVGI

-continued

IKAYSEGVGTQGYVITPKIAKVFLKCSRKWVVPVDTIMDATFIHGVKNLVLQPFVIADDE

QISTIARKEEPYSPKIALMRELHFKYLKYWQFV;

*Neisseria meningitidis* LgtB (SEQ ID NO: 14)
MQNHVISLASAAERRAHIADTFGRHGIPFQFFDALMPSERLEQAMAELVPGLSAHPYLSG

VEKACFMSHAVLWKQALDEGLPYITVFEDDVLLGEGAEKFLAEDAWLQERFDPDTAFIVR

LETMFMHVLTSPSGVADYCGRAFPLLESEHWGTAGYIISRKAMRFFLDRFAALPPEGLHP

VDLMMFSDFFDREGMPVCQLNPALCAQELHYAKFHDQNSALGSLIEHDRLLNRKQQRRDS

PANTFKHRLIRALTKISREREKRRQRREQFIVPFQ;

*H. sapiens* MGAT I (GnT-I), the amino acid sequence for which is:

(SEQ ID NO: 15)
MLKKQSAGLVLWGAILFVAWNALLLLFFWTRPAPGRPPSVSALDGDPASLTREVIRLAQD

AEVELERQRGLLQQIGDALSSQRGRVPTAAPPAQPRVPVTPAPAVIPILVIACDRSTVRR

CLDKLLHYRPSAELFPIIVSQDCGHEETAQAIASYGSAVTHIRQPDLSSIAVPPDHRKFQ

GYYKIARHYRWALGQVFRQFRFPAAVVVEDDLEVAPDFFEYFRATYPLLKADPSLWCVSA

WNDNGKEQMVDASRPELLYRTDFFPGLGWLLLAELWAELEPKWPKAFWDDWMRRPEQRQG

RACIRPEISRTMTFGRKGVSHGQFFDQHLKFIKLNQQFVHFTQLDLSYLQREAYDRDFLA

RVYGAPQLQVEKVRTNDRKELGEVRVQYTGRDSFKAFAKALGVMDDLKSGVPRAGYRGIV

TFQFRGRRVHLAPPPTWEGYDPSWN;

*H. sapiens* MGAT V (GnT-V), the amino acid sequence for which is (SEQ ID NO: 16)
MALFTPWKLSSQKLGFFLVTFGFIWGMMLLHFTIQQRTQPESSSMLREQILDLSKRYIKA

LAEENRNVVDGPYAGVMTAYDLKKTLAVLLDNILQRIGKLESKVDNLVVNGTGTNSTNST

TAVPSLVALEKINVADIINGAQEKCVLPPMDGYPHCEGKIKWMKDMWRSDPCYADYGVDG

STCSFFIYLSEVENWCPHLPWRAKNPYEEADHNSLAEIRTDFNILYSMMKKHEEFRWMRL

RIRRMADAWIQAIKSLAEKQNLEKRKRKKVLVHLGLLTKESGFKIAETAFSGGPLGELVQ

WSDLITSLYLLGHDIRISASLAELKEIMKKVVGNRSGCPTVGDRIVELIYIDIVGLAQFK

KTLGPSWVHYQCMLRVLDSFGTEPEFNHANYAQSKGHKTPWGKWNLNPQQFYTMFPHTPD

NSFLGFVVEQHLNSSDIHHINEIKRQNQSLVYGKVDSFWKNKKIYLDIIHTYMEVHATVY

GSSTKNIPSYVKNHGILSGRDLQFLLRETKLFVGLGFPYEGPAPLEAIANGCAFLNPKFN

PPKSSKNTDFFIGKPTLRELTSQHPYAEVFIGRPHVWTVDLNNQEEVEDAVKAILNQKIE

PYMPYEFTCEGMLQRINAFIEKQDFCHGQVMWPPLSALQVKLAEPGQSCKQVCQESQLIC

EPSFFQHLNKDKDMLKYKVTCQSSELAKDILVPSFDPKNKHCVFQGDLLLFSCAGAHPRH

QRVCPCRDFIKGQVALCKDCL;

*H. sapiens* OGT, the amino acid sequence for which is (SEQ ID NO: 17)
MASSVGNVADSTEPTKRMLSFQGLAELAHREYQAGDFEAAERHCMQLWRQEPDNTGVLLL

LSSIHFQCRRLDRSAHFSTLAIKQNPLLAEAYSNLGNVYKERGQLQEAIEHYRHALRLKP

DFIDGYINLAAALVAAGDMEGAVQAYVSALQYNPDLYCVRSDLGNLLKALGRLEEAKACY

LKAIETQPNFAVAWSNLGCVFNAQGEIWLAIHHFEKAVTLDPNFLDAYINLGNVLKEARI

FDRAVAAYLRALSLSPNHAVVHGNLACVYYEQGLIDLAIDTYRRAIELQPHFPDAYCNLA

NALKEKGSVAEAEDCYNTALRLCPTHADSLNNLANIKREQGNIEEAVRLYRKALEVFPEF

AAAHSNLASVLQQQGKLQEALMHYKEAIRISPTFADAYSNMGNTLKEMQDVQGALQCYTR

AIQINPAFADAHSNLASIHKDSGNIPEAIASYRTALKLKPDFPDAYCNLAHCLQIVCDWT

DYDERMKKLVSIVADQLEKNRLPSVHPHHSMLYPLSHGFRKAIAERHGNLCLDKINVLHK

PPYEHPKDLKLSDGRLRVGYVSSDFGNHPTSHLMQSIPGMHNPDKFEVFCYALSPDDGTN

FRVKVMAEANHFIDLSQIPCNGKAADRIHQDGIHILVNMNGYTKGARNELFALRPAPIQA

MWLGYPGTSGALFMDYIITDQETSPAEVAEQYSEKLAYMPHTFFIGDHANMFPHLKKKAV

IDFKSNGHIYDNRIVLNGIDLKAFLDSLPDVKIVKMKCPDGGDNADSSNTALNMPVIPMN

TIAEAVIEMINRGQIQITINGFSISNGLATTQINNKAATGEEVPRTIIVTTRSQYGLPED

AIVYCNFNQLYKIDPSTLQMWANILKRVPNSVLWLLRFPAVGEPNIQQYAQNMGLPQNRI

IFSPVAPKEEHVRRGQLADVCLDTPLCNGHTTGMDVLWAGTPMVTMPGETLASRVAASQL

TCLGCLELIAKNRQEYEDIAVKLGTDLEYLKKVRGKVWKQRISSPLFNTKQYTMELERLY

LQMWEHYAAGNKPDHMIKPVEVTESA;

*E. coli* MurG, the amino acid sequence for which is (SEQ ID NO: 18)
MSGQGKRLMVMAGGTGGHVFPGLAVAHHLMAQGWQVRWLGTADRMEADLVPKHGIEIDFI

RISGLRGKGIKALIAAPLRIFNAWRQARAIMKAYKPDVVLGMGGYVSGPGGLAAWSLGIP

VVLHEQNGIAGLTNKWLAKIATKVMQAFPGAFPNAEVVGNPVRTDVLALPLPQQRLAGRE

GPVRVLVVGGSQGARILNQTMPQVAAKLGDSVTIWHQSGKGSQQSVEQAYAEAGQPQHKV

TEFIDDMAAAYAWADVVVCRSGALTVSEIAAAGLPALFVPFQHKDRQQYWNALPLEKAGA

AKIIEQPQLSVDAVANTLAGWSRETLLTMAERARAASIPDATERVANEVSRVARA;

*Bacillus subtilis* SpsA, the amino acid sequence for which is (SEQ ID NO: 19)
MPKVSVIMTSYNKSDYVAKSISSILSQTFSDFELFIMDDNSNEETLNVIRPFLNDNRVRF

YQSDISGVKERTEKTRYAALINQAIEMAEGEYITYATDDNIYMPDRLLKMVRELDTHPEK

AVIYSASKTYHLNENRDIVKETVRPAAQVTWNAPCAIDHCSVMHRYSVLEKVKEKFGSYW

DESPAFYRIGDARFFWRVNHFYPFYPLDEELDLNYITDQSIHFQLFELEKNEFVRNLPPQ

RNCRELRESLKKLGMG;

*H. sapiens* beta-1.4-GalT II, the amino acid sequence for which is (SEQ ID NO: 20)
MSRLLGGTLERVCKAVLLLCLLHFLVAVILYFDVYAQHLAFFSRFSARGPAHALHPAASS
SSSSSNCSRPNATASSSGLPEVPSALPGTAPTLPPCPDSPPGLVGRLLIEFTSPMPLER
VQRENPGVLMGGRYTPPDCTPAQTVAVIIPFRHREHHLRYWLHYLHPILRRQRLRYGVYV
INQHGEDTFNRAKLLNVGFLEALKEDAAYDCFIFSDVDLVPMDDRNLYRCGDQPRHFAIA
MDKFGFRLPYAGYFGGVSGLSKAQFLRINGFPNEYWGWGGEDDDIFNRISLTGMKISRPD
IRIGRYRMIKHDRDKHNEPNPQRFTKIQNTKLTMKRDGIGSVRYQVLEVSRQPLFTNITV
DIGRPPSWPPRG;

*H. sapiens* beta-1.4-GalT III, the amino acid sequence for which is (SEQ ID NO: 21)
MLRRLLERPCTLALLVGSQLAVMMYLSLGGFRSLSALFGRDQGPTFDYSHPRDVYSNLSH
LPGAPGGPPAPQGLPYCPERSPLLVGPVSVSFSPVPSLAEIVERNPRVEPGGRYRPAGCE
PRSRTAIIVPHRAREHHLRLLLYHLHPFLQRQQLAYGIYVIHQAGNGTFNRAKLLNVGVR
EALRDEEWDCLFLHDVDLLPENDHNLYVCDPRGPRHVAVAMNKFGYSLPYPQYFGGVSAL
TPDQYLKMNGFPNEYWGWGGEDDDIATRVRLAGMKISRPPTSVGHYKMVKHRGDKGNEEN
PHRFDLLVRTQNSWTQDGMNSLTYQLLARELGPLYTNITADIGTDPRGPRAPSGPRYPPG
SSQAFRQEMLQRRPPARPGPLSTANHTALRGSH;

*H. sapiens* beta-1.4-GalT IV, the amino acid sequence for which is (SEQ ID NO: 22)
MGFNLTFHLSYKFRLLLLLTLCLTVVGWATSNYFVGAIQEIPKAKEFMANFHKTLILGKG
KTLTNEASTKKVELDNCPSVSPYLRGQSKLIFKPDLTLEEVQAENPKVSRGRYRPQECKA
LQRVAILVPHRNREKHLMYLLEHLHPFLQRQQLDYGIYVIHQAEGKKFNRAKLLNVGYLE
ALKEENWDCFIFHDVDLVPENDFNLYKCEEHPKHLVVGRNSTGYRLRYSGYFGGVTALSR
EQFFKVNGFSNNYWGWGGEDDDLRLRVELQRMKISRPLPEVGKYTMVFHTRDKGNEVNAE
RMKLLHQVSRVWRTDGLSSCSYKLVSVEHNPLYINITVDFWFGA;

*H. sapiens* beta-1.4-GalT V, the amino acid sequence for which is (SEQ ID NO: 23)
MRARRGLLRLPRRSLLAALFFFSLSSSLLYFVYVAPGIVNTYLFMMQAQGILIRDNVRTI
GAQVYEQVLRSAYAKRNSSVNDSDYPLDLNHSETFLQTTTFLPEDFTYFANHTCPERLPS
MKGPIDINMSEIGMDYIHELFSKDPTIKLGGHWKPSDCMPRWKVAILIPFRNRHEHLPVL
FRHLLPMLQRQRLQFAFYVVEQVGTQPFNRAMLFNVGFQEAMKDLDWDCLIFHDVDHIPE
SDRNYYGCGQMPRHFATKLDKYMLLPYTEFFGGVSGLTVEQFRKINGFPNAFWGWGGED
DDLWNRVQNAGYSVSRPEGDTGKYKSIPHHHRGEVQFLGRYALLRKSKERQGLDGLNNLN
YFANITYDALYKNITVNLTPELAQVNEY;

*H. sapiens* beta-1.4-GalT VI, the amino acid sequence for which is (SEQ ID NO: 24)
```
MSVLRRMMRVSNRSLLAFIFFFSLSSSCLYFIYVAPGIANTYLFMVQARGIMLRENVKTI

GHMIRLYTNKNSTLNGTDYPEGNNSSDYLVQTTTYLPENFTYSPYLPCPEKLPYMRGFLN

VNVSEVSFDEIHQLFSKDLDIEPGGHWRPKDCKPRWKVAVLIPFRNRHEHLPIFFLHLIP

MLQKQRLEFAFYVIEQTGTQPFNRAMLFNVGFKEAMKDSVWDCVIFHDVDHLPENDRNYY

GCGEMPRHFAAKLDKYMYILPYKEFFGGVSGLTVEQFRKINGFPNAFWGWGGEDDDLWNR

VHYAGYNVTRPEGDLGKYKSIPHHHRGEVQFLGRYKLLRYSKERQYIDGLNNLIYRPKIL

VDRLYTNISVNLMPELAPIEDY;
```
and

*H. sapiens* beta-1.4-GalT VII, the amino acid sequence for which is (SEQ ID NO: 25)
```
MFPSRRKAAQLPWEDGRSGLLSGGLPRKCSVFHLFVACLSLGFFSLLWLQLSCSGDVARA

VRGQGQETSGPPRACPPEPPPEHWEEDASWGPHRLAVLVPFRERFEELLVFVPHMRRFLS

RKKIRHHIYVLNQVDHFRFNRAALINVGFLESSNSTDYIAMHDVDLLPLNEELDYGFPEA

GPFHVASPELHPLYHYKTYVGGILLLSKQHYRLCNGMSNRFWGWGREDDEFYRRIKGAGL

QLFRPSGITTGYKTFRHLHDPAWRKRDQKRIAAQKQEQFKVDREGGLNTVKYHVASRTAL

SVGGAPCTVLNIMLDCDKTATPWCTFS
```

In an embodiment, the glycoprocessing protein may be a galactose epimerase, and may be selected from any of the following:

*Streptococcus thermophilus* Galactose epimerase, as described in Poolman B, Royer T J, Mainzer S E, Schmidt B F Carbohydrate utilization in *Streptococcus thermophilus*: characterization of the genes for aldose 1-epimerase (mutarotase) and UDPglucose 4-epimerase. *J. Bacteriol.* 1990, 172(7), 4037-4047; the amino acid sequence for the *Streptococcus thermophilus* Galactose epimerase is as follows:

(SEQ ID NO: 26)
```
MAILVLGGAGYIGSHMVDRLVEKGQEKVVVVDSLVTGHRAAVHPDAIFYQGDLSDQDFMR

KVFKENPDVDAVIHFAAYSLVGESMEKPLKYFDNNTAGMVKLLEVMNECGVKYIVFSSTA

ATYGIPEEIPILETTPQNPINPYGESKLMMETIMKWSDQAYGIKYVPLRYFNVAGANLMV

RLVRTRSETHLLPIILQVAQGVREKIMIFGDDYNTPDGTNVRDYVHPFDLADAHLLAVEY

LRKGNESTAFNLGSSTGFSNLQILEAARKVTGKEIPAEKADRRPGDPDILIASSEKARTV

LGWKPQFDNIEKIIASAWAWHSSHPKGYDDRG;
```

*H. sapiens* GalE (SEQ ID NO: 27)
```
MAEKVLVTGGAGYIGSHTVLELLEAGYLPVVIDNFHNAFRGGGSLPESLRRVQELTGRSV

EFEEMDILDQGALQRLFKKYSFMAVIHFAGLKAVGESVQKPLDYYRVNLTGTIQLLEIMK

AHGVKNLVFSSSATVYGNPQYLPLDEAHPTGGCTNPYGKSKFFIEEMIRDLCQADKTWNA

VLLRYFNPTGAHASGCIGEDPQGIPNNLMPYVSQVAIGRREALNVFGNDYDTEDGTGVRD

YIHVVDLAKGHIAALRKLKEQCGCRIYNLGTGTGYSVLQMVQAMEKASGKKIPYKVVARR

EGDVAACYANPSLAQEELGWTAALGLDRMCEDLWRWQKQNPSGFGTQA;
```

*E. coli* GalE (SEQ ID NO: 28)
MRVLVTGGSGYIGSHTCVQLLQNGHDVIILDNLCNSKRSVLPVIERLGGKHPTFVEGDIR

NEALMTEILHDHAIDTVIHFAGLKAVGESVQKPLEYYDNNVNGTLRLISAMRAANVKNFI

FSSSATVYGDQPKIPYVESFPTGTPQSPYGKSKLMVEQILTDLQKAQPDWSIALLRYFNP

VGAHPSGDMGEDPQGIPNNLMPYIAQVAVGRRDSLAIFGNDYPTEDGTGVRDYIHVMDLA

DGHVVAMEKLANKPGVHIYNLGAGVGNSVLDVVNAFSKACGKPVNYHFAPRREGDLPAYW

ADASKADRELNWRVTRTLDEMAQDTWHWQSRHPQGYPD;

*Haemophilus influenzae* GalE (SEQ ID NO: 29)
MAILVTGGAGYIGSHTVVELLNVGKEVVVLDNLCNSSPKSLERVKQITGKEAKFYEGDIL

DRALLQKIFAENEINSVIHFAGLKAVGESVQKPTEYYMNNVAGTLVLIQEMKKAGVWNFV

FSSSATVYGDPKIIPITEDCEVGGTTNPYGTSKYMVEQILRDTAKAEPKFSMTILRYFNP

VGAHESGLIGEDPNGIPNNLLPYISQVAIGKLAQLSVFGSDYDTHDGTGVRDYIHVVDLA

VGHLKALQRHENDAGLHIYNLGTGHGYSVLDMVKAFEKANNITIAYKLVERRSGDIATCY

SDPSLAAKELGWVAERGLEKMMQDTWNWQKNNPKGYRD;

*Neisseria meningitides* GalE (SEQ ID NO: 30)
MKKILVTGGTGFIGSHTVVSLLKSGHQVVILDNLCNSSINILPRLKTITGQEIPFYQGDI

RDREILRRIFAENRIDSVIHFAGLKAVGESVAEPMKYYDNNVSGSLVLAEEMARAGVFSI

VFSSSATVYGDPGKVPYTEDMPPGDTTSPYGASKSMVERILTDIQKADPRWSMILLRYFN

PIGAHESGLIGEQPNGIPNNLLPYICQVAAGKLPQLAVFGDDYPTPDGTGMRDYIHVMDL

AEGHVAAMQAKSNVAGTHLLNLGSGRASSVLEIIRAFEAASGLTIPYEVKPRRAGDLACF

YADPSYTKAQIGWQTQRDLTQMMEDSWRWVSNNPNGYDD;
and

*Trypanosoma brucei* Gal E (SEQ ID NO: 31)
MRVLVCGGAGYIGSHFVRALLRDTNHSVVIVDSLVGTHGKSDHVETRENVARKLQQSDGP

KPPWADRYAALEVGDVRNEDFLNGVFTRHGPIDAVVHMCAFLAVGESVRDPLKYYDNNVV

GILRLLQAMLLHKCDKIIFSSSAAIFGNPTMGSVSTNAEPIDINAKKSPESPYGESKLIA

ERMIRDCAEAYGIKGICLRYFNACGAHEDGDIGEHYQGSTHLIPIILGRVMSDIAPDQRL

TIHEDASTDKRMPIFGTDYPTPDGTCVRDYVHVCDLASAHILALDYVEKLGPNDKSKYFS

VFNLGTSRGYSVREVIEVARKTTGHPIPVRECGRREGDPAYLVAASDKAREVLGWKPKYD

TLEAIMETSWKFQRTHPNGYASQENGTPGGRTTKL;

In an embodiment, the glycoprocessing protein may be a UDP-galactopyranose mutase, and may be selected from any of the following:

*E. coli* UDP-Galp mutase (SEQ ID NO: 32)
MYDYIIVGSGLFGAVCANELKKLNKKVLVIEKRNHIGGNAYTEDCEGIQIHKYGAHIFHT

NDKYIWDYVNDLVEFNRFTNSPLAIYKDKLFNLPFNMNTFHQMWGVKDPQEAQNIINAQK

-continued
KKYGDKVPENLEEQAISLVGEDLYQALIKGYTEKQWGRSAKELPAFIIKRIPVRFTFDNN

YFSDRYQGIPVGGYTKLIEKMLEGVDVKLGIDFLKDKDSLASKAHRIIYTGPIDQYFDYR

FGALEYRSLKFETERHEFPNFQGNAVINFTDANVPYTRIIEHKHFDYVETKHTVVTKEYP

LEWKVGDEPYYPVNDNKNMELFKKYRELASREDKVIFGGRLAEYKYYDMHQVISAALYQV

KNIMSTD;
and

Mycoplasma genitalium UDP-Galp mutase (SEQ ID NO: 33)
MNVILSVMLFSSPSCVNINSFDILIVGAGISGIVLANILANHNKRVLIVEKRDHIGGNCY

DKVDSKTQLLFHQYGPHIFHTNNQTVINFISPFFELNNYHHRVGLKLKNNLDLTLPFDFQ

QIYKLMGKDGRKLVSFFKENFSLNTHLSLAELQLIDNPLAQKLYQFLISNVYKPYSVKMW

GLPFAMINENVINRVKIVLSEQSSYFPDAIIQGLPKSGYTNSFLKMLANPLIDVQLNCKD

NLLVYQDEKLFFNNNLIEKPVVYCGLIDKLFNFCFGHLQYRSLAFSWKRFNQKKYQTYPV

VNMPLAKSITRSVEYKQLTNQGSFKPQTIVSFETPGSYAINDPRFNEPYYPINNTLNDTL

FKKYWKKASKLKNLHLLGRLATYQYIDMDKAILLSIKKAQQLLS

All amino acid sequences given above are listed in the amino to carboxy direction from left to right, in accordance with standard nomenclature.

The glycosyltransferase may be a galactosyltransferase, which may be selected from LgtC (*N. meningitidis*), Ggta1 (*B. taurus*), GTB (*H. sapiens*) and AA(Gly)B GTB mutant (*H. sapiens*). The amino acid sequences for these enzymes are given above, and can also be found in the references mentioned above.

The substance is a substance to be tested for its binding affinity to the protein selected from a glycosyltransferase protein and a glycoprocessing protein, and is different from the compound of formula (I) used in the method (although the substance may also be of formula (I)). The substance may comprise an organic compound.

The measuring of the luminescence may comprise measuring the intensity of the luminescence, e.g. the fluorescence, of the materials in the liquid medium, for example at wavelength at which the intensity of the luminescence of the compound of formula (I) is at a maximum. The luminescence, e.g., the fluorescence, of the materials in the liquid medium may be compared to the luminescence of a positive control tested under the same conditions. The compound of formula (I) may be present in the liquid medium before the contacting, and the luminescence of the materials in the liquid medium before the contacting may be compared to the luminescence of the materials after the contacting.

The method may comprise:
providing the protein selected from a glycosyltransferase protein and a glycoprocessing protein and the compound of formula (I) in the liquid medium; adding the substance to the liquid medium; and
measuring the luminescence of the materials in the liquid medium before and after adding the substance to the liquid medium to detect a difference in the luminescence. A rise in the luminescence intensity, e.g. fluorescence intensity, will normally be indicative of the binding of the substance to the protein selected from a glycosyltransferase protein and a glycoprocessing protein. Optionally, the protein is a glycosyltransferase protein. Optionally, the protein is a glycoprocessing protein.

The method may comprise:
providing the glycosyltransferase protein and the compound of formula (I) in the liquid medium;
adding the substance to the liquid medium; and
measuring the luminescence of the materials in the liquid medium before and after adding the substance to the liquid medium to detect a difference in the luminescence. A rise in the luminescence intensity, e.g. fluorescence intensity, will normally be indicative of the binding of the substance to the glycosyltransferase.

The method may comprise:
providing the compound of formula (I) and the substance in a liquid medium; adding the protein selected from a glycosyltransferase protein and a glycoprocessing protein to the liquid medium; and
measuring the luminescence of the materials in the liquid medium before and after adding the substance to the liquid medium to detect a difference in the luminescence. Optionally, the protein is a glycosyltransferase protein. Optionally, the protein is a glycoprocessing protein. A fall in the fluorescence intensity will normally be indicative of the compound of formula (I) binding to the protein selected from a glycosyltransferase protein and a glycoprocessing protein and the degree of the difference in fluorescence intensity will be indicative of the extent to which the substance binds to the protein selected from a glycosyltransferase protein and a glycoprocessing protein compared to the compound of formula (I); the higher the difference, the greater the binding affinity of the compound of formula (I) to the protein selected from a glycosyltransferase protein and a glycoprocessing protein compared to the substance. This method has been found to be particularly effective in determining the binding affinity of a substance that may itself be fluorescent.

The method may comprise:
providing the compound of formula (I) and the substance in a liquid medium; adding the glycosyltransferase protein to the liquid medium; and
measuring the luminescence of the materials in the liquid medium before and after adding the substance to the liquid medium to detect a difference in the luminescence. A fall in the fluorescence intensity will normally be indicative of the compound of formula (I) binding to the glycosyltransferase and the degree of the difference in fluorescence intensity will be indicative of the extent to which the substance binds to the glycosyltransferase compared to the compound of formula (I); the higher the difference, the greater the binding affinity of the compound of formula (I) to the glycosyltransferase protein compared to the substance. This method has been found to be particularly effective in determining the binding affinity of a substance that may itself be fluorescent.

The method may comprise the procedures:
(i) contacting in a liquid medium the materials:
a protein selected from a glycosyltransferase protein and a glycoprocessing protein;
a compound of formula (I); and
a first substance; and, after the contacting,
measuring luminescence of the materials in the liquid medium,
(ii) contacting in a liquid medium the materials:
a protein selected from a glycosyltransferase protein and a glycoprocessing protein;
a compound of formula (I); and
a second substance; and, after the contacting,
measuring the luminescence of the materials in the liquid medium;
comparing the luminescence obtained in procedure (i) with the luminescence obtained in procedure (ii). Optionally, the protein is a glycosyltransferase protein. Optionally, the protein is a glycoprocessing protein. The conditions in procedures (i) and (ii) should be the same, apart from the identity of the first and second substances. The method may be carried out to compare the binding affinity for a plurality of different substances on a particular protein selected from a glycosyltransferase protein and a glycoprocessing protein.

The method may comprise the procedures:
(i) contacting in a liquid medium the materials:
a glycosyltransferase protein;
a compound of formula (I); and
a first substance; and, after the contacting,
measuring luminescence of the materials in the liquid medium,
(ii) contacting in a liquid medium the materials:
a glycosyltransferase protein;
a compound of formula (I); and
a second substance; and, after the contacting,
measuring the luminescence of the materials in the liquid medium;
comparing the luminescence obtained in procedure (i) with the luminescence obtained in procedure (ii). The conditions in procedures (i) and (ii) should be the same, apart from the identity of the first and second substances. The method may be carried out to compare the binding affinity for a plurality of different substances on a particular glycosyltransferase protein.

The method may comprise the procedures:
(i) contacting in a liquid medium the materials:
a first protein selected from a glycosyltransferase protein and a glycoprocessing protein;
a compound of formula (I); and
a substance; and, after the contacting,
measuring luminescence of the materials in the liquid medium,
(ii) contacting in a liquid medium the materials:
a second protein selected from a glycosyltransferase protein and a glycoprocessing protein;
a compound of formula (I); and
a substance; and, after the contacting,
measuring the luminescence of the materials in the liquid medium;
comparing the luminescence obtained in procedure (i) with the luminescence obtained in procedure (ii). Optionally, the first and second proteins are each a glycosyltransferase protein. Optionally, the first and second proteins are each a glycoprocessing protein. The conditions in procedures (i) and (ii) should be the same, apart from the identity of the first and second proteins. The method may be carried out to compare the binding affinity of a substance on a plurality of a proteins selected from a glycosyltransferase protein and a glycoprocessing protein.

The method may comprise the procedures:
(i) contacting in a liquid medium the materials:
a first glycosyltransferase protein;
a compound of formula (I); and
a substance; and, after the contacting,
measuring luminescence of the materials in the liquid medium,
(ii) contacting in a liquid medium the materials:
a second glycosyltransferase protein;
a compound of formula (I); and
a substance; and, after the contacting,
measuring the luminescence of the materials in the liquid medium;
comparing the luminescence obtained in procedure (i) with the luminescence obtained in procedure (ii). The conditions in procedures (i) and (ii) should be the same, apart from the identity of the first and second glycosyltransferase proteins. The method may be carried out to compare the binding affinity of a substance on a plurality of glycosyltransferase proteins.

In the methods described above, the compound of formula (I) may be bound to a solid substrate. The compound of formula (I) may, for example, contain the group L-Z, as described above, and Z is bound to the solid substrate. The solid substrate may be any suitable substrate for carrying out a solid phase assay, including, but not limited to a polymeric substrate. Solid phase assay indicates that the compound is bound to a solid phase; the components used in solid phase assays may be in the liquid phase, for example in a liquid medium as described above. The substrate may comprise the wall or base of a well of a multi-well plate or microtitre plate or a polymeric bead. Any of the methods described herein may comprise the step, before the contacting, of binding the compound of formula (I) to a solid substrate.

The method may be carried out using the apparatus described below. The method may be carried out in multi-well plates or microtitre plates. The method may be carried out a plurality of times using a multi-well plate, with the conditions differing in the wells such that, for example, different substances and/or different glycosyl proteins are present in each well. Accordingly, the rapid comparison of the binding affinities of one or more different types of substances to one or more different types of glycosyl transferase proteins can be carried out. The method may be carried out by an automated device. The method may be carried out as a high throughput screening method.

The liquid medium may be any medium in which the protein selected from a glycosyltransferase protein and a glycoprocessing protein can be suspended and/or dissolved.

The liquid medium should be a medium in which the compound of formula (I) can be bound to the protein selected from a glycosyltransferase protein and a glycoprocessing protein. Preferably, the liquid medium comprises a protic solvent. The protic solvent may comprise an alcohol, such as methanol or ethanol, and/or water. Preferably, the liquid medium comprises water. The liquid medium may comprise a protic solvent and a non-protic solvent, wherein the amount of non-protic solvent is less than the protic solvent. The non-protic solvent should be miscible with the protic solvent. The non-protic solvent may be selected from 1,4-dioxane, tetrahydrofuran, dichloromethane, acetone, acetonitrile, dimethylformamide and dimethyl sulfoxide. The non-protic solvent may be present in the liquid medium in an amount of 10% v/v or less, optionally 7% v/v or less, optionally 5% v/v or less.

The liquid medium preferably comprises a divalent metal ion, M. Divalent metals ions have been found to assist the binding of the compound of the present invention to the glycosyltransferase protein. The divalent metal ion may be a divalent transition metal ion. The divalent transition metal ion may be selected from Sc, Ti, V, Cr, Mn, Fe Co, Ni, Cu and Zn. The divalent metal ion preferably comprises Mn. The divalent metal ion is preferably in the $M^{2+}$ oxidation state in the liquid medium. The liquid medium preferably comprises $Mn^{2+}$. Any suitable counter anion for the divalent metal ion may be employed in the liquid medium. Preferably, the counter anion is an inorganic counterion. The counterion may be any anion that allows dissolution of the divalent metal ion in the liquid medium, for example at the concentrations disclosed below. The counter anion may be selected from a halide, acetate, sulphate, hydrogensulphate, carbonate, hydrogencarbonate, phosphate, hydrogenphosphate, formate, lactate, tartrate, nitrate, molybdate, hydroxide and oxide, and hydrates thereof. Halides include, for example, fluoride, chloride, bromide or iodide. The divalent metal ion may be present in the liquid medium at a concentration of at least 1 mM, optionally at least 5 mM, optionally, at least 10 mM. The divalent metal ion may be present in the liquid medium at a concentration of 100 mM or less, optionally 50 mM or less.

The compound of the present invention may be present in the liquid medium at a concentration of at least 10 nM, optionally at least 50 nM, optionally at least 100 nM, optionally at least 150 nM. The compound of the present invention may be present in the liquid medium at a concentration of 500 nM or less, optionally at least 400 nM or less, optionally at least 300 nM or less. The compound of the present invention may be present in the liquid medium at a concentration of 500 nM or less, optionally 400 nM or less, optionally 300 nM or less.

The pH of the liquid medium may be at least 6.5. The pH of the liquid medium may be 7.5 or less. The pH of the liquid medium may be between 6.7 and 7.3. The pH of the liquid medium may be about 7.

The liquid medium may comprise a buffer. Suitable buffers are known to the skilled person, and include, but are not limited to, a tris/HCl buffer.

The protein selected from a glycosyltransferase protein and a glycoprocessing protein is preferably present in the liquid medium in an amount such that at least 70 molar % of the compound of the present invention can be bound to the protein selected from a glycosyltransferase protein and a glycoprocessing protein (in the absence of the substance to be tested), more preferably in an amount such that at least 80 molar % of the compound of the present invention can be bound to the protein selected from a glycosyltransferase protein and a glycoprocessing protein (in the absence of the substance to be tested), most preferably in an amount such that at least 90 molar % of the compound of the present invention can be bound to the protein selected from a glycosyltransferase protein and a glycoprocessing protein (in the absence of the substance to be tested). This may be determined by means known to those skilled in the art, for example by using standardised graphs in which the fluorescence of the compound in the liquid medium (in the absence of the protein selected from a glycosyltransferase protein and a glycoprocessing protein) is plotted against concentration, from which it can be determined how much of the compound in the liquid medium containing the protein selected from a glycosyltransferase protein and a glycoprocessing protein is free (i.e. not bound to the protein selected from a glycosyltransferase protein and a glycoprocessing protein) and therefore how much of the compound is bound to the protein selected from a glycosyltransferase protein and a glycoprocessing protein.

The glycosyltransferase protein is preferably present in the liquid medium in an amount such that at least 70 molar % of the compound of the present invention can be bound to the glycosyltransferase protein (in the absence of the substance to be tested), more preferably in an amount such that at least 80 molar % of the compound of the present invention can be bound to the glycosyltransferase protein (in the absence of the substance to be tested), most preferably in an amount such that at least 90 molar % of the compound of the present invention can be bound to the glycosyltransferase protein (in the absence of the substance to be tested). This may be determined by means known to those skilled in the art, for example by using standardised graphs in which the fluorescence of the compound in the liquid medium (in the absence of glycosyltransferase) is plotted against concentration, from which it can be determined how much of the compound in the liquid medium containing the glycosyltransferase is free (i.e. not bound to the glycosyltransferase) and therefore how much of the compound is bound to the glycosyltransferase.

The present invention provides in a third aspect use of a compound of formula (I) of the first aspect in determining the binding affinity of a substance to a protein selected from a glycosyltransferase protein and a glycoprocessing protein. The use preferably involves use of a compound of formula (I) of the first aspect in determining the binding affinity of a substance to a protein selected from a glycosyltransferase protein and a glycoprocessing protein in a binding assay.

The present invention further provides in a third aspect use of a compound of formula (I) of the first aspect in determining the binding affinity of a substance to a glycosyltransferase protein. The use preferably involves use of a compound of formula (I) of the first aspect in determining the binding affinity of a substance to a glycosyltransferase protein in a binding assay.

The present invention further provides in a third aspect use of a compound of formula (I) of the first aspect in determining the binding affinity of a substance to a glycoprocessing protein. The use preferably involves use of a compound of formula (I) of the first aspect in determining the binding affinity of a substance to a glycoprocessing protein in a binding assay.

The present invention provides in a fourth aspect a kit for use in the method of the second aspect comprising:
one or more containers comprising:
    a compound of formula (I) according to the first aspect,
    and instructions on how to carry out a method for determining the binding affinity of a substance to a protein selected from a glycosyltransferase protein and a glycoprocessing protein using the compound of formula (I). The kit may further comprise, optionally in separate containers, (i) a protein selected from a glycosyltransferase protein and a glycoprocessing protein and/or (ii) a liquid medium suitable for allowing the binding of the compound of formula (I) to the protein selected from a glycosyltransferase protein and a glycoprocessing protein within the liquid medium. The one or more containers may be suitable for use in the method of the present invention.

The present invention further provides in a fourth aspect a kit for use in the method of the second aspect comprising: one or more containers comprising:
a compound of formula (I) according to the first aspect, and instructions on how to carry out a method for determining the binding affinity of a substance to a glycosyltransferase protein using the compound of formula (I). The kit may further comprise, optionally in separate containers, (i) a glycosyltransferase protein and/or (ii) a liquid medium suitable for allowing the binding of the compound of formula (I) to the glycosyltransferase protein within the liquid medium. The one or more containers may be suitable for use in the method of the present invention.

The present invention further provides in a fourth aspect a kit for use in the method of the second aspect comprising: one or more containers comprising:
a compound of formula (I) according to the first aspect, and instructions on how to carry out a method for determining the binding affinity of a substance to a glycoprocessing protein using the compound of formula (I). The kit may further comprise, optionally in separate containers, (i) a glycoprocessing protein and/or (ii) a liquid medium suitable for allowing the binding of the compound of formula (I) to the glycoprocessing protein within the liquid medium. The one or more containers may be suitable for use in the method of the present invention.

The present invention provides in a fifth aspect an apparatus for use in the method according to the second aspect the apparatus comprising
a container containing a compound of formula (I) according to the first aspect, and optionally one or more of a liquid medium, a protein selected from a glycosyltransferase protein and a glycoprocessing protein, and a substance, and wherein the container is adapted such that fluorescence of the compound of formula (I) can be measured. The container may be a multi-well plate for use in a high throughput screening process. Optionally, one or more of the wells, preferably a plurality of the wells, contain a compound of formula (I) according to the first aspect, and optionally one or more of a liquid medium, a protein selected from a glycosyltransferase protein and a glycoprocessing protein, and a substance. The container may constitute all or part of the solid substrate as described herein.

The present invention provides in a fifth aspect an apparatus for use in the method according to the second aspect the apparatus comprising
a container containing a compound of formula (I) according to the first aspect, and optionally one or more of a liquid medium, a glycosyltransferase protein, and a substance, and wherein the container is adapted such that fluorescence of the compound of formula (I) can be measured. The container may be a multi-well plate for use in a high throughput screening process. Optionally, one or more of the wells, preferably a plurality of the wells, contain a compound of formula (I) according to the first aspect, and optionally one or more of a liquid medium, a glycosyltransferase protein, and a substance. The container may constitute all or part of the solid substrate as described herein.

The present invention provides in a fifth aspect an apparatus for use in the method according to the second aspect the apparatus comprising
a container containing a compound of formula (I) according to the first aspect, and optionally one or more of a liquid medium, a glycoprocessing protein, and a substance, and wherein the container is adapted such that fluorescence of the compound of formula (I) can be measured. The container may be a multi-well plate for use in a high throughput screening process. Optionally, one or more of the wells, preferably a plurality of the wells, contain a compound of formula (I) according to the first aspect, and optionally one or more of a liquid medium, a glycoprocessing protein, and a substance. The container may constitute all or part of the solid substrate as described herein.

The present invention provides in a sixth aspect a composition comprising a compound of formula (I) according to the first aspect and a protein selected from a glycosyltransferase protein and a glycoprocessing protein. The composition may further comprise a liquid medium. The compound of formula (I), the protein selected from a glycosyltransferase protein and a glycoprocessing protein, and the liquid medium may be as described herein.

The present invention provides in a sixth aspect a composition comprising a compound of formula (I) according to the first aspect and a glycosyltransferase protein. The composition may further comprise a liquid medium. The compound of formula (I), the glycosyltransferase protein, and the liquid medium may be as described herein.

The present invention provides in a sixth aspect a composition comprising a compound of formula (I) according to the first aspect and a glycoprocessing protein. The composition may further comprise a liquid medium. The compound of formula (I), the glycoprocessing protein, and the liquid medium may be as described herein.

In the second to the sixth aspect as described herein, the compound is of the first aspect as described herein. In the second to the sixth aspects, above, the $R_1$ in formula (I) may be selected from —OH, —OPO$_3$H, —OR$_4$, —NHR$_4$, R$_6$, wherein R$_4$ is selected from an optionally substituted mono or polysaccharide, -alkyl, -alkenyl, -alkynyl, and L-Z, where L is a linking agent and Z is a binding agent; and R$_6$ is an optionally substituted hydrocarbon group. In the second to the sixth aspects, above, the $R_1$ in formula (I) may be selected from —OH, —OPO$_3$H, —OR$_4$, —NHR$_4$, wherein R$_4$ is selected from an optionally substituted mono or polysaccharide, -alkyl, -alkenyl, -alkynyl, and L-Z, where L is a linking agent and Z is a binding agent. In the second to the sixth aspects, above, the $R_1$ in formula (I) may be R$_6$, wherein R$_6$ is an optionally substituted hydrocarbon group. The other groups in formula (I) may be as described herein.

Embodiments of the present invention will now be illustrated in the following non-limiting examples.

EXAMPLES

Example 1

A series of UDP-Gal derivatives 3a-d modified at the uracil base were synthesised using the method shown in FIG. 1 (Scheme 1). The key step in our synthesis is the Suzuki-Miyaura cross-coupling of 5-iodo UDP-Gal 2, which allowed the installation of a range of different aromatic or heteroaromatic substituents in position 5.

Methods
General.

All chemicals were obtained commercially and used as received unless stated otherwise. TLC was performed on precoated aluminium plates (Silica Gel 60 F254, Merck). Compounds were visualized by exposure to UV light. NMR spectra were recorded at 298 K on a Varian VXR 400 S spectrometer or on a Bruker Avance DPX-300 spectrometer. Chemical shifts (δ) are reported in ppm and referenced to methanol (δH 3.34, δC 49.50 for solutions in D2O). Coupling constants (J) are reported in Hz. Accurate electrospray ionisation mass spectra (HR ESI-MS) were obtained on a Finnigan MAT 900 XLT mass spectrometer at the EPSRC National Mass Spectrometry Service Centre, Swansea. Preparative chromatography was performed on a Biologic LP chromatography system equipped with a peristaltic pump and a 254 nm UV Optics Module under the following conditions:

Purification Method 1

Ion-pair chromatography was performed using Lichroprep RP-18 resin, gradient 0-10% MeCN against 0.05 M TEAB (triethylammoniumbicarbonate) over 480 mL, flow rate 5 mL/min. Product-containing fractions were combined and reduced to dryness. The residue was co-evaporated repeatedly with methanol to remove residual TEAB.

Purification Method 2

Anion exchange chromatography was performed using a Macro prep 25Q resin, gradient 0-100% 1M TEAB (pH 7.3) against $H_2O$ over 480 mL, flow rate 5 mL/min. Product-containing fractions were combined and reduced to dryness. The residue was co-evaporated repeatedly with methanol to remove residual TEAB.

5-Iodouridine

In a round bottom flask, uridine (1 g, 4.1 mmol) and iodine powder (1.15 g, 4.5 mmol) were dissolved in a mixture of $CHCl_3$ (55 ml) and 1M $HNO_3$ (10 ml). The reaction was heated at reflux (80° C.) for 5 h. Reaction progress was monitored by TLC (30% methanol in chloroform, Rf: 0.60; $Rf_{SM}$: 0.45). Upon cooling of the reaction mixture to 4° C., crystals of the title compound formed as colourless needles. The precipitate was collected by filtration and dried under vacuum overnight to provide 1.39 g (92%) of 5-iodouridine 1; δH (DMSO-d6, 300 MHz) 3.49-3.71 (2H, m, H-5'), 3.84-3.88 (1H, m, H-4'), 3.98 (1H, t, J=5.0 Hz, H-3'), 4.02 (1H, t, J=5.0 Hz, H-2'), 5.08 (1H, d, J=5.3 Hz, OH-3'), 5.27 (1H, t, J=4.7 Hz, OH-5'), 5.43 (1H, d, J=5.4 Hz, OH-2'), 5.71 (1H, d, J=4.6 Hz, H-1'), 8.48 (1H, s, H-6) 11.69 (1H, s, NH); δC (DMSO-d6, 300 MHz) 61.2 (C-5'), 70.3 (C-3'), 70.9 (C-5), 75.0 (C-2'), 85.7 (C-4'), 89.5 (C-1'), 146.0 (C-6), 152.5 (C-2), 162.9 (C-4). m/z (ESI) 388.0000 [M+NH4]$^+$, $C_9H_{15}IN_3O_6$ requires 388.0000.

5-Iodouridine-5'-Monophosphate (1)

5-Iodouridine (480 mg, 1.3 mmol) and proton sponge (1.67 g, 7.8 mmol) were dissolved in dry acetonitrile (30 mL) and the solution cooled to −5° C. under a nitrogen atmosphere. $POCl_3$ (485 μl, 5.2 mmol) was added dropwise. The orange-coloured reaction was stirred at −5° C. for 6 h, until TLC ($IPA/H_2O/NH_3$ 6:3:1; $R_f$ 0.31; $Rf_{SM}$ 0.71) indicated complete conversion. The reaction was quenched with 150 mL of ice-cold 0.2M TEAB buffer. The pale orange solution was stirred for 1 h at 0° C., and then allowed to warm to 25° C. The aqueous layer was washed with ethyl acetate (3×) and concentrated under reduced pressure. The crude residue was purified sequentially by purification methods 1 and 2. The triethylammonium salt of 1 was obtained as a colourless, glassy solid in 53% yield (307 mg). δH (400 MHz, $D_2O$) 4.00-4.15 (2H, m, H-5'), 4.23-4.27 (1H, m, H-4'), 4.30-4.32 (1H, m, H-3'), 4.39 (1H, t, J=5.4 Hz, H-2'), 5.93 (1H, d, J=5.9 Hz, H-1'), 16 8.27 (1H, s, H-6); δC (75.5 MHz, $D_2O$) δ4.5 (C-5', d, J=4.6 Hz), 69.2 (C-5), 70.5 (C-3'), 74.2 (C-2'), 84.4 (d, J=8.8 Hz, C-4'), 89.2 (C-1'), 146.7 (C-6), 152.4 (C-2), 164.0 (C-4); OP (121.5 MHz, $D_2O$) 7.6. m/z (ESI) 448.9255 [M−H]$^-$, $C_9H_{11}IN_2O_9P$ requires 448.9252.

5-Iodouridine-5'-Phosphoromorpholidate

5-Iodouridine-5'-monophosphate 1 (292 mg, 0.65 mmol) was dissolved in dry DMSO, co-evaporated (3×) with dry DMF, and finally dissolved in 0.5 mL of dry DMSO. Morpholine (400 μL, 4.6 mmol) was added and the reaction mixture was stirred at room temperature for 5 min. Dipyridyl disulfide (500 mg, 2.3 mmol) and triphenylphosphine (600 mg, 2.3 mmol) were added in 5 min intervals, and the reaction mixture was stirred for another 60 minutes at room temperature. Upon quenching of the reaction with 0.1 M NaI in acetone a precipitate formed. The supernatant was removed, and the precipitate was washed repeatedly with cold acetone, to give 354 mg (99% yield) of 5-Iodouridine-5'-phosphoromorpholidate as a white powder. This material was used in the next step without further purification. δH (400 MHz, $D_2O$) 3.04-3.16 (4H, m, H-Morpholine), 3.65-3.73 (4H, m, H-Morpholine), 4.00-4.15 (2H, m, H-5'), 4.24-4.26 (1H, m, H-4'), 4.27-4.32 (1H, m, H-3'), 4.36 (1H, t, J=5.4 Hz, H-2'), 5.94 (1H, d, J=5.8 Hz, H-1'), 8.17 (1H, s, H-6). δC (75.5 MHz, $D_2O$) 64.3 (morpholine), 63.3 (d, J=5.4 Hz, C-5'), 66.3 (morpholine), 67.8 (C-5), 68.6 (C-3'), 73.2 (C-2'), 83.0 (d, J=8.4 Hz, C-4'), 88.2 (C-1'), 145.0 (C-6), 153.3 (C-2), 161.9 (C-4); OP (121.5 MHz, $D_2O$) 11.0 ppm. m/z (ESI) 519.9968 [M+H]$^+$, $C_{13}H_{19}IN_3O_9P$ requires 519.9976.

5-Iodouridine-5'-diphosphate-α-D-galactose (2)

5-Iodouridine-5'-phosphoromorpholidate (107 mg, 0.21 mmol) was co-evaporated (3×) with dry pyridine (5 mL). Galactose-1-phosphate (tributylamine salt, 326 mg, 0.55 mmol) was 17 added, and the mixture was further co-evaporated (3×) with pyridine (5 mL). Under a nitrogen atmosphere, the dry residue was dissolved in dry DMF (2 mL) and a 0.05M solution of tetrazole (80 mg, 1.14 mmol) in dry acetonitrile was added. The reaction was stirred at room temperature for 5 h, by which time the reaction had reached completion. All solvents were removed under reduced pressure, and the crude residue was purified sequentially by purification methods 1 and 2. The title compound 2 was obtained in its triethylammonium salt form as a colourless, glassy solid in 42% yield (60 mg). δH (400 MHz, $D_2O$) 3.70-3.76 (2H, m, H-6''), 3.77-3.82 (1H, m, H-2''), 3.92 (1H, dd, J=3.3 and 10.1 Hz, H-3''), 4.01 (1H, d, J=3.7 Hz, H-4''), 4.16-4.19 (1H, m, H-5''), 4.20-4.23 (2H, m, H-5'), 4.25-4.28 (1H, m, H-4'), 4.33-4.39 (2H, m, H-2', H-3'), 5.64 (1H, dd, J=3.6 and 6.6 Hz, H-1''), 5.93 (1H, d, J=5.9 Hz, H-1'), 8.25 (1H, s, H-6); δC (75.5 MHz, $D_2O$) 59.6, 61.8, 65.8 (d, J=3.0 Hz), 69.3, 69.8, 70.0, 70.4, 72.7, 74.6, 84.2 (d, J=5.3 Hz), 89.3, 96.6 (d, J=3.8 Hz), 146.6, 152.4, 164.1; δP (121.5 MHz, $D_2O$) −9.21 (d, J=21.2 Hz), −7.71 (d, J=21.2 Hz). m/z (ESI) 709.9863 [M+NH4]$^+$, $C_{15}H_{27}N_3O_{17}P_2I$ requires 709.9855.

General Method for the Preparation of 5-(hetero)aryl UDP-α-D-galactose derivatives 3a-d A 2-necked round bottom flask with 2 (1 eq.), $Cs_2CO_3$ (2 eq.) and (hetero)arylboronic acid (1.5 eq.) was purged with N$_2$. TPPTS (0.0625 eq.), Na$_2$Cl$_4$Pd (0.025 eq.) and degassed H$_2$O (4 mL) were added and the reaction was stirred under N$_2$ for 1 h at 50° C. Upon completion, the reaction was cooled to room temperature and the pH was adjusted to 7 with 1% HCl. The suspension was filtered through a membrane filter (0.45 μm). The filter was washed with H$_2$O and the combined filtrates were evaporated under reduced pressure. The residue was purified consecutively by anion-exchange chromatography (MacroPrep 25Q; gradient: H$_2$O against 0-100% TEAB (1M); total volume: 480 mL; flow rate: 5 mL/min) and ion-pair chromatography (Lichroprep RP-18, equilibrated with 0.05 M TEAB; gradient: TEAB (0.05M) against 0-10% MeCN; total volume: 480 mL; flow rate: 5 mL/min). Product-containing fractions were combined and reduced to dryness, and the residue was co-evaporated repeatedly with methanol.

5-Phenyl UDP-α-D-galactose (3a)

The triethylammonium salt of the title compound was obtained as a glassy solid in 66% yield (14.8 mg) from 2 (16 mg, 23 μmol) and phenylboronic acid according to the general method. δH (400 MHz, D$_2$O) 3.64-3.72 (2H, m, H-6"), 3.75 (1H, dt, J=2.8 and 8.4 Hz, H-2"), 3.87 (1H, dd, J=3.2 and 10.3 Hz, H-3"), 3.98 (1H, d, J=3.2 Hz, H-4"), 4.13 (1H, t, J=6.2 Hz, H-5"), 4.17-4.21 (2H, m, H-5'), 4.28-4.32 (1H, m, H-4'), 4.39 (1H, t, J=4.6 Hz, H-3'), 4.48 (1H, t, J=5.5 Hz, H-2'), 5.59 (1H, dd, J=3.5 and 7.2 Hz, H-1"), 6.04 (1H, d, J=6.0 Hz, H-1'), 7.40-7.56 (5H, m, Ph), 7.88 (1H, s, H-6); δC (125 MHz, D$_2$O) 61.7 (C-6"), 65.9 (C-5'), 69.0 (d, $J_{C,P}$=7.9 Hz, C-2"), 69.7 (C-4"), 69.9 (C-3"), 70.6 (C-3'), 72.6 (C-5"), 74.1 (C-2'), 84.1 (d, JC,P=9.4 Hz, C-4'), 89.1 (C-1'), 96.5 (d, $J_{C,P}$=6.0 Hz, C-1"), 117.0 (C-5), 129.0 (iPh), 129.3, 129.4 (oPh, mPh), 132.3 (pPh), 139.1 (C-6), 152.2 (C-2), 165.6 (C-4); SP (121 MHz, D$_2$O) −11.4 (d, $J_{P,P}$=20.6 Hz), −12.8 (d, $J_{P,P}$=20.6 Hz). m/z (ESI) 660.1199 [M+NH$_4$]$^+$, C$_{21}$H$_{32}$N$_3$O$_{17}$P$_2$ requires 660.1201.

5-(4-Methoxyphenyl)-UDP-α-D-galactose (3b)

The triethylammonium salt of the title compound was obtained as a glassy solid in 75% yield (9.8 mg) from 2 (9.7 mg, 14 μmol) and 4-methoxyphenylboronic acid according to the general method. δH (400 MHz, D$_2$O) 3.64-3.70 (2H, m, H-6"), 3.75 (1H, dt, J=3.0 and 11.0 Hz, H-2"), 3.86 (1H, dd, J=3.5 and 10.0 Hz, H-3"), 3.87 (3H, s, MeO), 3.97 (1H, d, J=3.2 Hz, H-4"), 4.12 (1H, dd, J=4.6 and 7.6 Hz, H-5"), 4.17-4.21 (2H, m, H-5'), 4.28-4.32 (1H, m, H-4'), 4.39 (1H, dd, J=3.5 and 5.0 Hz, H-3'), 4.47 (1H, t, J=5.7 Hz, H-2'), 5.59 (1H, dd, J=3.6 and 7.0 Hz, H-1"), 6.04 (1H, d, J=6.0 Hz, H-1'), 7.07, 7.49 (4H, 2d, J=8.9 and 8.9 Hz, oPh, mPh), 7.84 (1H, s, H-6); δC (125 MHz, D$_2$O) 56.0 (MeO), 61.8 (C-6"), 66.1 (d, JC,P=6.8 Hz, C-5'), 69.1 (d, JC,P=7.8 Hz, C-2"), 69.2 (C-3"), 70.0 (C-4"), 70.7 (C-3'), 72.7 (C-5"), 74.1 (C-2'), 84.3 (d, J=10.1 Hz, C-4'), 89.1 (C-1'), 96.6 (d, $J_{C,P}$=7.0 Hz, C-1"), 114.9 (mPh), 116.7 (C-5), 125.1 (iPh), 130.9 (oPh), 138.5 (C-6), 152.4 (C-2), 159.6 (pPh), 165.8 (C-4); SP (121.5 MHz, D$_2$O) −11.3 (d, $J_{P,P}$=20.6 Hz), −12.8 (d, $J_{P,P}$=20.6 Hz). m/z (ESI) 690.1314 [M+NH$_4$]$^+$, C$_{22}$H$_{34}$N$_3$O$_{18}$P$_2$ requires 690.1307.

5-(2-Furyl)-UDP-α-D-galactose (3c)

The triethylammonium salt of the title compound was obtained as a glassy solid in 52% yield (4.9 mg) from 2 (7.2 mg, 10.4 μmol) and furan-2-boronic acid according to the general method. δH (400 MHz, D$_2$O) 3.64-3.74 (2H, m, H-6"), 3.77 (1H, dt, J=3.4 and 8.4 Hz, H-2"), 3.88 (1H, dd, J=3.3 and 10.3 Hz, H-3"), 3.97 (1H, d, J=3.2 Hz, H-4"), 4.14 (1H, dd, J=4.6 and 7.6 Hz, H-5"), 4.22-4.27 (2H, m, H-5'), 4.30-4.34 (1H, m, H-4'), 4.43 (1H, t, J=4.6 Hz, H-3'), 4.49 (1H, t, J=5.4 Hz, H-2'), 5.63 (1H, q, J=3.6 Hz, H-1"), 6.06 (1H, d, J=5.6 Hz, H1'), 6.53 (1H, dd, J=1.8 and 3.4 Hz, fur3), 6.90 (1H, d, J=3.4 Hz, fur4), 7.59 (1H, d, J=1.8 Hz, fur2), 8.24 (1H, s, H-6); δC (125 MHz, D$_2$O) 61.8 (C-6"), 66.0 (d, JC,P=5.0 Hz, C-5'), 69.1 (d, JC,P=8.2 Hz, C-2"), 69.8 (C-3"), 70.0 (C-4"), 70.6 (C-3'), 72.7 (C-5"), 74.3 (C-2'), 84.2 (d, JC,P=10.1 Hz, C-4'), 89.2 (C-1'), 96.6 (d, $J_{C,P}$=5.6 Hz, C-1"), 108.4 (C-5), 109.6 (fur4), 112.2 (fur3), 136.2 (C-6), 143.4 (fur2), 146.0 (fur1), 151.7 (C-2), 163.4 (C-4); δP (121 MHz, D$_2$O) −11.4, −12.7. m/z (ESI) 650.0990 [M+NH$_4$]$^+$, C$_{19}$H$_{30}$N$_3$O$_{18}$P$_2$ requires 650.0994.

5-(5-Formylthien-2-yl)-UDP-α-D-galactose (3d)

The triethylammonium salt of the title compound was obtained as a glassy solid in 56% yield (10.0 mg) from 2 (8.6 mg, 12.4 μmol) and 5-formylthienyl-2-boronic acid according to the general method. δH (400 MHz, D$_2$O) 3.66-3.72 (2H, m, H-6"), 3.72-3.76 (1H, m, H-2"), 3.84 (1H, dd, J=3.2 and 10.2 Hz, H-3"), 3.95 (1H, d, J=3.0 Hz, H-4"), 4.10-4.13 (1H, m, H-5"), 4.28-4.31 (2H, m, H-5'), 4.32-4.34 (1H, m, H-4'), 4.40-4.48 (2H, 2t, J=5.1 and 5.1 Hz, H-2', H-3'), 5.62 (1H, dd, J=3.4 and 7.1 Hz, H-1"), 6.04 (1H, d, J=4.9 Hz, H-1'), 7.74 (1H, d, J=4.2 Hz, Th), 8.01 (1H, d, J=4.1 Hz, Th), 8.46 (1H, s, H-6), 9.79 (1H, s, CHO); δC (125 MHz, D$_2$O) 61.7, 65.7 (d, JC,P=4.6 Hz), 69.0 (d, $J_{C,P}$=6.7 Hz), 69.7, 70.0, 70.3, 72.6, 74.9, 84.3 (d, $J_{C,P}$=7.3 Hz), 89.7, 96.4 (d, $J_{C,P}$=5.4 Hz), 109.6, 126.0, 139.2, 140.3, 142.0, 144.8, 151.2, 163.5, 187.8; δP (121.5 MHz, D$_2$O) −11.2 (d, $J_{P,P}$=22.5 Hz), −12.7 (d, $J_{P,P}$=21.2 Hz). m/z (ESI) 675.0305 [M−H]$^-$, C$_{20}$H$_{25}$N$_2$O$_{18}$P$_2$S requires 675.0304.

In contrast to the practically non-fluorescent parent UDP-Gal, the resulting 5-(hetero)aryl UDP-Gal derivatives 3a-d are fluorescence emitters, and their fluorescence properties can be modulated by the nature of the 5-substituent (Table 1). Crucially, while the phenyl- and furyl-substituted derivatives 3a-c showed only moderate to weak fluorescence, thienyl derivative 3d was much more strongly fluorescent. The quantum yield of 3d is 25-fold greater than that of 3a, and almost 6000-fold greater than the quantum yield of the parent UDP-Gal (Table 1). We anticipated that with these fluorescence characteristics, 3d might be a suitable fluorophore for a fluorescence based GalT ligand-displacement assay, provided that 3d was recognised as a donor analogue by the target GalTs. In order to assess the influence of the additional substituent in position 5 on GalT recognition and binding, we carried out enzymological studies with donor analogues 3a-d and a representative bovine GalT (Table 1).

Example 2

Biochemistry

Proteins were expressed and purified as described in Sujino, K.; Uchiyama, T.; Hindsgaul, O; Seto, N. O. L.; Wakarchuk, W. W. & Palcic, M. M. *Enzymatic Synthesis of Oligosaccharide Analogues: Evaluation of UDP-Gal Analogues as Donors for Three Retaining α-Galactosyltransferases.* J. Am. Chem. Soc. 122, 261-1269 (2000); Rich, J. R.; Szpacenko, A.; Palcic, M. M. & Bundle, D. R. *Glycosyltransferase-Catalyzed Synthesis of Thiooligosaccharides.* Angew. Chem. Int. Ed. 43, 613-615 (2004) and Namdjou, D. J.; Chen, H. M.; Vinogradov, E.; Brochu, D.; Withers, S. G. & Wakarchuk, W. W. *A beta-1,4-galactosyltransferase from Helicobacter pylori is an efficient and versatile biocatalyst displaying a novel activity for thioglycoside synthesis.*

ChemBioChem 9, 1632-1640 (2008). For donor kinetics, UDP-Gal or 3a-d (0.6-16 μM), GalT (26 μU), acceptor and MnCl$_2$ (20 mM) in MOPS buffer (35 mM, pH=7.2) were incubated for 10 minutes at 37° C. (total volume 100 μL, all concentrations are final concentrations). The reactions were stopped by cooling in dry ice. Samples were analysed immediately by HPLC on a PerkinElmer Series 200 machine equipped with a Supelcosil LC-18-T column (5 μm, 25 cm×4.6 mm), a column oven (set to 30° C.), and a diode array detector. Each sample (injection volume 40 μL) was eluted at 1.5 mL/min with a gradient of methanol (10-30%) against 0.5 M phosphate buffer (adjusted to pH 8 with triethylamine). The depletion of donor (UDP-Gal, 3a-d) and the formation of nucleoside diphosphate, the secondary product of the glycosylation reaction, were monitored at 430 nm. Km and vmax values were determined by fitting data points to a Michaelis-Menten curve using GraFit 5.0.10. Control experiments carried out in the absence of (i) enzyme and (ii) acceptor showed no significant degree of chemical hydrolysis.

Quantum Yields

UDP-Gal derivatives 3a-d were serially diluted in H$_2$O, and UV absorbance and fluorescence emission (with $\lambda_{max}$ absorbance=$\lambda_{ex}$ fluorescence) were recorded for all samples. To determine quantum yields, for each absorbance and fluorescence spectrum the area under the curve (AUC) was calculated by numerical integration, applying the mid-point rule. For each compound, AUC$_{abs}$ and AUC$_{fluo}$ were then plotted over compound concentration according to AUC$_{abs}$=A×[conc]+B (equation 1) and AUC$_{fluo}$=A'×[conc]+B' (equation 2). From these linear plots, the gradients A and A' were extracted, and for each compound the specific quantum yield $\phi_s$, under these experimental conditions, was calculated as the ratio A'/A. Quantum yields determined with this protocol for two reference compounds, 2-aminopyridine and L-tryptophan, were in agreement with literature values (2-aminopyridine: 0.60; L-tryptophan: 0.14; J. R. Lakowicz, *Principles of Fluorescence Spectroscopy*, 3$^{rd}$ Edition, Springer Verlag, 2006). The quantum yields for reference compounds were used to calculate the general quantum yield $\phi_g$ for each compound 3a-d, according to $\phi_g=\phi_{ref}\times(A'/A)/(A'/A)_{ref}$.

We found that although the turnover of 3a-d was slower than for UDP-Gal, the Michaelis-Menten constant of the base-modified analogues was of a similar order of magnitude as for UDP-Gal. These results suggested that the additional substituent in position 5 does not interfere significantly with binding of these donor analogues, although it does slow down donor utilisation. Because of its strong binding affinity and surprisingly pronounced fluorescence, the thienyl-substituted derivative 3d is the most suitable fluorophore for use in a GalT ligand displacement assay. Its use in an assay is shown below.

TABLE 1

| Cmpd | R | Quantum yield | B. taurus α-1,3-GalT | |
|---|---|---|---|---|
| | | | K$_m$ (μM) | k$_{cat}$ (s$^{-1}$) |
| UDP-Gal | H | 0.045 × 10$^{-3}$ | 118 ± 14 | 0.98 |
| 3a | phenyl | <0.01 | 96 ± 8 | 2.1 × 10$^{-3}$ |
| 3b | 4-MeO-ph | 0.024 | 82 ± 11 | 4.0 × 10$^{-3}$ |
| 3c | 2-furanyl | 0.04 | 69 ± 13 | 4.4 × 10$^{-3}$ |
| 3d | 5-(2-formyl)thienyl | 0.26 | 13 ± 1 | 1.9 × 10$^{-3}$ |

Figure 1A:
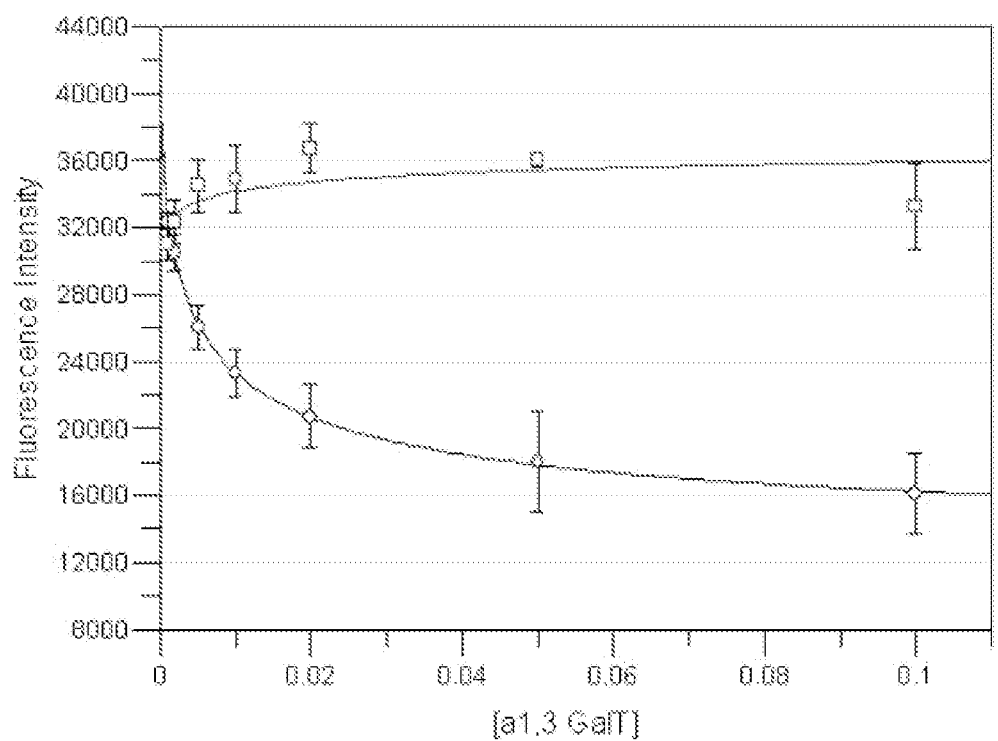
FIG. 1a shows the fluorescence emission of fluorophore 3d (see Examples) upon titration with α-1.3-GalT in the presence (blue) or absence (red) of MnCl$_2$. Assay conditions: 200 nM ligand, 50 mM Tris buffer (pH=7), increasing concentration of enzyme, 30° C., 15 min.
Figure 1B:
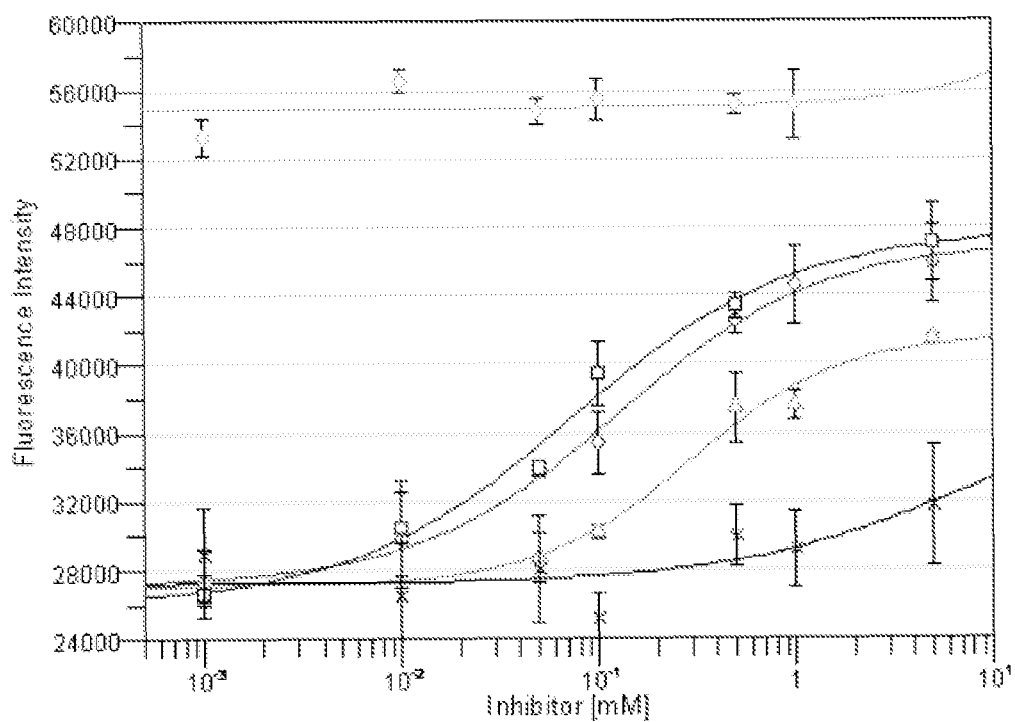
FIG. 1b shows the titration of 3d and α-1.3-GalT with UDP (blue), UDP-Gal (red), UMP (green) and uridine (black), control experiment without enzyme in grey.

The fluorescence emission of a given fluorophore is influenced by its microenvironment, although different fluorophores vary their fluorescence emissions to different extents on changing microenvironment. In order to test whether and how the fluorescence of 3d changes on binding to a GT, we first carried out titration experiments with 3d and the *B. taurus* α-1.3-GalT. We found that the fluorescence of 3d is quenched in the presence of enzyme in a concentration-dependent manner (FIG. 1a). To assess the specificity of this effect, we next performed several control experiments. The *B. taurus* a-1.3-GalT was found to bind to the compound of the present invention to a much greater extent when a divalent metal, e.g. Mn$^{2+}$ was present. In the absence of Mn$^{2+}$ little or no fluorescence quenching was observed upon titration of fluorophore 3d with α-1.3-GalT (FIG. 1a). This result strongly suggested that binding of 3d occurs specifically at the donor binding site of α-1.3-GalT, with the implication that the observed fluorescence quenching effect also is specific and not due to e.g. non specific binding of 3d on the protein surface. This interpretation was corroborated by the finding that the fluorescence of 3d could be restored by titration with non-fluorescent, competitive α-1.3-GalT ligands, including UDP-Gal and UDP (FIG. 1b). These results further confirmed the specificity of the binding, and concomitant fluorescence quenching, of 3d. Importantly, these experiments also allowed the determination of IC50 values for these known GalT ligands. The order of potency observed for UDP-Gal, UDP, UMP and uridine was in agreement, qualitatively and quantitatively, with literature data for inhibition of GalTs by these ligands, which suggested that this assay set-up is suitable for inhibitor screening.

Microplate Assays

Fluorescence intensity measurements with 3d were carried out in black NUNC F96 MicroWell polystyrene plates on a BMG labtech PolarStar microplate reader equipped with a 350±5 nm excitation filter and a 430±5 nm emission filter. The number of flashes per wells was set to 50 (gain: 2240; position delay: 0.2 s). Prior to readings, plates were incubated, with shaking, for 10 min at 30° C. (double orbital, shaking width 4 mm, 10 seconds). Results were visualised with BMG labtech data analysis software Mars 1.10 and analysed with GraFit version 5.0.10.

Assay Protocol

Samples were pipetted into the requisite wells of a black NUNC 96-well plate as shown in tables E1-E3, at the end of the description. Key: B—Tris/HCl buffer (50 mM, pH 7; 40 μL); F—fluorophore 3d (200 nM in Tris/HCl buffer; 40 μL); M—MnCl$_2$ (10 mM in Tris/HCl buffer; 80 μL); E—galactosyltransferase (in Tris/HCl buffer; 40 μL); I—inhibitor (in Tris/HCl buffer; 40 μL). Total volume/well: 200 μL. All experiments were carried out in triplicate, unless indicated otherwise.

Example 3

Figure 2:
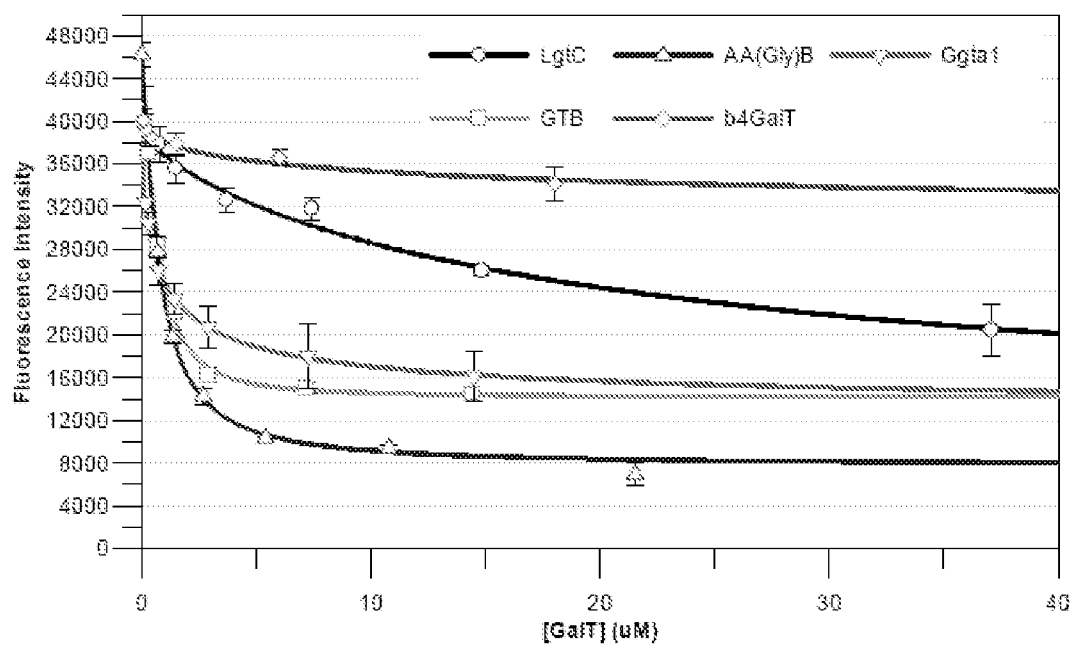
FIG. 2 shows the titration of 3d with other GTs, including β4GalT (*H. pylori*), LgtC (*N. meningitidis*), Ggta1 (*B. taurus*), GTB (*H. sapiens*), and AA(Gly)B GTB mutant (*H. sapiens*).

To assess the generality of this new GT assay principle, we next repeated the above experiments with another four GalTs, including mammalian and bacterial enzymes with different acceptor specificities and reaction mechanisms. Significantly, with all of these enzymes we consistently observed a strong fluorescence quenching effect for 3d (FIG. 2). The experimental protocol was the same as in Example 2. The amino acid sequences for four GalTs used in the experiment, i.e. LgtC (*N. meningitidis*), Ggta1 (*B. taurus*), GTB (*H. sapiens*) and AA(Gly)B GTB mutant (*H. sapiens*) or references where the sequence listings can be found are given above. The amino acid sequence for β4GalT (*H. pylori*) can be found above and in the following reference: Endo, T., Koizumi, S., Tabata, K. & Ozaki, A. *Glycobiology* 10, 809-813 (2000).

Example 4

Figure 3A:
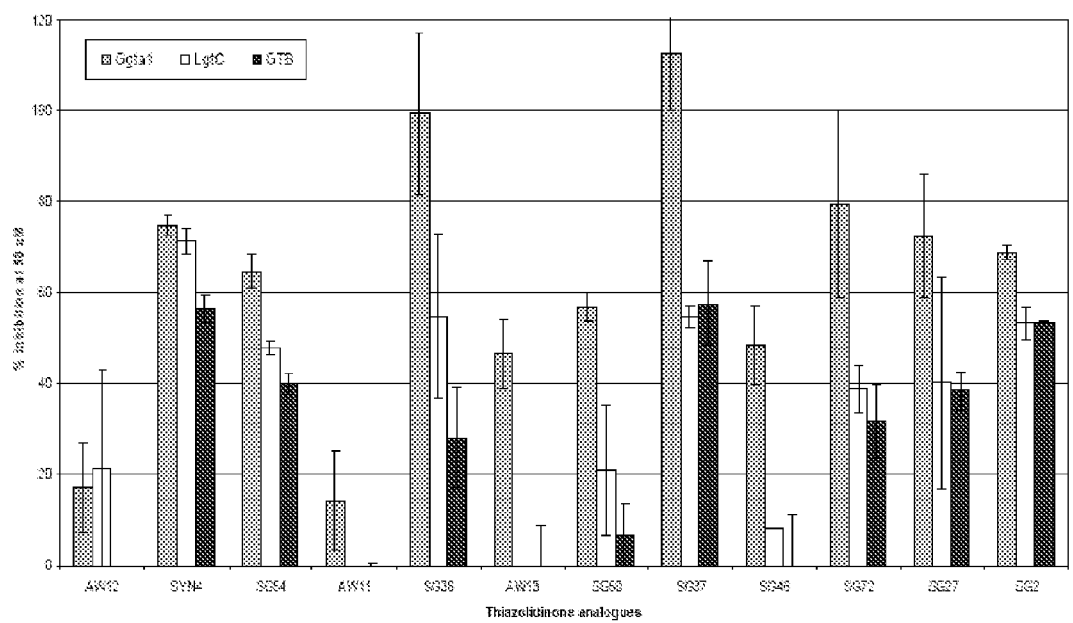
FIG. 3a shows the screening of 12 inhibitor candidates in parallel against three different GalTs, LgtC (*N. meningitidis*), Ggta1 (*B. taurus*), GTB (*H. sapiens*), using fluorophore 3d.

With a general fluorophore for different GalTs in hand, we set out to investigate the suitability of this fluorophore for the identification, and selectivity profiling, of new GalT inhibitors. In a proof-of-concept experiment, we screened a small library of drug-like inhibitor candidates in parallel against three different enzymes (FIG. 3a). For this initial screen, we selected a structurally diverse set of thiazolidinones as inhibitor candidates, as thiazolidinones had previously been reported as inhibitors for other GTs. Inhibitor candidates, at a concentration of 50 mM, were co-incubated on a single microplate with the GalTs Ggta1, GTB and LgtC and fluorophore 3d. As expected, the competitive displacement of 3d from the GalT donor binding site resulted in an increase in fluorescence. To quantify the displacement of fluorophore by individual inhibitors, the fluorescence increase observed for the natural donor UDP-Gal was used as a reference.

Protocol for Library Screening

Samples were pipetted into individual wells of a black NUNC 96-well plate as shown in table E4, at the end of the description. Key: M—$MnCl_2$ (10 mM in Tris/HCl buffer; 80 µL); F—fluorophore 3d (200 nM in Tris/HCl buffer; 40 µL); T1-T12—thiazolidinone inhibitors (50 µM in Tris/HCl buffer; 40 µL); U—UDP-Gal (5 mM in Tris/HCl buffer; 40 µL). Total volume/well: 160 µL. The microplate was incubated for 10 minutes at 30° C. and the fluorescence emission was recorded ($1^{st}$ reading). To the requisite wells were then added 40 µL of Tris/HCl buffer (B), α-1.3-GalT (E1), LgtC (E2) or GTB (E3), as shown in table E5, at the end of the description. The microplate was incubated for another 10 minutes at 30° C. and a second fluorescence emission reading was taken ($2^{nd}$ reading).

The relative increase in fluorescence from $1^{st}$ to $2^{nd}$ reading was attributed to the degree of binding of 3d at the individual GalT in the presence or absence of inhibitor. Thus, for all wells, fluorescence intensity after GalT addition ($2^{nd}$ reading) was subtracted from fluorescence intensity before GalT addition ($1^{st}$ reading) to give ΔFI. For each GalT the maximum (no displacement of 3d, e.g. wells A1 & A2) and minimum (displacement of 3d by UDP-Gal, e.g. wells A3 & A4) change in fluorescence was calculated and denoted as $\Delta FI_{max}$ and $\Delta FI_{min}$. The change in fluorescence in the presence of individual thiazolidinones ($\Delta FI_T$, wells C1-H12) was used to quantify the displacement of 3d from each GalT, by each thiazolidinone, relative to the displacement of 3d by UDP-Gal from the same enzyme, according to the following equation: % inhibition=$(1-\Delta FI_T/(\Delta FI_{max}-\Delta FI_{min}))\times 100\%$.

Figure 3B:
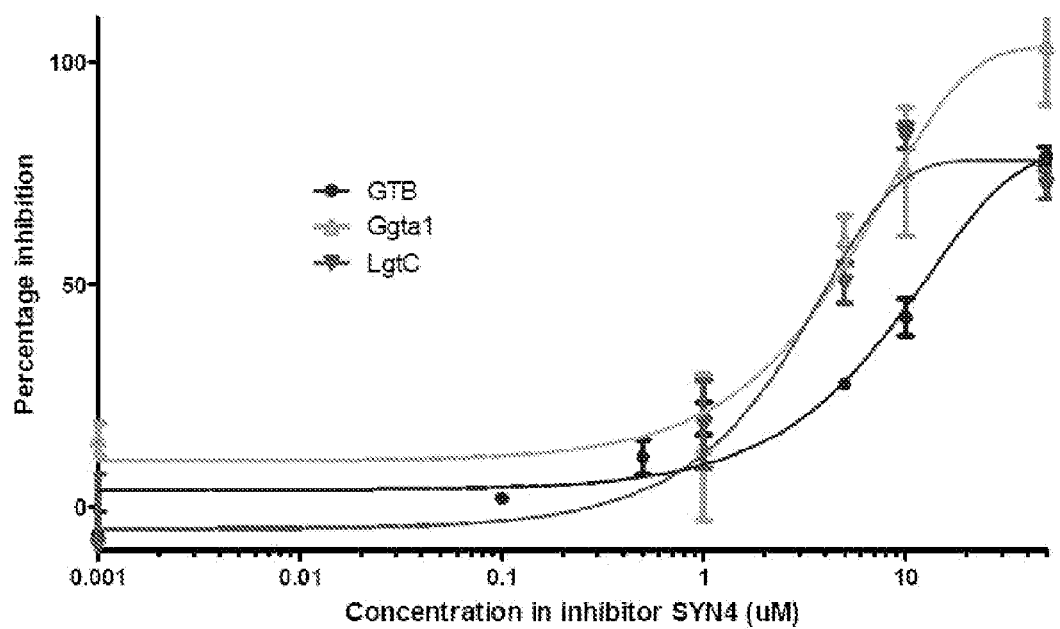
FIG. 3b shows the Inhibition of GalTs GTB, LgtC and Ggta1 by thiazolidinone inhibitor SYN4.

Using this procedure, we were able to establish a rank order for inhibitor candidates according to their binding affinity and to assess, at the same time, their GalT selectivity profile. To validate this approach, we determined complete binding curves with all three GalTs for the representative thiazolidinone inhibitor SYN4 (FIG. 3b). The experimental protocol used was the same as in Example 2.

The IC50 values extracted from these binding curves suggest a slightly greater affinity of SYN4 for Ggta1 and LgtC than for GTB and, significantly, are in keeping with the selectivity profile observed for SYN4 in the single-concentration screen.

Example 5

Figure 4:
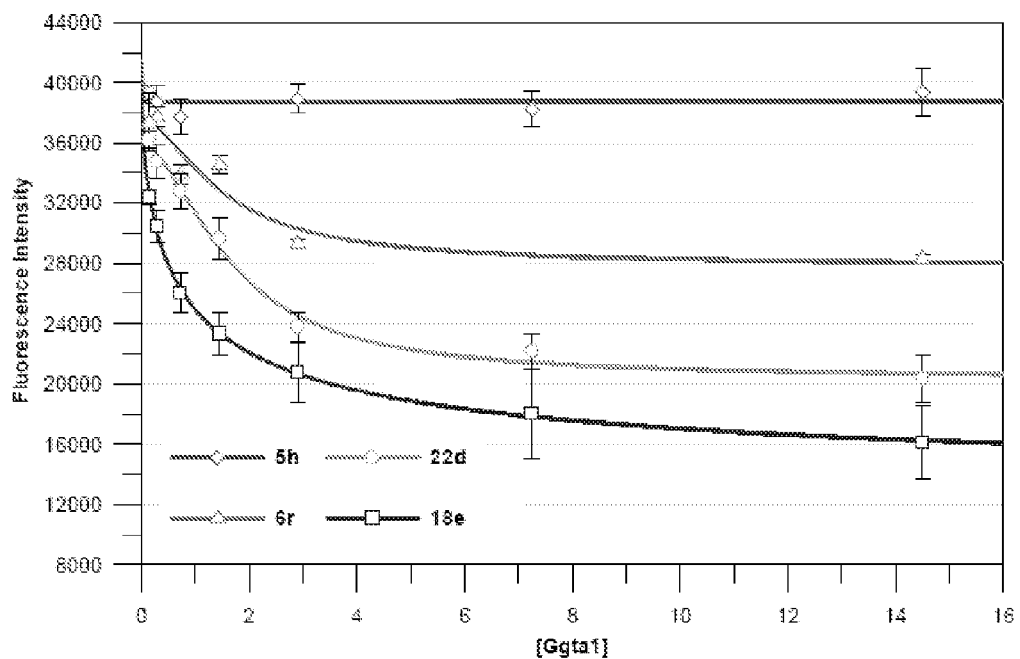
FIG. 4 shows the variation in fluorescence upon incubation of 3d (numbered 18e in FIG. 4) and analogues 5h (nucleoside), 6r (nucleotide), 22d (nucleoside diphosphate) with various concentrations of Ggta1.

We also carried out an experiment on 3d (numbered 18e in FIG. 4) and different analogues of 3d, namely the nucleoside 5h, the nucleotide 6r and nucleoside diphosphate 22d, to show their variation in fluorescence on binding to Ggta1. Results are shown in FIG. 4.

The synthesis of 5h, 6r and 22d are shown below. The protocol for the microplate/fluorescence experiments was the same as in Example 2.

5-(5-Formylthien-2-yl)-uridine (5h)

A 2-necked round bottom flask with 5-iodouridine (100 mg, 270 µmol), 5-formyl-2-thiopheneboronic acid (1.5 eq) and $Cs_2CO_3$ (2 eq.) was purged with $N_2$. Upon addition of TPPTS (0.0625 eq.), $Na_2Cl_4Pd$ (0.025 eq.) and degassed $H_2O$ (5 mL) the mixture turned orange in colour. The reaction was stirred under $N_2$ for 1 h at 60° C., turning brown/black. Once the starting material was fully consumed, the reaction mixture was cooled to room temperature. The pH was adjusted to 7 with HCl 1% and the reaction mixture was filtered through Celite. The solvents were removed to give a colourless powder. After purification, the title compound was obtained in 23% yield (16 mg). $\delta_H$ (400 MHz, DMSO-$d_6$) 3.65-3.85 (2H, m, H-5'), 3.90-3.95 (1H, m, H-4'), 4.02-4.17 (2H, m, H-2' and H-3'), 5.11 (1H, d, J=5.9 Hz, OH-3'), 5.54 (1H, d, J=5.0 Hz, OH-2'), 5.60 (1H, t, J=4.3 Hz, OH-5'), 5.80 (1H, d, J=3.0 Hz, H-1'), 7.56 (1H, d, J=4.1 Hz, Th), 7.93 (1H, d, J=4.0 Hz, Th), 9.02 (1H, s, H-6), 9.87 (1H, s, CHO), 11.9 (1H, s, NH); $\delta_C$ (75.5 MHz, DMSO-$d_6$) 59.6 (C-5'), 68.7 (C-3'), 74.5 (C-2'), 84.4 (C-4'), 89.5 (C-1'), 106.9 (C-5), 122.9, 137.3, 138.7, 141.6, 144.4, 149.4 (C-2+C-6+C—Th), 161.4 (C-4), 184.3 (CHO). m/z (ESI) 353.0448 [M–H]$^-$, $C_{14}H_{13}O_7N_2S$ requires 353.0449.

5-(5-Formylthien-2-yl)-UMP (6r)

A 2-necked round bottom flask with 5-iodouridine-5'-monophosphate 4 (10 mg, 22.2 µmol, 1 eq.), $Cs_2CO_3$ (2 eq.) and arylboronic acid (1.5 eq.) was purged with $N_2$. TPPTS (0.0625 eq.), $Na_2Cl_4Pd$ (0.025 eq.) and degassed $H_2O$ (4 mL) were added, and the reaction was stirred under $N_2$ for 1 h at 60° C. Upon completion, the reaction was cooled to room temperature, and the pH was adjusted to 7 with 1% HCl. The black suspension was concentrated unter reduced pressure, and the residue was taken up in MeOH. The methanolic suspension was filtered through Celite, and the residue was washed with methanol. The combined filtrates were evaporated under reduced pressure. After chromatographic purification of the residue, the title compound was obtained in its triethylammonium salt form as a glassy solid in 61% yield (8.6 mg). $\delta_H$ (400 MHz, $D_2O$) 4.12-4.20 (2H, m, H-5'), 4.29-4.31 (1H, m, H-4'), 4.38 (1H, t, J=4.7 Hz, H-3'), 4.45 (1H, t, J=5.0 Hz, H-2'), 5.98 (1H, d, J=5.0 Hz, H-1'), 7.66 (1H, d, J=4.0 Hz, Th), 7.94 (1H, d, J=4.0 Hz, Th), 8.38 (1H, s, H-6) 9.75 (1H, s, CHO); $\delta_C$ (75.5 MHz, $D_2O$) 64.7 (d, $J_{C,P}$=4.5 Hz, C-5'), 70.4 (C-3'), 74.9 (C-2'), 84.4 (C-4'), 89.7 (C-1'), 110.0, 125.9, 139.1, 140.1, 142.0 (C5+C—Th), 144.9 (C-6), 152.7 (C-2), 163.5 (C-4), 187.8 (CHO); $\delta_P$ (121.5 MHz, $D_2O$) 7.6. m/z (ESI) 433.0107 [M–H]$^-$, $C_{14}H_{14}O_{10}N_2PS$ requires 433.0112.

5-(5-Formylthien-2-yl)-UDP (22d)

A 2-necked round bottom flask with 5-iodouridine-diphosphate (14.0 mg, 26.4 µmol, 1 eq.), $Cs_2CO_3$ (2 eq.) and arylboronic acid (1.5 eq.) was purged with $N_2$. TPPTS (0.0625 eq.), $Na_2Cl_4Pd$ (0.025 eq.) and degassed $H_2O$ (4 mL) were added and the reaction was stirred under $N_2$ for 1 h at 50° C. Upon completion, the reaction was cooled to room temperature and the pH was adjusted to 7 with 1% HCl. The black suspension was filtered through a membrane filter (0.45 µm).

The filter was washed with $H_2O$ and the combined filtrates were evaporated under reduced pressure. After chromatographic purification, the title compound was obtained in its triethylammonium salt form as a glassy solid in 77% yield (8.2 mg). $\delta_H$ (400 MHz, $D_2O$) 4.26-4.32 (2H, m, H-5'), 4.32-4.35 (1H, m, H-4'), 4.43-4.50 (2H, m, H-2' and H-3'), 6.01-6.07 (1H, m, H-1'), 7.71-7.75 (1H, m, Th), 7.99-8.01 (1H, m, Th), 8.45 (1H, s, CHO); $\delta_C$ (75.5 MHz, $D_2O$) 65.5 (C-5'), 70.2 (C-3'), 74.9 (C-2'), 84.2 (C-4'), 89.7 (C-1'), 109.3 (C-5), 125.8, 138.9, 140.3, 142.0, 144.8 (C-6+C—Th), 151.1 (C-2), 163.3 (C-4), 187.8 (CHO); $\delta_P$ (121 MHz, $D_2O$) −6.5 (d, $J_{P,P}$=23.1 Hz), −11.0 (d, $J_{P,P}$=23.1 Hz). m/z (ESI) 512.9776 [M−H]$^-$, $C_{14}H_{15}O_{13}N_2P_2S_1$ requires 512.9776.

These results show that 3d, 6r and 22d all varied their intensity of luminescence with Ggta1, and all would be suitable for use in the method of the present invention.

Taken together, results from this screen show that the method of the present invention allows the reliable discrimination between low- and high-affinity GalT binders. Our protocol therefore offers an extremely rapid and simple method for the identification and target profiling of novel, drug-like GalT inhibitors.

Example 6

Figure 5:
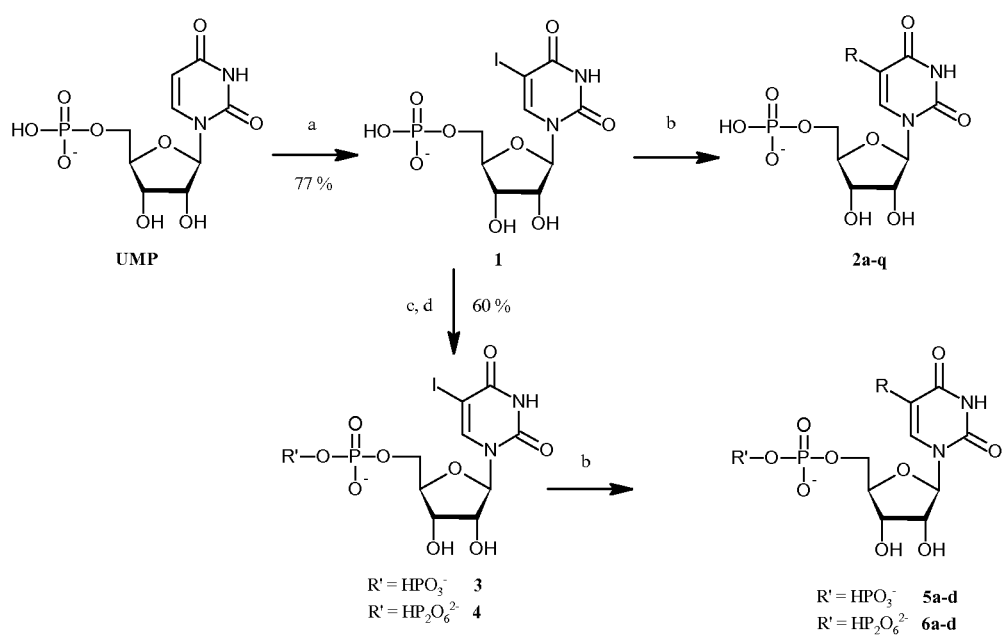
FIG. 5 shows a scheme for the synthesis of the compounds tested in Example 6.

The following Example describes the synthesis and spectrophysical properties for a range of uridine monophosphate derivatives. The derivatives were synthesised as shown in the outline scheme of FIG. 5, with the nomenclature in this Example for the compounds being the same as shown in FIG. 5.

Experimental

All chemicals were obtained commercially and used as received unless stated otherwise. TLC was performed on precoated aluminium plates (Silica Gel 60 F254, Merck). Compounds were visualized by exposure to UV light (254 and 365 nm). NMR spectra were recorded at 298 K on a Varian VXR 400 S spectrometer at 400 MHz ($^1$H) or on a Bruker Avance DPX-300 spectrometer. Chemical shifts ($\delta$) are reported in ppm and referenced to methanol ($\delta_H$ 3.34, $\delta_C$ 49.50) for solutions in $D_2O$, to DMSO ($\delta_H$ 2.50, $\delta_C$ 39.52) or to $CDCl_3$ ($\delta_H$ 7.26, $\delta_C$ 77.16). Coupling constants (J) are reported in Hz. Resonance allocations were made with the aid of COSY and HSQC experiments. NOESY measurements were carried out with a relaxation delay of 1.000 s and a mixing time of 0.200 s. Accurate electrospray ionisation mass spectra (HR ESI-MS) were obtained on a Finnigan MAT 900 XLT mass spectrometer at the EPSRC National Mass Spectrometry Service Centre in Swansea. Preparative chromatography was performed on a Biologic LP chromatography system equipped with a peristaltic pump and a 254 nm UV Optics Module under the following conditions:

Purification Method 1

Ion-pair chromatography was performed using Lichroprep RP-18 resin gradient 0-10% acetonitrile (or methanol) against 0.05 M TEAB (triethylammonium bicarbonate: prepared by bubbling $CO_2$ gas through a mixture of $Et_3N$ in water until saturation was achieved) over 480 mL, flow rate 5 mL/min. Product-containing fractions were combined and reduced to dryness. The residue was co-evaporated repeatedly with methanol to remove residual TEAB.

Purification Method 2

Anion-exchange chromatography was performed using a Macro prep 25Q resin, gradient 0-100% 1 M TEAB (pH 7.3) against $H_2O$ over 480 mL, flow rate 5 mL/min. Product-containing fractions were combined and reduced to dryness. The residue was co-evaporated repeatedly with methanol to remove residual TEAB.

General Method a: Suzuki-Miyaura Cross-Coupling of 5-I-U, 5-Iodo-UMP 1, 5-Iodo-UDP 3 and 5-Iodo-UTP 4.

A 2-necked round bottom flask with 5-iodouridine-5'-monophosphate 1, 5-iodouridine-5'-diphosphate 3 or 5-iodouridine-5'-triphosphate 4 (1 eq.), $Cs_2CO_3$ (2 eq.) and arylboronic acid (1.5 eq.) was purged with $N_2$. TPPTS (0.0625 eq.), $Na_2Cl_4Pd$ (0.025 eq.) and degassed $H_2O$ (4 mL) were added, and the reaction was stirred under $N_2$ for 1 h at 60° C. Upon completion, the reaction was cooled to room temperature. The black suspension was concentrated under reduced pressure, and the residue was taken up in MeOH. The methanolic suspension was filtered through celite, and the residue was washed with methanol. The combined filtrates were evaporated under reduced pressure and the residue was purified using purification method 1.

5-Iodouridine-5'-monophosphate 1

From 5-I-U

A suspension of 5-I-U (480 mg, 1.3 mmol) and proton sponge (1.7 g, 7.8 mmol) in dry acetonitrile (20 mL) was chilled to −5° C. and stirred under $N_2$. To that suspension was added $POCl_3$ (58 µl, 0.6 mmol) dropwise. The orange-coloured reaction was stirred at −5° C. for 4 h, at which time TLC indicated near complete conversion ($IPA/H_2O/NH_3$ 6:3:1; Rf 0.31; Rf$_{SM}$ 0.71). The reaction was quenched with 250 mL of ice cold 0.2 M TEAB buffer. The pale orange solution was stirred for 1 h at 0° C. After allowing to reach 25° C., the aqueous layer was washed with ethyl acetate (×3) and concentrated under reduced pressure. The crude residue was purified sequentially by purification methods 1 and 2 to provide 1 (472 mg) in its triethylammonium salt form (1.7 eq.) as a colourless, glassy solid in 53% yield.

From Uridine-5'-Monophosphate

Uridine-5'-monophosphate (540 mg, 1.46 mmol) and iodine powder (517 mg, 2.04 mmol) were loaded in a round bottom flask and dissolved in a mixture $CHCl_3$ (30 ml) and 2 M $HNO_3$ (5 ml) and heated at reflux at 80° C. for 12 h. Upon completion, the reaction mixture was allowed to reach room temperature and washed (50 mL×3) with $CHCl_3$. The aqueous layer was concentrated under reduced pressure and purified according to purification method 1 to provide a colourless powder identified as 5-I-UMP 1 (659 mg) in its triethylammonium salt form (1.2 eq.) in 77% yield. $\delta_H$ (400 MHz, $D_2O$) 3.96-4.10 (2H, m, H-5'), 4.22-4.26 (1H, m, H-4'), 4.31 (1H, t, J=4.7 Hz, H-3'), 4.38 (1H, t, J=5.3 Hz, H-2'), 5.93 (1H, d, J=5.3 Hz, H-1'), 8.27 (1H, s, H-6); $\delta_C$ (75.5 MHz, $D_2O$) 64.8 (d, $J_{C,P}$=4.6 Hz, C-5'), 69.6 (C-5), 70.8 (C-3'), 74.6 (s, C-2'), 84.8 (d, $J_{C,P}$=8.8 Hz, C-4'), 89.6 (C-1'), 147.1 (C-6), 152.8 (C-2), 164.3 (C-4); $\delta_P$ (121.5 MHz, $D_2O$) 7.6. m/z (ESI) 448.9255 [M−H]$^-$, $C_9H_{11}IN_2O_9P$ requires 448.9252.

5-Phenyluridine-5'-monophosphate 2a

The triethylammonium salt of the title compound was obtained as a glassy solid in 71% yield (13.5 mg) from 1 (16.5 mg, 36.7 µmol) and phenylboronic acid according to general method A. $\delta_H$ (400 MHz, $D_2O$) 4.01-4.15 (2H, m, H-5'), 4.24-4.30 (1H, m, H-4'), 4.32-4.40 (1H, m, H-3'), 4.45 (1H, t, J=5.6 Hz, H-1'), 5.98 (1H, d, J=5.5 Hz, H-2'), 7.38-7.51 (5H, m, Ph), 7.82 (1H, s, H-6); $\delta_C$ (75.5 MHz, $D_2O$) 85.0 (d, $J_{C,P}$=4.5 Hz, C-5'), 70.6 (C-3'), 74.1 (C-2'), 84.3 (d, $J_{C,P}$=8.3 Hz, C-4'), 89.2 (C-1'), 116.9 (C-5), 129.1, 129.4, 129.5, 132.4

(C-Ph), 139.2 (C-6), 152.3 (C-2), 165.5 (C-4); $\delta_P$ (121.5 MHz, D$_2$O) 7.6. m/z (ESI) 399.0593 [M−H]−, C$_{15}$H$_{16}$N$_2$O$_9$P requires 399.0599.

5-(4-Chlorophenyl)-uridine-5'-monophosphate 2b

The triethylammonium salt of the title compound was obtained as a glassy solid in 20% yield (5.5 mg) from 1 (20 mg, 49.6 µmol) and 4-chlorophenylboronic acid according to general method A. $\delta_H$ (400 MHz, D$_2$O) 4.00-4.12 (2H, m, H-5'), 4.22-4.29 (1H, m, H-4'), 4.30-4.344 (1H, m, H-3'), 4.45 (1H, d, J=5.4 Hz, H-2'), 6.01 (1H, d, J=5.5 Hz, H-1'), 7.46-7.58 (4H, m, Ph), 7.90 (1H, s, H-6); $\delta_C$ (75.5 MHz, D$_2$O), 65.0, 70.9, 74.3, 82.5, 89.6, 111.6, 129.6, 129.9, 131.2, 131.4, 139.6, 152.4, 165.8; $\delta_P$ (121.5 MHz, D$_2$O) 10.4. m/z (ESI) 433.0210 [M−H]−, C$_{15}$H$_{15}$Cl$^{35}$N$_2$O$_9$P requires 433.0209.

5-(4-Methyl-3-nitrophenyl))-uridine-5'-monophosphate 2c

The triethylammonium salt of the title compound was obtained as a glassy solid in 79% yield (10.9 mg) from 1 (10 mg, 22.2 µmol) and 4-methyl-3-nitrophenylboronic acid according to general method A. $\delta_H$ (400 MHz, D$_2$O) 2.57 (3H, s, Me), 4.01-4.12 (2H, m, H-5'), 4.26-4.28 (1H, m, H-4'), 4.33 (1H, t, J=4.7 Hz, H-3'), 4.45 (1H, t, J=5.4 Hz, H-2'), 6.00 (1H, d, J=5.5 Hz, H-1'), 7.46-7.71 (2H, 2d, J=7.9 and 8.0 Hz, Ph), 7.99 (1H, s, H-6) 8.16 (1H, s, Ph); $\delta_C$ (75.5 MHz, D$_2$O) 19.8 (Me), 64.9 (C-5'), 70.5 (C-3'), 74.3 (C-2'), 84.3 (d, J=9.1 Hz, C-4'), 89.4 (C-1'), 114.4, 115.8, 125.2, 131.3, 133.9, 134.0 (C-5+C-Ph), 139.7 (C-6), 149.2 (C-Ph), 152.0 (C-2), 164.9 (C-4); $\delta_P$ (121.5 MHz, D$_2$O) 7.6. m/z (ESI) 458.0607 [M−H]−, C$_{16}$H$_{17}$N$_3$O$_{11}$P requires 458.0606.

5-(3-N-BOC-aminomethylphenyl)-uridine-5'-monophosphate 2d

The triethylammonium salt of the title compound was obtained as a glassy solid in % yield (10.2 mg) from 1 (10 mg, 22.2 µmol) and 3-N-BOC-aminomethylphenylboronic acid according to general method A. $\delta_H$ (400 MHz, D$_2$O) 1.42 (9H, s, $^t$Bu), 4.00-4.10 (2H, m, H-5'), 4.20-4.35 (4H, m, H-4', H-3', CH$_2$), 4.47 (1H, t, J=5.5 Hz, H-2'), 6.01 (1H, d, J=5.7 Hz, H-1'), 7.30-7.48 (4H, m, Ph), 7.86 (1H, s, H-6); $\delta_C$ (75.5 MHz, D$_2$O) 20.4 (CH$_2$), 28.2 ($^t$Bu), 65.1 (d, J$_{C,P}$=6.0 Hz, C-5'), 70.7 (C-3'), 74.1 (C-2'), 84.3 (d, J$_{C,P}$=8.3 Hz, C-4'), 84.9 ($^t$Bu), 89.3 (C-1'), 101.4 (C-Ph), 116.7 (C-5), 127.4, 127.7, 128.2, 129.7, 132.7 (C-Ph), 139.2 (C-6), 152.2 (C-2), 159.1 (CHO), 165.4 (C-4); δp (121.5 MHz, D$_2$O) 7.6. m/z (ESI) 528.1384 [M−H]−, C$_{21}$H$_{27}$N$_3$O$_{11}$P requires 528.1389.

5-(3-Hydroxyphenyl)-uridine-5'-monophosphate 2e

The triethylammonium salt of the title compound was obtained as a glassy solid in 52% yield (6.8 mg) from 1 (10 mg, 22.2 µmol) and 3-hydroxyphenylboronic acid according to general method A. $\delta_H$ (400 MHz, D$_2$O) 4.05-4.12 (2H, m, H-5'), 4.27-4.31 (1H, m, H-4'), 4.40 (1H, t, J=4.7 Hz, H-3'), 4.47 (1H, t, J=4.9 Hz, H-2'), 6.01 (1H, d, J=4.9 Hz, H-1'), 6.86 (1H, d, J=7.3 Hz, Ph), 7.23 (1H, s, Ph), 7.25-7.27 (1H, m, Ph), 7.33 (1H, t, J=7.8 Hz, Ph), 8.09 (1H, s, H-6); $\delta_C$ (75.5 MHz, D$_2$O) 64.3 (d, J$_{C,P}$=3.8 Hz, C-5'), 70.2 (C-3'), 74.8 (C-2'), 84.5 (d, J$_{C,P}$=9.8 Hz, C-4'), 89.4 (C-1'), 115.4, 115.6, 116.0, 120.7, 130.7, 133.9 (C-5+C-Ph), 139.3 (C-6), 152.0 (C-2), 156.9 (C-4); $\delta_P$ (121.5 MHz, D$_2$O) 7.6. m/z (ESI) 415.0540 [M−H]−, C$_{15}$H$_{16}$N$_{12}$O$_{10}$P requires 415.0548.

5-(2-Hydroxyphenyl)-uridine-5'-monophosphate 2f

The triethylammonium salt of the title compound was obtained as a glassy solid in 33% yield (4.4 mg) from 1 (10 mg, 22.2 µmol) and 2-hydroxyphenylboronic acid according to general method A $\delta_H$ (400 MHz, D$_2$O) 3.98-4.01 (2H, m, H-5'), 4.23-4.27 (1H, m, H-4'), 4.30-4.34 (1H, m, H-3'), 4.42 (1H, t, J=5.4 Hz, H-2'), 6.04 (1H, d, J=5.5 Hz, H-1'), 7.02 (2H, dd, J=7.6 and 11.5 Hz, Ph), 7.30-7.35 (2H, m, Ph), 7.98 (1H, s, H-6); $\delta_C$ (150 MHz, D$_2$O) 64.3, 70.6, 74.3, 84.4 (d, J$_{C,P}$=8.6 Hz), 89.0, 112.7, 117.7, 120.2, 121.4, 130.7, 132.0, 141.2, 152.1, 154.0, 165.4; $\delta_P$ (121.5 MHz, D$_2$O) 7.6. m/z (ESI) 415.0546 [M−H]−, C$_{15}$H$_{16}$N$_2$O$_{10}$P requires 415.0548.

5-(2-Naphtyl)-uridine-5'-monophosphate 2g

The triethylammonium salt of the title compound was obtained as a glassy solid in 47% yield (6.3 mg) from 1 (10 mg, 22.2 µmol) and 1-naphthylboronic acid according to general method A. $\delta_H$ (400 MHz, D$_2$O) 3.90-4.03 (2H, m, H-5'), 4.22-4.49 (4H, m, H-2', H-3', H-4'), 6.07 (1H, d, J=5.6 Hz, H-1'), 7.49-7.65 (4H, m, napht), 7.72-7.78 (1H, m, napht), 7.93 (1H, s, H-6), 8.01 (2H, m, napht); $\delta_C$ (75.5 MHz, D$_2$O) 64.6 (C-5'), 70.9 (C-3'), 73.8 (C-2'), 83.7 (C-4'), 89.3 (C-1'), 113.2 (C-5), 117.6, 125.8, 126.5, 127.1, 127.4, 129.1, 129.5, 130.0, 130.1, 133.9 (C-naphtyl), 140.9 (C-6), 154.6 (C-2), 166.0 (C-4); $\delta_P$ (121.5 MHz, D$_2$O) 7.6. m/z (ESI) 449.0760 [M−H]−, C$_{19}$H$_{18}$N$_2$O$_9$P requires 449.0755.

5-(4-Carboxyphenyl)-uridine-5'-monophosphate 2h

The triethylammonium salt of the title compound was obtained as a glassy solid in 60% yield (9.6 mg) from 1 (10 mg, 22.2 µmol) and 4-carboxyphenylboronic acid according to general method A. $\delta_H$ (400 MHz, D$_2$O) 4.00-4.08 (2H, m, H-5'), 4.25-4.30 (1H, m, H-4'), 4.31-4.35 (1H, m, H-3'), 4.48 (1H, t, J=5.6 Hz, H-2'), 6.00 (1H, d, J=5.6 Hz, H-1'), 7.38, 7.69 (4H, 2d, J=8.1 Hz, Ph), 7.73 (1H, s, H-6); $\delta_C$ (75.5 MHz, D$_2$O) 64.7 (d, J$_{C,P}$=5.3 Hz, C-5'), 70.6 (C-3'), 73.8 (C-2'), 84.3 (d, J$_{C,P}$=8.3 Hz, C-4'), 89.7 (C-1'), 116.3 (C-5), 129.2, 129.7, 135.2, 136.7 (C-Ph), 139.8 (C-6), 152.2 (C-2), 165.3 (C-4), 171.1 (COOH); $\delta_P$ (121.5 MHz, D$_2$O) 7.6. m/z (ESI) 443.0498 [M−H]−, C$_{16}$H$_{16}$N$_2$O$_{11}$P requires 443.0497.

5-(4-Trifluoromethylphenyl)-uridine-5'-monophosphate 2i

The triethylammonium salt of the title compound was obtained as a glassy solid in 63% yield (9.2 mg) from 1 (10 mg, 22.2 µmol) and 4-trifluomethylphenylboronic acid according to general method A. $\delta_H$ (400 MHz, D$_2$O) 4.01-4.06 (2H, m, H-5'), 4.24-4.28 (1H, m, H-4'), 4.30-4.36 (1H, m, H-3'), 4.46 (1H, t, J=5.6 Hz, H-2'), 6.02 (1H, d, J=5.7 Hz, H-1'), 7.68-7.80 (4H, 2d, J=8.3 Hz, Ph), 7.98 (1H, s, H-6); $\delta_C$ (75.5 MHz, D$_2$O) 64.6 (d, J$_{C,P}$=3.8 Hz, C-5'), 70.6 (C-3'), 74.1 (C-2'), 84.5 (d, J$_{C,P}$=8.3 Hz, C-4'), 89.4 (C-1'), 115.6 (C-5), 126.1 (q, J=3.8 Hz, C—F$_3$), 129.8, 130.2, 136.3 (C-Ph), 140.1 (C-6), 152.2 (C-2), 157.7 (C-Ph), 165.1 (C-4); $\delta_P$ (121.5 MHz, D$_2$O) 7.6. m/z (ESI) 467.0473 [M−H]−, C$_{16}$H$_{15}$F$_3$N$_2$O$_9$P requires 467.0473.

5-(5-Methoxy-3-pyridyl)-uridine-5'-monophosphate 2j

The triethylammonium salt of the title compound was obtained as a glassy solid in 45% yield (6.6 mg) from 1 (10 mg, 22.2 µmol) and 5-methoxypyridine-3-boronic acid according to general method A. $\delta_H$ (400 MHz, D$_2$O) 3.92 (3H, s, MeO), 4.01-4.07 (2H, m, H-5'), 4.26-4.28 (1H, m, H-4'), 4.33 (1H, t, J=4.7 Hz, H-3'), 4.46 (1H, t, J=5.4 Hz, H-2'), 6.01 (1H, d, J=5.5 Hz, H-1'), 7.59 (1H, s, pyr), 7.68-8.12 (2H, m, pyr), 8.00 (1H, s, H-6); $\delta_C$ (150 MHz, D$_2$O) 56.5, 64.7, 70.5, 74.1, 84.3, 89.5, 129.2, 131.1, 130.8, 135.4, 136.5, 140.1, 144.2, 152.0, 164.9; $\delta_P$ (121.5 MHz, D$_2$O) 7.6. m/z (ESI) 430.0658 [M–H]$^-$, C$_{15}$H$_{17}$N$_3$O$_{10}$P requires 430.0657.

5-(3-Methanesulfonylphenyl)-uridine-5'-monophosphate 2k

The triethylammonium salt of the title compound was obtained as a glassy solid in 58% yield (8.8 mg) from 1 (10 mg, 22.2 µmol) and 3-(methylsulfonyl)phenylboronic acid according to general method A. $\delta_H$ (400 MHz, D$_2$O) 3.30 (3H, s, Me), 4.00-4.06 (2H, m, H-5'), 4.25-4.27 (1H, m, H-4'), 4.32 (1H, t, J=4.8 Hz, H-3'), 4.48 (1H, t, J=5.5 Hz, H-2'), 6.02 (1H, d, J=5.6 Hz, H-1'), 7.70-8.13 (4H, m, Ph), 8.03 (1H, s, H-6); $\delta_C$ (75.5 MHz, D$_2$O) 43.8 (Me), 64.6 (C-5'), 70.5 (C-3'), 74.1 (C-2'), 84.4 (d, J$_{C,P}$=7.5 Hz, C-4'), 89.5 (C-1'), 115.0 (C-5), 127.3, 127.9, 130.9, 134.0, 139.4, 139.5 (C-Ph), 140.2 (C-6), 152.1 (C-2), 165.1 (C-4); $\delta_P$ (121.5 MHz, D$_2$O) 7.6. m/z (ESI) 477.0380 [M–H]$^-$, C$_{16}$H$_{18}$N$_2$O$_{11}$PS requires 477.0374.

5-(4-Methoxyphenyl)-uridine-5'-monophosphate 2l

The triethylammonium salt of the title compound was obtained as a glassy solid in 57% yield (15.3 mg) from 1 (20 mg, 49.6 µmol) and 4-methoxyphenylboronic acid according to general method A. $\delta_H$ (300 MHz, D$_2$O) 4.02-4.14 (2H, m, H-5'), 4.23-4.28 (1H, m, H-4'), 4.32 (1H, t, J=4.6 Hz, H-3'), 4.42 (1H, t, J=5.1, H-2'), 5.98 (1H, d, J=5.6 Hz, H-1'), 7.02, 7.44 (4H, 2d, J=8.0 and 8.0 Hz, Ph), 7.76 (1H, s, H-6); $\delta_C$ (100.6 MHz, D$_2$O) 55.9, 65.1 (d, J$_{C,P}$=4.7 Hz), 70.6, 74.1, 84.1 (d, J$_{C,P}$=8.6 Hz), 89.2, 114.6, 116.1, 124.9, 130.5, 138.2, 151.9, 159.3, 165.2; $\delta_P$ (121.5 MHz, D$_2$O) 3.9. m/z (ESI) 429.0701 [M–H]$^-$, C$_{16}$H$_{18}$N$_2$O$_{10}$P requires 429.0705.

5-(Furan-2-yl)-uridine-5'-monophosphate 2m

The triethylammonium salt of the title compound was obtained as a glassy solid in 57% yield (14.6 mg) from 1 (20 mg, 49.6 µmol) and 2-furanboronic acid according to general method A. $\delta_H$ (400 MHz, D$_2$O) 4.05-4.15 (2H, m, H-5'), 4.25-4.31 (1H, m, H-4'), 4.31-4.36 (1H, m, H-3'), 4.45 (1H, t, J=5.3 Hz, H-2'), 6.00 (1H, d, J=5.3 Hz, H-1'), 6.52 (1H, dd, J=1.8 and 3.4 Hz, H-fur), 6.85 (1H, d, J=3.4 Hz, H-fur), 7.55 (1H, d, J=1.7 Hz, H-fur), 8.15 (1H, s, H-6); $\delta_C$ (100.6 MHz, D$_2$O) 65.0 (d, J$_{C,P}$=4.3 Hz), 70.5, 74.3, 84.1 (d, J$_{C,P}$=8.4 Hz), 89.4, 108.0, 109.5, 112.0, 136.0, 143.1, 145.8, 151.3, 162.8; $\delta_P$ (121.5 MHz, D$_2$O) 7.6. m/z (ESI) 389.0397 [M–H]$^-$, C$_{13}$H$_{14}$N$_{12}$O$_{10}$P requires 389.0392.

5-(5-Formylfuran-2-yl))-uridine-5'-monophosphate 2n

The triethylammonium salt of the title compound was obtained as a glassy solid in 56% yield (8.8 mg) from 1 (10 mg, 22.2 µmol) and 5-formyl-2-furanboronic acid according to general method A. $\delta_H$ (400 MHz, D$_2$O) 4.00-4.15 (2H, m, H-5'), 4.24-4.26 (1H, m, H-4'), 4.30-4.38 (1H, m, H-3'), 4.49-4.53 (1H, m, H-2'), 5.97 (1H, d, J=5.3 Hz, H-1'), 7.16 (1H, d, J=3.7 Hz, fur), 7.58 (1H, d, J=3.7 Hz, fur), 8.40 (1H, s, H-6) 9.47 (1H, s, CHO); $\delta_C$ (75.5 MHz, D$_2$O) 64.9 (C-5'), 70.4 (C-3'), 74.0 (C-2'), 84.4 (d, J$_{C,P}$=8.5 Hz, C-4'), 90.1 (C-1'), 106.4, 112.6, 119.0, 138.7 (C-5, C-fur), 140.1 (C-6), 151.4 (C-2), 153.7 (C-fur), 172.3 (C-4), 181.1 (CHO); $\delta_P$ (121.5 MHz, D$_2$O) 7.6. m/z (ESI) 417.0336 [M–H]$^-$, C$_{14}$H$_{14}$N$_2$O$_{11}$P requires 417.0341.

5-(3-Formylthien-2-yl)-uridine-5'-monophosphate 2o

The triethylammonium salt of the title compound was obtained as a glassy solid in 25% yield (3.5 mg) from 1 (10 mg, 22.2 µmol) and 3-formyl-2-thiopheneboronic acid according to general method A. $\delta_H$ (400 MHz, D$_2$O) 3.98-4.06 (2H, m, H-5'), 4.24-4.27 (1H, m, H-4'), 4.27-4.32 (1H, m, H-3'), 4.40-4.45 (1H, m, H-2'), 6.00 (1H, m, H-1'), 7.55 (2H, m, Th), 8.13 (1H, s, H-6) 9.67 (1H, s, CHO); $\delta_C$ (150 MHz, D$_2$O) 64.4 (C-5'), 70.4 (C-3'), 74.2 (C-2'), 84.3 (C-4'), 89.6 (C-1'), 107.6 (C-5), 127.0, 128.5, 138.9, 142.3 (C—Th), 144.7 (C-6), 151.8 (C-2), 164.7 (C-4), 188.9 (CHO); $\delta_P$ (121.5 MHz, D$_2$O) 7.6. m/z (ESI) 433.0117 [M–H]$^-$, C$_{14}$H$_{14}$N$_2$O$_{10}$PS requires 433.0112.

5-(5-Acetylthien-2-yl)-uridine-5'-monophosphate 2p

The triethylammonium salt of the title compound was obtained as a glassy solid in 31% yield (4.1 mg) from 1 (10 mg, 22.2 µmol) and 5-acetyl-2-thiopheneboronic acid according to general method A. $\delta_H$ (400 MHz, D$_2$O) 2.60 (3H, s, Me), 4.10-4.18 (2H, m, H-5'), 4.29-4.34 (1H, m, H-4'), 4.38 (1H, t, J=5.7 Hz, H-3'), 4.46 (1H, t, J=5.2 Hz, H-2'), 6.00 (1H, d, J=5.2 Hz, H-1'), 7.60 (1H, d, J=4.2 Hz, Th), 7.90 (1H, d, J=4.2 Hz, Th), 8.35 (1H, s, H-6); $\delta_C$ (150 MHz, D$_2$O) 26.5, 64.5, 70.6, 74.7, 84.7, 89.5, 109.7, 126.0, 136.1, 138.8, 142.4, 143.1, 151.2, 163.5, 196.7; $\delta_P$ (121.5 MHz, D$_2$O) 7.6. m/z (ESI) 447.0263 [M–H]$^-$, C$_{15}$H$_{16}$N$_2$O$_{10}$PS requires 447.0269.

5-(5-Formylthien-2-yl)-uridine-5'-monophosphate 2q

The triethylammonium salt of the title compound was obtained as a glassy solid in 61% yield (8.6 mg) from 1 (10 mg, 22.2 µmol) and 5-formyl-2-thiopheneboronic acid according to general method A. $\delta_H$ (400 MHz, D$_2$O) 4.12-4.20 (2H, m, H-5'), 4.29-4.31 (1H, m, H-4'), 4.38 (1H, t, J=4.7 Hz, H-3'), 4.45 (1H, t, J=5.0 Hz, H-2'), 5.98 (1H, d, J=5.0 Hz, H-1'), 7.66 (1H, d, J=4.0 Hz, Th), 7.94 (1H, d, J=4.0 Hz, Th), 8.38 (1H, s, H-6) 9.75 (1H, s, CHO); $\delta_C$ (75.5 MHz, D$_2$O) 64.7 (d, J$_{C,P}$=4.5 Hz, C-5'), 70.4 (C-3'), 74.9 (C-2'), 84.4 (C-4'), 89.7 (C-1'), 110.0, 125.9, 139.1, 140.1, 142.0 (C5+C—Th), 144.9 (C-6), 152.7 (C-2), 163.5 (C-4), 187.8 (CHO); $\delta_P$ (121.5 MHz, D$_2$O) 7.6. m/z (ESI) 433.0107 [M–H]$^-$, C$_{14}$H$_{14}$N$_2$O$_{10}$PS requires 433.0112.

5-(5-Formylthien-2-yl)-uridine 2q'

The title compound was obtained from 5-I-U (100 mg, 270 µmol) and 5-formyl-2-thiopheneboronic acid according to general method A in 23% yield (16 mg). $\delta_H$ (400 MHz, DMSO-d$_6$) 3.65-3.85 (2H, m, H-5'), 3.90-3.95 (1H, m, H-4'), 4.02-4.17 (2H, m, H-2' and H-3'), 5.11 (1H, d, J=5.9 Hz, OH-3'), 5.54 (1H, d, J=5.0 Hz, OH-2'), 5.60 (1H, t, J=4.3 Hz, OH-5'), 5.80 (1H, d, J=3.0 Hz, H-1'), 7.56 (1H, d, J=4.1 Hz, Th), 7.93 (1H, d, J=4.0 Hz, Th), 9.02 (1H, s, H-6), 9.87 (1H, s, CHO), 11.9 (1H, s, NH); $\delta_C$ (75.5 MHz, DMSO-d$_6$) 59.6 (C-5'), 68.7 (C-3'), 74.5 (C-2'), 84.4 (C-4'), 89.5 (C-1'), 106.9 (C-5), 122.9, 137.3, 138.7, 141.6, 144.4, 149.4 (C-2+C-6+C—Th), 161.4 (C-4), 184.3 (CHO). m/z (ESI) 353.0448 [M–H]$^-$, C$_{14}$H$_{13}$N$_2$O$_7$S requires 353.0449.

5-Iodouridine-5'-monophosphoromorpholidate

5-Iodouridine-5'-monophosphate 1 (292 mg, 0.65 mmol) was dissolved in dry DMSO and co-evaporated (×3) with dry DMF to remove residual water and finally dissolved in 0.5 mL of dry DMSO. Morpholine (400 µL, 4.6 mmol) was added to the reaction mixture, stirred at room temperature for 5 minutes. Dipyridyl disulfide (500 mg, 2.3 mmol) and triphenylphosphine (600 mg, 2.3 mmol) were both added in 5 minutes interval. The reaction mixture was further stirred for 60 minutes at room temperature before being quenched with 0.1M NaI in acetone until a colourless solid precipitated out of the solution. The surnatant was removed and 354 mg of colourless powder of 5-iodouridine-5'-monophosphomorpholidate was isolated (99% yield). $\delta_H$ (400 MHz, D$_2$O) 3.04-3.16 (4H, m, morph), 3.63-3.73 (4H; m, morph), 3.98-4.15 (2H, m, H-5'), 4.24-4.26 (1H, m, H-4'), 4.27-4.32 (1H, m, H-3'), 4.37 (1H, t, J=5.3 Hz, H-2'), 5.94 (1H, d, J=5.3 Hz, H-1'), 8.18 (1H, s, H-6); $\delta_C$ (75.5 MHz, D$_2$O) 44.2 (morph), 63.4 (d, $J_{C,P}$=5.3 Hz, C-5'), 66.3 (morph), 68.0 (C-5), 68.6 (C-3'), 73.2 (C-2'), 83.0 (d, $J_{C,P}$=8.5 Hz, C-4'), 88.2 (C-1'), 145.0 (C-6), 153.0 (C-2), 161.9 (C-4); $\delta_P$ (121.5 MHz, D$_2$O) 11.0. m/z (ESI) 519.9968 [M+H]$^+$, C$_{13}$H$_{19}$IN$_3$O$_9$P requires 519.9976.

5-Iodouridine-5'-diphosphate 3

5-Iodouridine-5'-monophosphomorpholidate (50 mg, 96 µmol) was iteratively (×3) dried by co-evaporation with pyridine. To the colourless solid was added KH$_3$PO$_4$ (34 mg, 191 µmol) as tributylammonium salt and the mixture was further co-evaporated (×3) in pyridine. Tetrazole (33 mg, 470 µmol) and dry DMF (5 mL) were added to the dry mixture. The reaction was left stirring for 5 h at room temperature. The crude mixture was concentrated under reduced pressure and isolated using purification method 1. The triethylammonium salt of the title compound (1.0 eq.) was obtained as a glassy solid in 66% yield (40.2 mg). $\delta_H$ (400 MHz, D$_2$O) 4.00-4.05 (2H, m, H-5'), 4.10-4.15 (1H, m, H-4'), 4.20-4.25 (2H, m, H-3', H-2'), 5.77 (1H, d, J=4.6 Hz, H-1'), 8.08 (1H, s, H-6); $\delta_C$ (75.5 MHz, D$_2$O) 65.5 (C-5'), 69.2 (C-5), 70.3 (C-3'), 74.4 (s, C-2'), 84.1 (d, $J_{C,P}$=8.5 Hz, C-4'), 89.3 (C-1'), 146.7 (C-6), 152.4 (C-2), 163.9 (C-4); $\delta_P$ (121.5 MHz, D$_2$O) 6.6 (d, $J_{P,P}$=23.1 Hz), −11.2 (d, $J_{P,P}$=23.1 Hz). m/z (ESI) 528.8912 [M−H]$^-$, C$_9$H$_{12}$IN$_2$O$_{12}$P$_2$ requires 528.8916

5-Iodouridine-5'-triphosphate 4

5-Iodouridine-5'-monophosphomorpholidate (81 mg, 0.156 mmol) was iteratively (×3) dried by co-evaporation with pyridine. To the white solid was added pyrophosphate (280 mg, 0.628 mmol) as tributylammonium salt and the mixture was further co-evaporated (×3) in pyridine. Tetrazole (55 mg, 0.785 mmol) and dry DMF (5 mL) were further added to the dry mixture and the reaction was left stirring for 5 h at room temperature. The crude mixture was concentrated under reduced pressure and isolated using purification method 1. The triethylammonium salt of the title compound (3.2 eq.) was obtained as a glassy solid in 60% yield (86.8 mg). $\delta_H$ (400 MHz, D$_2$O) 4.20-4.26 (2H, m, H-5'), 4.26-4.30 (1H, m, H-4'), 4.37-4.44 (2H, m, H-3', H-2'), 5.94 (1H, d, J=4.9 Hz, H-1'), 8.27 (1H, s, H-6); $\delta_C$ (75.5 MHz, D$_2$O) 65.7 (d, $J_{C,P}$=6.1 Hz, C-5'), 69.2 (C-5), 70.4 (C-3'), 74.4 (s, C-2'), 84.3 (d, J=9.1 Hz, C-4'), 89.1 (C-1'), 146.7 (C-6), 152.4 (C-2), 164.0 (C-4); $\delta_P$ (121.5 MHz, D$_2$O) −6.5 (d, $J_{P,P}$=20.7 Hz), −11.6 (d, $J_{P,P}$=19.4 Hz), −22.6 (d, $J_{P,P}$=20.7 Hz). m/z (ESI) 608.8588 [M−H]$^-$, C$_9$H$_{13}$IN$_2$O$_{15}$P$_3$ requires 608.8579.

5-Phenyluridine-5'-diphosphate 5a

The triethylammonium salt of the title compound (1.9 eq.) was obtained as a glassy solid in 73% yield (10.6 mg) from 3 (11.6 mg, 20.8 µmol) and phenylboronic acid according to general method A. $\delta_H$ (400 MHz, D$_2$O) 4.15-4.19 (2H, m, H-5'), 4.27-4.31 (1H, m, H-4'), 4.38-4.43 (1H, m, H-3'), 4.47 (1H, t, J=5.6 Hz, H-2'), 6.05 (1H, d, J=5.8 Hz, H-1'), 7.40-7.58 (5H, m, phenyl), 7.88 (1H, s, H-6); $\delta_C$ (75.4 MHz, D$_2$O) 65.7 (d, $J_{C,P}$=3.7 Hz, C-5'), 70.5 (C-3'), 73.9 (C-2'), 84.1 (d, $J_{C,P}$=5.0 Hz, C-4'), 89.1 (C-1'), 118.9 (C-5), 129.1, 129.4, 129.5, 133.8 (C-Ph), 139.2 (C-6), 152.3 (C-2), 165.5 (C-4); $\delta_P$ (121 MHz, D$_2$O) −6.6 (d, $J_{P,P}$=23.1 Hz), −11.1 (d, $J_{P,P}$=23.1 Hz). m/z (ESI) 239.0096 [M−2H]$^{2-}$, C$_{15}$H$_{16}$N$_2$O$_{12}$P$_2$ requires 239.0095.

5-(4-Methoxyphenyl)uridine-5'-diphosphate 5b

The triethylammonium salt of the title compound (1.9 eq.) was obtained as a glassy solid in 50% yield (7.2 mg) from 3 (11.0 mg, 20.8 µmol) and 4-methoxyphenylboronic acid according to general method A. $\delta_H$ (400 MHz, D$_2$O) 3.87 (3H, s, MeO), 4.16-4.22 (2H, m, H-5'), 4.26-4.31 (1H, m, H-4'), 4.41 (1H, m, H-3'), 4.47 (1H, t, J=5.6 Hz, H-2'), 6.04 (1H, d, J=5.8 Hz, H-1'), 7.07 (2H, d, J=8.8 Hz, Ph), 7.49 (2H, d, J=8.8 Hz, Ph), 7.83 (1H, s, H-6); $\delta_C$ (125 MHz, D$_2$O) 55.9 (MeO), 65.7 (d, $J_{C,P}$=3.0 Hz, C-5'), 70.5 (C-3'), 73.9 (C-2'), 82.6 (C-4'), 89.0 (C-1'), 114.9, 116.5, 125.1, 130.8 (C-5+C-Ph), 138.5 (C-6), 152.3 (C-2), 159.6 (C-Ph), 166.1 (C-4); $\delta_P$ (121 MHz, D$_2$O) −6.6 (d, $J_{P,P}$=23.1 Hz), −11.1 (d, $J_{P,P}$=23.1 Hz). m/z (ESI) 254.0149 [M−2H]$^{2-}$, C$_{16}$H$_{18}$N$_2$O$_{13}$P$_2$ requires 254.0148.

5-(Furan-2-yl)uridine-5'-diphosphate 5c

The triethylammonium salt of the title compound (1.9 eq.) was obtained as a glassy solid in 60% yield (8.6 mg) from 3 (11.0 mg, 20.8 µmol) and 2-furanboronic acid according to general method A. $\delta_H$ (400 MHz, D$_2$O) 4.20-4.26 (2H, m, H-5'), 4.29-4.33 (1H, m, H-4'), 4.44 (1H, t, J=5.4 Hz, H-3'), 4.49 (1H, t, J=5.4 Hz, H-2'), 6.04 (1H, d, J=5.5 Hz, H-1'), 6.54 (1H, dd, J=1.8 and 3.4 Hz, fur), 6.89 (1H, d, J=3.3 Hz, fur), 7.59 (1H, d, J=1.1 Hz, fur), 8.21 (1H, s, H-6); $\delta_C$ (75.5 MHz, D$_2$O) 65.9 (C-5'), 70.7 (C-3'), 74.5 (C-2'), 84.4 (C-4'), 89.5 (C-1'), 108.4 (C-5), 109.9 (fur4), 112.4 (fur3), 136.6 (C-6), 143.7 (fur2), 146.3 (fur1), 152.0 (C-2), 163.6 (C-4); $\delta_P$ (121 MHz, D$_2$O) −6.5 (d, $J_{P,P}$=23.1 Hz), −11.0 (d, $J_{P,P}$=23.1 Hz). m/z (ESI) 233.9991 [M−2H]$^{2-}$, C$_{13}$H$_{14}$N$_2$O$_{13}$P$_2$ requires 233.9991.

5-(5-Formylthien-2-yl)uridine-5'-diphosphate 5d

The triethylammonium salt of the title compound (1.6 eq.) was obtained as a glassy solid in 77% yield (8.2 mg) from 3 (14.0 mg, 26.4 µmol) and 5-formyl-2-thiopheneboronic acid according to general method A. $\delta_H$ (400 MHz, D$_2$O) 4.26-4.32 (2H, m, H-5'), 4.32-4.35 (1H, m, H-4'), 4.43-4.50 (2H, m, H-2' and H-3'), 6.01-6.07 (1H, m, H-1'), 7.71-7.75 (1H, m, Th), 7.99-8.01 (1H, m, Th), 8.45 (1H, s, H-6); 9.78 (1H, s, CHO); $\delta_C$ (75.5 MHz, D$_2$O) 65.5 (C-5'), 70.2 (C-3'), 74.9 (C-2'), 84.2 (C-4'), 89.7 (C-1'), 109.3 (C-5), 125.8, 138.9, 140.3, 142.0, 144.8 (C-6+C—Th), 151.1 (C-2), 163.3 (C-4), 187.8 (CHO); $\delta_P$ (121 MHz, D$_2$O) −6.5 (d, $J_{P,P}$=23.1 Hz), −11.0 (d, $J_{P,P}$=23.1 Hz). m/z (ESI) 512.9776 [M−H]⁻, $C_{14}H_{15}N_2O_{13}P_2S_1$ requires 512.9776.

5-Phenyluridine-5'-triphosphate 6a

The triethylammonium salt of the title compound (3.2 eq.) was obtained as a glassy solid in 85% yield (34.2 mg) from 4 (20 mg, 33.8 μmol) and phenylboronic acid according to general method A. $\delta_H$ (400 MHz, $D_2O$) 4.17-4.27 (2H, m, H-5'), 4.29-4.31 (1H, m, H-4'), 4.43-4.52 (2H, m, H-2' and H-3'), 6.06 (1H, d, J=5.5 Hz, H-1'), 7.40-7.57 (5H, m, Ph), 7.92 (1H, s, H-6); $\delta_C$ (125 MHz, $D_2O$) 66.0 (C-5'), 70.7 (C-3'), 74.1 (C-2'), 84.3 (C-4'), 88.9 (C-1'), 117.0 (C-5), 129.2, 129.5, 129.6, 132.4, (C-Ph), 139.2 (C-6), 152.4 (C-2), 165.5 (C-4); $\delta_P$ (121 MHz, $D_2O$) −6.5 (d, $J_{P,P}$=20.7 Hz), −11.1 (d, $J_{P,P}$=19.7 Hz), −22.6 (d, $J_{P,P}$=20.7 Hz). m/z (ESI) 558.9935 [M−H]⁻, $C_{15}H_{18}N_2O_{15}P_3$ requires 558.9926.

5-(4-Methoxyphenyl)uridine-5'-triphosphate 6b

The triethylammonium salt of the title compound (3.0 eq.) was obtained as a glassy solid in 53% yield (12.1 mg) from 4 (10.9 mg, 17.9 μmol) and 4-methoxyphenylboronic acid according to general method A. $\delta_H$ (400 MHz, $D_2O$) 3.87 (3H, s, MeO), 4.16-4.28 (2H, m, H-5'), 4.29-4.32 (1H, m, H-4'), 4.44 (1H, t, J=5.4 Hz, H-3'), 4.49 (1H, t, J=5.4, H-2'), 6.06 (1H, d, J=6.0 Hz, H-1'), 7.07 (2H, d, J=8.9 Hz, Ph), 7.50 (2H, d, J=8.8 Hz, Ph), 7.86 (1H, s, H-6); $\delta_C$ (75.5 MHz, $D_2O$) 65.9 (MeO), 65.9 (C-5'), 70.6 (C-3'), 73.9 (C-2'), 84.2 (d, $J_{C,P}$=8.8 Hz, C-4'), 88.7 (C-1'), 114.9, 116.6, 125.1, 130.8, 138.4, 152.3, 159.6, 165.6 (C-2, C-4, C-6, C-5, C-Ph); op (121 MHz, $D_2O$) −6.5 (d, $J_{P,P}$=20.7 Hz), −11.5 (d, $J_{P,P}$=19.7 Hz), −22.7 (d, $J_{P,P}$=20.1 Hz). m/z (ESI) 589.0040 [M−H]⁻, $C_{16}H_{20}N_2O_{16}P_3$ requires 589.0031.

5-(Furan-2-yl)uridine-5'-triphosphate 6c

The triethylammonium salt of the title compound (3.0 eq.) was obtained as a glassy solid in 74% yield (11.4 mg) from 4 (10.9 mg, 17.9 μmol) and 2-furanboronic acid according to general method A. $\delta_H$ (400 MHz, $D_2O$) 4.23-4.30 (2H, m, H-5'), 4.31-4.33 (1H, m, H-4'), 4.45-4.52 (2H, m, H-2' and H-3'), 6.06 (1H, d, J=5.2 Hz, H-1'), 6.54 (1H, d, J=1.5 Hz, fur), 6.89 (1H, d, J=3.1 Hz, fur), 7.59 (1H, s, fur), 8.23 (1H, s, H-6); $\delta_C$ (125 MHz, $D_2O$) 65.9 (d, $J_{C,P}$=4.3 Hz, C-5'), 70.4 (C-3'), 74.2 (C-2'), 84.4 (d, $J_{C,P}$=7.6 Hz, C-4'), 89.0 (C-1'), 108.2 (C-5), 109.6 (fur4), 112.1 (fur3), 136.4 (C-6), 143.5 (fur2), 146.0 (fur1), 151.7 (C-2), 163.3 (C-4); $\delta_P$ (121 MHz, $D_2O$) −6.5 (d, $J_{P,P}$=20.7 Hz), −11.5 (d, $J_{P,P}$=19.7 Hz), −22.6 (d, $J_{P,P}$=20.1 Hz). m/z (ESI) 548.9728 [M−H]⁻, $C_{13}H_{16}N_2O_{16}P_3$ requires 548.9718.

5-(5-Formylthien-2-yl)uridine-5'-triphosphate 6d

The triethylammonium salt of the title compound (3.4 eq.) was obtained as a glassy solid in 67% yield (16.9 mg) from 4 (16 mg, 26.3 μmol) and 5-formyl-2-thiopheneboronic acid according to general method A. $\delta_H$ (400 MHz, $D_2O$) 4.30-4.44 (3H, m, H-5', H-4'), 4.44-4.51 (2H, m, H-2' and H-3'), 6.04 (1H, s, H-1'), 7.73 (1H, s, Th), 8.01 (1H, s, Th), 8.45 (1H, s, H-6); 9.78 (1H, s, CHO); $\delta_C$ (75.5 MHz, $D_2O$) 65.9 (C-5'), 70.4 (C-3'), 75.0 (C-2'), 84.5 (C-4'), 89.5 (C-1'), 101.5, 109.7, 126.1, 139.2, 140.6, 142.2, 145.0 (C—Th+C6+C-5+C-2), 163.6 (C-4), 188.0 (CHO); $\delta_P$ (121 MHz, $D_2O$) −6.5 (d, $J_{P,P}$=20.7 Hz), −11.5 (d, $J_{P,P}$=19.7 Hz), −22.6 (d, $J_{P,P}$=20.1 Hz). m/z (ESI) 592.9448 [M−H]⁻, $C_{14}H_{16}N_2O_{16}P_3$ requires 592.9439.

Fluorescence Studies.
Measurement of Absorbance and Fluorescence Spectra and Determination of Quantum Yields UV absorbance spectra were recorded on a PerkinElmer Lambda 25 UV-Vis spectrometer at ambient temperature in FarUV quartz cells (path length 1.0 cm). Fluorescence spectra were recorded on a PerkinElmer LS-45 spectrometer at ambient temperature in a quartz micro fluorescence cell (path length 1.0 cm).

Quantum Yields

Nucleotide derivatives were serially diluted in $H_2O$ (10, 20, 30, 40 and 50 μM for absorbance measurements, and 0.2, 0.4, 0.6, 0.8, 1 μM for fluorescence measurements), and UV absorbance and fluorescence emission (with $\lambda_{max}$ absorbance=$\lambda_{em}$ fluorescence) were recorded for all samples. To determine quantum yields, for each absorbance and fluorescence spectrum the area under the curve (AUC) was calculated by numerical integration, applying the mid-point rule. For each compound, $AUC_{abs}$ and $AUC_{em}$ were then plotted over compound concentration according to $AUC_{abs}$=A×[conc]+B and $AUC_{em}$=A'×[conc]+B'. From these linear plots, the gradients A and A' were extracted, and for each compound the specific quantum yield φs, under these experimental conditions, was calculated as the ratio A'/A. Quantum yields determined with this protocol for two reference compounds, 2-aminopyridine and L-tryptophan (2-aminopyridine: 0.60; L-tryptophan: 0.14) were in exact agreement with literature values. The quantum yields for reference compounds were used to calculate the general quantum yield φg for each nucleotide analogue, according to φg=$\phi_{ref}$×(A'/A)/(A'/A)$_{ref}$.

Influence of Polarity Over Fluorescence

Fluorescence intensity measurements were performed in NUNC F96 MicroWell polystyrene plates on a BMG labtech PolarStar plate reader equipped with a 350±5 nm absorbance filter and with a 430±5 nm emission filter. 10 μM solutions of 2q' were prepared in HPLC grade water, acetonitrile and isopropanol. Sample assays with various solvent mixtures were incubated during 2 minutes at 30° C. prior to fluorescence measurement. Data were analysed with the help of GraFit version 5.0.10.

Example 6

Results

The spectrophysical properties of various 5-R-UMP analogues are shown below.

TABLE A

Spectrophysical properties of 5-R-UMP analogues (a) from 5-I-U, (b) from UMP.

| 5-R-UMP, R = | Cpd | Yield | λmax (nm) | Em$_{max}$ (nm) | Fluo Intensity at 100 μM (a.u.) |
|---|---|---|---|---|---|
| H[85] | UMP | | 262 | — | |
| Iodo | 1 | 53$^a$, 77$^b$ | 262 | 377 | — |
| Phenyl | 2a | 71 | 278 | 403 | 40 |
| 4-Chlorophenyl | 2b | 66 | 281 | 398 | 78 |
| 3-Nitro-(4-methyl)phenyl | 2c | 79 | 279 | 434 | 6.7 |
| 3-N-Boc-methylaminephenyl | 2d | 69 | 281 | 427 | 11.6 |
| 3-Hydroxyphenyl | 2e | 52 | 285 | — | — |
| 2-Hydroxyphenyl | 2f | 33 | 273 | 415 | 0.9 |
| 2-Naphtyl | 2g | 47 | 221 | 450 | 32.2 |
| 4-Carboxyphenyl | 2h | 60 | 283 | 411 | 17.6 |

TABLE A-continued

Spectrophysical properties of 5-R-UMP analogues (a) from 5-I-U, (b) from UMP.

| 5-R-UMP, R = | Cpd | Yield | λmax (nm) | Em$_{max}$ (nm) | Fluo Intensity at 100 μM (a.u.) |
|---|---|---|---|---|---|
| 4-Trifluorocarbonylphenyl | 2i | 63 | 280 | 383 | 5.3 |
| 5-Methoxy-(3-pyridyl) | 2j | 45 | 289 | 414 | 74.8 |
| 3-Mesylphenyl | 2k | 58 | 278 | 382 | 5.3 |
| 4-Methoxyphenyl | 2l | 57 | 279 | 444 | 603 |
| 2-Furyl | 2m | 57 | 314 | 437 | 497 |
| 5-Formyl-(2-furyl) | 2n | 56 | 348 | 431 | 640 |
| 3-Formyl-(2-thienyl) | 2o | 25 | 267 | 453 | 387 |
| 5-Acetyl-(2-thienyl) | 2p | 31 | 348 | 433 | >650 |
| 5-Formyl-(2-thienyl) | 2q | 61 | 351 | 434 | >650 |

The quantum yields for the brightest fluorophores are given below in Table B.

Example 6

Influence of Microenvironment

Figure 6:
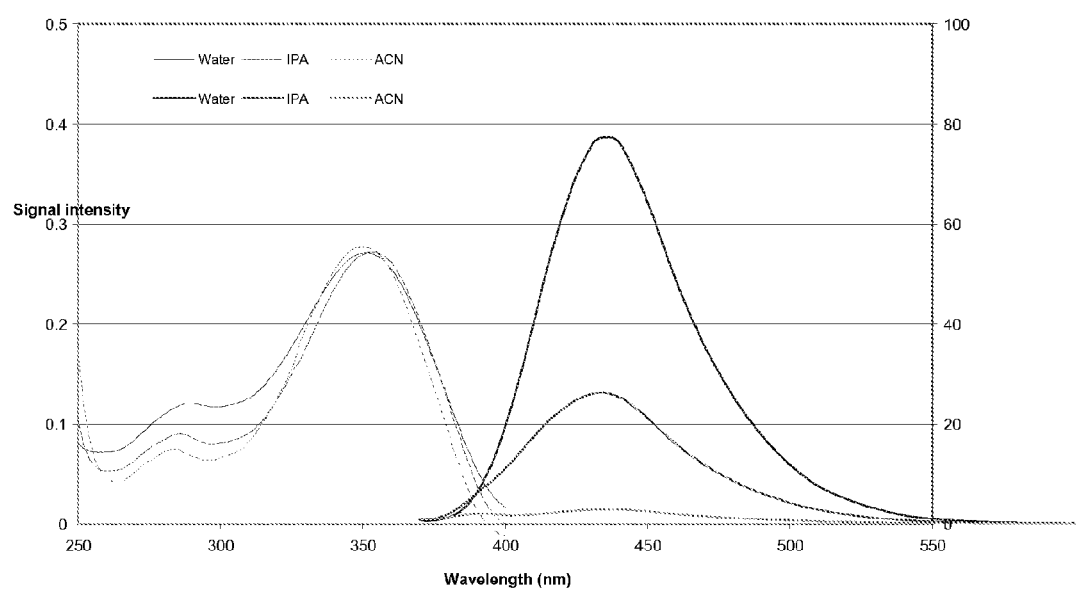
FIG. 6 shows the absorbance (dotted) and fluorescence (plain) spectra of compound 2q' at 200 nM in water (blue), isopropanol (red) and acetonitrile (green); this is described in Example 6 below.

After identifying intense 5-arylated UMP fluorophores and understanding the origin of their fluorescence we investigated the influence of the microenvironment on the fluorescence signal. In order to generate a variety of microenvironments, we prepared 200 nM solutions of 5-(5-formyl-2-thiophene)-uridine 2q' (the nucleoside analogue of 2q) in solvents varying in polarity index: (P): water (P=9), acetonitrile (MeCN, P=5.8) and isopropanol (IPA, P=3.9). We subsequently recorded absorbance and fluorescence signals for these three solutions (see FIG. 6).

Figure 7:
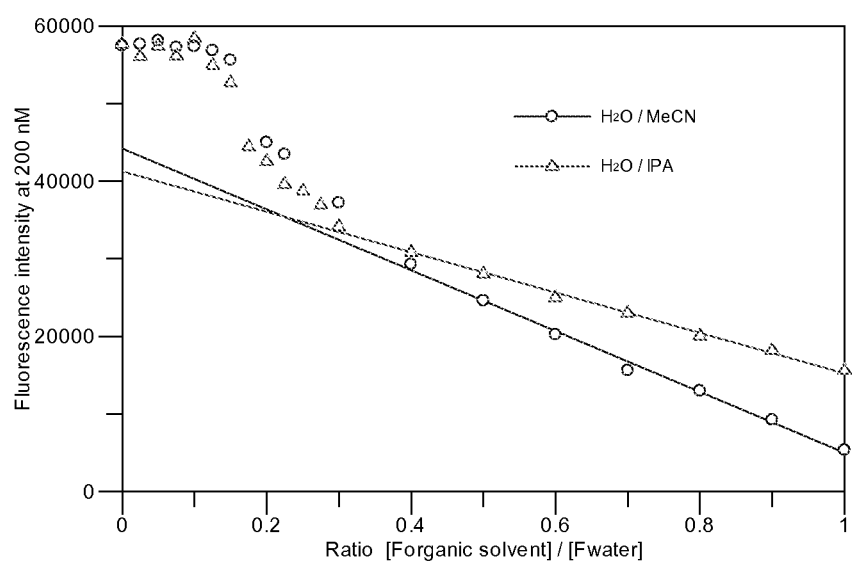
FIG. 7 shows the influence of solvents on fluorescence intensity of compound 2q' at 450 nm FIGS. 8 and 9 together show a scheme for the synthesis of a new C-glycosidic UDP-Gal derivative 2, as described in Example 7 below.

This study revealed that absorbance was unaffected by a change in microenvironment but the fluorescence displayed by 2q' was highly dependent on the solvent source with a fluorescence 20-fold brighter in water than in MeCN. Interestingly, fluorescence and polarity were not directly correlated since we recorded higher fluorescence in IPA than in MeCN despite IPA being less polar than MeCN. Moreover, if polarity is the source of the variation in fluorescence it usually is correlated to a hypsochromic shift in the fluorescence spectra; an effect we did not observe in our measurements. In order to understand the rationale behind this variation in fluorescence we designed a second set of experiments in which the solvent system evolved by small increments and recorded the variation in the fluorescence emitted by 2q' (see FIG. 7).

This experiment confirmed that polarity and fluorescence intensity were not correlated. We observed that linear correlations between solvent source and fluorescence intensity were restricted to solutions containing less than 70% of water for both MeCN/water and IPA/water mixtures. When the water/organic ratio varies from 70 to 100% of water, a fluorescence increase was observed but the previously described trend is lost for a rapid fluorescence increase between 70 and 85% followed by a plateau between 85 and 100% of water.

Example 6

Quantum Yield Calculations

Fluorescent uracil nucleosides and (sugar-)nucleotides can be obtained by connecting a known chromophore/fluorophore via an electronically nonconjugating linker to the natural uracil base (Sinkeldam et al. Chem. Rev. 2010, 110, 2579-2619). The photophysical features of the resulting nucleoside/(sugar-)nucleotide analogue are usually very similar to that of the parent fluorophore (Sinkeldam et al. Chem. Rev. 2010, 110, 2579-2619). In contrast, extending the uracil by electronically conjugating the base to additional aromatic moieties typically generates a new chromophore with unique, and somewhat unpredictable, photophysical characteristics (Sinkeldam et al. Chem. Rev. 2010, 110, 2579-2619). To precisely measure the intensity of the fluorescence emitted by the brightest fluorophores described above, we determined their quantum yield. These measurements were performed in water following the procedure reported by Nighswander-Remper and the results are shown in Table B below. Quantum yield determinations confirmed that 2p and 2q display the highest fluorescence and are 10-fold brighter than any other nucleotide analogues with a compact aryl- or heteroaryl substituent in position 5 that have been reported to date (Sinkeldam et al. Chem. Rev. 2010, 110, 2579-2619). That 2p and 2q absorb and fluoresce at long wavelength is an attractive feature, which makes these fluorophores suitable for analyses in biological environments. Additionally, we found the intensity of the fluorescence emission is conserved for UDP and UTP analogues, thereby providing attractive fluorescence probes candidates for fluorimetric assays.

TABLE B

Quantum yields calculated for the brightest fluorophores.

| 5-R-UMP, R = | Cpd | Q.Y. |
|---|---|---|
| H | UMP | $5.10^{-5}$ |
| 4-Chlorophenyl | 2b | 0.001 |
| 4-Methoxyphenyl | 2l | 0.02 |
| 2-Furan | 2m | 0.04 |
| 5-Formyl-(2-furan) | 2n | 0.04 |
| 3-Formyl-(2-thiophene) | 2o | 0.02 |
| 5-Acetyl-(2-thiophene) | 2p | 0.24 |
| 5-Formyl-(2-thiophene) | 2q | 0.26 |

Example 7

Figure 8:
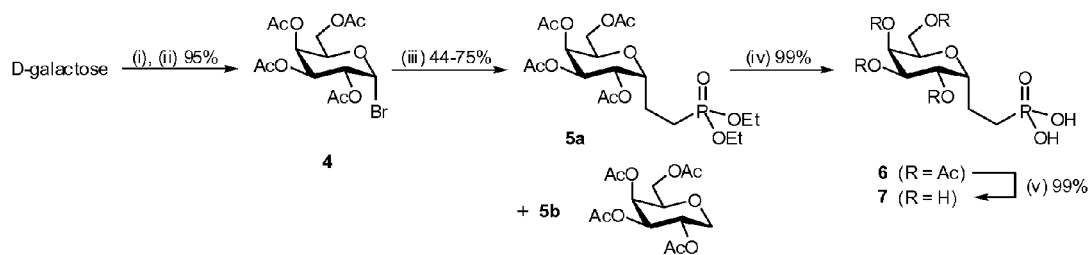

The following Example relates to a new C-glycosidic UDP-Gal derivative 2, as shown in FIG. 9, its synthesis and tests on its physical properties. The full synthesis of 2 from D-galactose is shown in FIGS. 8 (Scheme 1) and 9 (Scheme 2). Scheme 2 in FIG. 9 follows on from Scheme 1 in FIG. 8. The nomenclature in this Example for the compounds is the same as shown in FIGS. 8 and 9.

Example 7

Experimental Section

General Methods.

All reagents were obtained commercially and used as received, including anhydrous solvents over molecular sieves, unless otherwise stated. Anhydrous acetonitrile was obtained after distillation over $CaH_2$ under nitrogen atmosphere. All moisture-sensitive reactions were carried out under an atmosphere of nitrogen in oven-dried glassware. TLC was performed on precoated slides of Silica Gel 60 $F_{254}$ (Merck). Spots were visualised under UV light (254/280 nm) and/or by charring in anisaldehyde stain. Reaction products were characterised by low- and high-resolution mass spectrometry (LR/HR-MS) as well as $^1H$, $^{13}C$ and, in the case of phosphorus-containing molecules, $^{31}P$ NMR spectroscopy.

NMR spectra were recorded at 25° C. on a Varian VXR 400 S spectrometer (400 MHz for $^1$H, 100 MHz for $^{13}$C, 161.9 MHz for $^{31}$P). Chemical shifts (δ) are reported in ppm (parts per million). Assignments of $^1$H signals were made by first-order analysis of 1D spectra, as well as analysis of 2D $^1$H-$^1$H correlation maps (COSY). The $^{13}$C NMR assignments are supported by 2D $^{13}$C-$^1$H correlations maps (HSQC). Preparative chromatography was performed on Silica Gel 60 (particle size 0.063-0.200 mm). Ion-pair and ion-exchange chromatography was performed on a Biologic LP chromatography system equipped with a peristaltic pump and a 254 nm UV Optics Module under the following conditions:
Purification Method 1.

Ion-pair chromatography was performed using Lichroprep RP-18 resin and a standard gradient (unless stated otherwise) of 0-15% MeOH against 0.05 M TEAB (triethylammonium bicarbonate) over a total volume of 480 mL (flow rate: 5 mL/min). Product-containing fractions were combined and reduced to dryness. The residue was co-evaporated repeatedly with methanol to remove residual TEAB.
Purification Method 2.

Anion exchange chromatography was performed on Bioscale™ Mini Macro-Prep High Q cartridges and a gradient of 0-100% 1 M TEAB (pH 7.3) against H$_2$O over a total volume of 480 mL (flow rate: 3 mL/min). Product-containing fractions were combined and reduced to dryness. The residue was co-evaporated repeatedly with methanol to remove residual TEAB.

1,2,3,4,6-penta-O-acetyl-(α,β)-D-galactopyranose

Acetic anhydride acetic (70 mL, 740.5 mmol) was added dropwise to a solution of α-D-galactose (5.0 g, 27.8 mmol) in anhydrous pyridine (70 mL). The reaction was stirred under nitrogen for 20 hours at room temperature, at which point TLC showed the complete disappearance of starting material. The mixture was concentrated under reduced pressure, and volatiles were removed by repeated co-evaporation with toluene. The residue was purified by column chromatography (cyclohexane/EtOAc, 6:4) to give a mixture of anomers (α:β=3:1) of the title compound as a colourless oil (10.5 g, 97%): R$_f$ 0.6 (cyclohexane/EtOAc 1:1); δ$_H$ (400 MHz, CDCl$_3$) 6.34 (d, 1H$_α$, J$_{1,2}$ 1.6 Hz, H-1α), 5.66 (d, 1H$_β$, J$_{1,2}$ 1.6 Hz, H-1β), 5.46 (dd, 1H$_α$, J$_{3,4}$<1.0 Hz, J$_{4,5}$ 1.2 Hz, H-4α), 5.46 (dd, 1H$_β$, J$_{3,4}$ 3.4 Hz, J$_{4,5}$<1.0 Hz, H-4β), 5.33-5.27 (m, 2H$_α$· and 1H$_β$, H-2α, H-3α, H-2β), 5.04 (dd, 1H$_β$, J$_{2,3}$ 10.4 Hz, H-3β), 4.31 (dt, 1H$_α$, J$_{5,6}$ 6.6 Hz, H-5α), 4.15-4.00 (m, 2H$_α$· and 3H$_β$, H-6α, H-6bα, H-5β, H-6β, H-6bβ), 2.12, 2.08, 2.00, 1.98, 1.96, 1.95 (all s, 5H$_α$ and 5H$_β$, 10×C(O)CH$_3$); δ$_C$ (100 MHz, CDCl$_3$) 170.6, 170.4, 170.1, 169.2, 167.2 (5×C=O), 92.3 (C-1β), 89.9 (C-1α), 71.8 (C-5β), 71.0 (C-3β), 68.9 (C-1α), 67.9 (C-2β), 67.5 (C-3α and C4α), 66.9 (C-4β), 66.6 (C-2α), 61.4 (C-6α), 61.2 (C-6β), 21.1, 21.0, 20.9, 20.9, 20.8 (5×C(O)CH$_3$).

2,3,4,6-tetra-O-acetyl-α-D-galactopyranosyl bromide (4)

At 0° C., a solution of hydrogen bromide in acetic acid (33%, 5 mL) was added dropwise to 1,2,3,4,6-penta-O-acetyl-(α,β)-D-galactopyranose (500 mg, 1.28 mmol). After stirring for 2 hours at room temperature, dichloromethane (30 mL) was added to the reaction. The solution was carefully washed with ice-cold water, and the organic layer was dried over MgSO$_4$. The solvent was evaporated under vacuum to afford 1.04 g (98%) of galactosyl bromide 3: R$_f$ 0.45 (cyclohexane/EtOAc 2:1); δ$_H$ (400 MHz, CDCl$_3$) 6.70 (d, 1H, J$_{1,2}$ 3.6 Hz, H-1), 5.52 (dd, 1H, J$_{3,4}$ 3.2 Hz, J$_{4,5}$ 1.2 Hz, H-4), 5.41 (dd, 1H, J$_{2,3}$ 10.4 Hz, H-3), 5.05 (dd, 1H, H-2), 4.49 (m, 1H, H-5), 4.19 (dd, 1H, J$_{6a,6b}$ 11.6 Hz, J$_{5,6}$ 6.0 Hz, H-6a), 4.04 (dd, 1H, J$_{5,6b}$ 6.8 Hz, H-6b), 2.15, 2.12, 2.06, 2.02 (all s, 12H, 4×C(O)CH$_3$); δ$_C$ (100 MHz, CDCl$_3$) 167.2 (4×C=O), 88.3 (C-1), 71.2 (C-5), 68.2, 67.9 (C-3/C-4), 67.2 (C-2), 61.0 (C-6), 20.9, 20.8 (4×C(O)CH$_3$).

Diethyl 2-(2,3,4,6-tetra-O-acetyl-α-D-galactopyranosyl)-ethylphosphonate (5a)

Representative Procedure (Diethylether/$^t$BuOH System):

Under a nitrogen atmosphere, a solution of 4 (274 mg, 0.67 mmol), n-Bu$_3$SnCl (57 μL, 0.21 mmol, 0.3 equiv.), NaBH$_3$CN (95% grade, 65 mg, 1.04 mmol, 1.5 equiv.), diethyl vinylphosphonate (1.1 mL, 6.91 mmol, 10 equiv.), ABCN (110 mg, 0.45 mmol, 0.67 equiv.), and tert-butanol (0.65 mL, 6.91 mmol, 10 equiv.) in diethylether (5 mL) was stirred at reflux temperature (35° C.). After 4 days, TLC (cyclohexane/EtOAc 1:1) showed complete consumption of the starting material and the formation of two new species, the desired diethyl 2-(2,3,4,6-tetra-O-acetyl-α-D-glucopyranosyl)-ethylphosphonate 5a (R$_f$ 0.1) and side product 2,3,4,6-tetra-O-acetyl-β-D-glucopyranose 5b (R$_f$ 0.47). The reaction was concentrated in vacuo, and the oily residue was dissolved in CH$_2$Cl$_2$ (30 mL). The organic solution was washed with water (3×30 mL), dried over MgSO$_4$, and reduced to dryness. The residue was purified by chromatography on a silica gel column, which was eluted first with cyclohexane/EtOAc (1:1) and then with EtOAc/EtOH (20:1), to afford 5a as a syrup (257 mg, 71%): R$_f$ 0.5 (EtOAc/EtOH 20:1); δ$_H$ (400 MHz, CDCl$_3$) 5.37 (dd, 1H, J$_{5,6}$ 3.0 Hz, J$_{6,7}$ 2.8 Hz, H-6), 5.24 (dd, 1H, J$_{3,4}$ 5.2 Hz, J$_{4,5}$ 9.3 Hz, H-4), 5.14 (dd, 1H, J$_{5,6}$ 3.3 Hz, J$_{4,5}$ 9.5 Hz, H-5), 4.22-4.00 (m, 7H, H-3, H-8a, H-8b, 2 OCH$_2$CH$_3$), 3.97 (m, 1H, H-7), 2.09, 2.04, 2.01, 1.98 (all s, 12H, 4×C(O)CH$_3$), 2.98-1.56 (m, 4H, H-1a, H-1b, H-2a, H-2b), 1.29 (dt, 6H, $^4$J$_{H,P}$ 2.8 Hz, J$_{H,H}$ 7.0 Hz, 2 OCH$_2$CH$_3$); δ$_C$ (100 MHz, CDCl$_3$) 170.4, 170.0, 169.9, 169.8 (4×C=O), 72.9 (d, J$_{C,P}$ 17.0 Hz, C-3), 68.3 (C-7), 68.2 (C-4), 67.9 (C-5), 67.6 (C-6), 61.8 (d, $^2$J$_{C,P}$ 6.0 Hz, OCH$_2$CH$_3$), 61.7 (d, $^2$J$_{C,P}$ 5.0 Hz, OCH$_2$CH$_3$), 61.5 (C-8), 22.1 (C-1), 20.7 (4×C(O)CH$_3$), 19.3 (C-2), 16.4 (d, J$_{C,P}$ 6.0 Hz, 2×OCH$_2$CH$_3$); δ$_P$ (161.9 MHz, CDCl$_3$) 32.0. m/z (ESI) 497.1772 [M+H]$^+$, C$_{20}$H$_{33}$O$_{12}$P requires 497.1782. 5b: R$_f$ 0.47 (cyclohexane/EtOAc 1:1); δ$_H$ (400 MHz, CDCl$_3$) 5.35 (dd, 1H, J$_{3,4}$ 3.4 Hz, J$_{6,7}$<1.0 Hz, H-4), 5.11 (dd, 1H, J$_{1a,2}$ 5.5 Hz, J$_{1b,2}$ 10.3 Hz, J$_{2,3}$ 10.3 Hz, H-2), 4.95 (dd, 1H, J$_{3,4}$), 4.10 (dd, 1H, J$_{1a,1b}$ 11.1 Hz, H-1a), 4.00 (d, 2H, J$_{5,6}$ 6.4 Hz, H-6a, H-6b), 3.74 (t, 1H, H-5), 3.20 (dd, 1H, H-1b), 2.06, 1.97, 1.96, 1.91 (all s, 12H, 4×C(O)CH$_3$); δ$_C$ (100 MHz, CDCl$_3$) 170.6, 170.4, 170.3, 170.1 (4×C=O), 75.0 (C-5), 71.6 (C-3), 67.9 (C-4), 67.2 (C-1), 66.5 (C-2), 62.2 (C-6), 20.9, 20.8 (4×C(O)CH$_3$). m/z (ESI) 350.1445 [M+NH$_4$]$^+$, C$_{14}$H$_2$O$_9$ requires 350.1446.

Bis(triethylammonium) 2-(2,3,4,6-tetra-O-acetyl-α-D-galactopyranosyl)-ethylphospho-nate (6)

To a solution of 5a (260 mg, 0.53 mmol) in CH$_3$CN (5 mL) at 0° C., pyridine (450 μL, 5.52 mmol, 10.5 equiv.) was added, followed by Me$_3$SiBr (730 μL, 5.52 mmol, 10.5 equiv.). The solution was stirred at 0° C. for 3 h. The reaction was quenched with H$_2$O/C$_5$H$_5$N (9:1, 5 mL) and the solution was evaporated to dryness. The residue was purified by Purification Method 1 (0-50% MeOH against 0.05 M TEAB) to afford the triethylammonium salt of phosphonic acid 6 in quantitative yield (230 mg, 0.52 mmol): R$_f$ 0.1 (EtOAc/EtOH 20:1); $\delta_H$ (400 MHz, CDCl$_3$) 5.25 (dd, 1H, J$_{5,6}$ and J$_{6,7}$ 2.4 Hz, H-6), 5.15-5.05 (m, 2H, H-4, H-5), 4.14-3.95 (m, 4H, H-3, H-7, H-8a, H-8b), 2.98 (q, 6H, J 7.3 Hz, NC$\underline{H}_2$CH$_3$), 1.85-1.30 (m, 4H, H-1a, H-1b, H-2a, H-2b), 1.06 (t, 7.6H, J 7.3 Hz, NCH$_2$C$\underline{H}_3$); $\delta_C$ (100 MHz, CDCl$_3$) 72.3 (d, J$_{C,P}$ 14.3 Hz, C-3), 68.4, 68.3, 68.2 (C-4/C-5/C-6/C-7), 62.0 (C-8), 46.7 (NC$\underline{H}_2$CH$_3$), 22.5 (d, J$_{C,P}$ 136.4 Hz, C-1), 20.2, 20.0 (4×C(O)C$\underline{H}_3$), 19.3 (C-2), 8.3 (NCH$_2$C$\underline{H}_3$). m/z (ESI) 439.0999 [M-H]$^-$, C$_{16}$H$_{24}$O$_{12}$P requires 439.1011.

Bis(triethylammonium) 2-(α-D-galactopyranosyl)-ethylphosphonate (7)

A solution of 6 (49.3 mg, 0.11 mmol) in H$_2$O/MeOH/Et$_3$N (7:3:1, 11 mL) was stirred for 16 h at room temperature. The reaction was evaporated to dryness and the residual white powder was purified by Purification Method 1 (100% 0.05 M TEAB) to afford the triethylammonium salt of 7 as a colorless foam (30 mg, 99%): R$_f$ 0.2 ($^i$PrOH/H$_2$O/aq. NH$_4$OH 6:3:1); $\delta_H$ (400 MHz, D$_2$O) 3.82-3.70 (m, 3H, H-3, H-6, H-7), 3.59 (dd, 1H, J$_{1,2}$ 3.4 Hz, J$_{2,3}$ 9.5 Hz, H-4), 3.54-3.43 (m, 3H, H-5, H-8a, H-8b), 2.97 (q, J=7.3 Hz, NC$\underline{H}_2$CH$_3$, 1.4 equiv.), 1.70-1.20 (m, 4H, H-1a, H-1b, H-2a, H-2b), 1.04 (t, J=7.3 Hz, NCH$_2$C$\underline{H}_3$, 1.4 equiv.); $\delta_C$ (100 MHz, D$_2$O) 76.2 (d, J$_{C,P}$ 16.3 Hz, C-3), 71.6 (C-7), 69.6, 69.2 (C-5/C-6), 68.3 (C-4), 61.3 (C-8), 46.7 (NC$\underline{H}_2$CH$_3$), 23.9 (d, J$_{C,P}$ 134.2 Hz, C-1), 18.4 (C-2), 8.3 (NCH$_2$C$\underline{H}_3$); $\delta_P$ (161.9 MHz, D$_2$O) 24.9. m/z (ESI) 271.0590 [M-H]$^-$, C$_8$H$_{16}$O$_8$P requires 271.0588.

5-(5-Formylthien-2-yl) UMP phosphoromorpholidate (9)

5-(5-formylthien-2-yl) UMP 8 (134 mg, 0.31 mmol) was dissolved in DMSO and co-evaporated (3×) with DMF to remove residual water. The residue was dissolved in DMSO (1 mL) and morpholine (100 μL, 1.66 mmol) was added to the solution. The mixture was stirred at room temperature for 5 minutes. Dipyridyl disulfide (221 mg, 1.0 mmol) and triphenylphosphine (263 mg, 1.0 mmol) were added in 5 min intervals, and the reaction was stirred for 60 minutes at room temperature. The reaction product was precipitated by addition of NaI in acetone (0.1 M). The supernatant was removed with a pipette. The bright red residue was filtered off, washed with cold acetone, and purified by Purification Method 1 (0-20% MeOH against 0.05 M TEAB) to afford phosphoromorpholidate 9 in 7% yield (17 mg, 0.02 mmol): R$_f$ 0.78 ($^i$PrOH/H$_2$O/aq. NH$_4$OH 6:3:1); $\delta_H$ (400 MHz, D$_2$O) 9.72 (s, 1H, CHO), 8.25 (s, 1H, H-6), 7.93 (d, 1H, J 4.2 Hz, H$_{thienyl}$), 7.60 (d, 1H, J 4.2 Hz, H$_{thienyl}$), 6.02 (d, 1H, J$_{1',2'}$ 4.9 Hz, H-1'), 4.40 (1H, t, J 5.1 Hz, H-2'), 4.32 (1H, t, J 4.8 Hz, H-3'), 4.24-4.15 (1H, m, H-4'), 4.09-4.04 (2H, m, H-5'), 3.47 (m, 4H, 2×CH$_2$), 3.04 (q, J=7.3 Hz, NC$\underline{H}_2$CH$_3$, 3 equiv.), 2.88 (m, 4H, 2×CH$_2$), 1.17 (t, 28.4H, J 7.3 Hz, NCH$_2$C$\underline{H}_3$, 3 equiv.); $\delta_P$ (161.9 MHz, D$_2$O) 10.6.

5-Iodo UMP phosphoromorpholidate (11)

5-Iodo UMP 10 [18] (292 mg, 0.65 mmol) was dissolved in DMSO and co-evaporated (3×) with DMF to remove residual water. The residue was dissolved in DMSO (0.5 mL) and morpholine (400 μL, 4.6 mmol) was added to the solution. The mixture was stirred at room temperature for 5 minutes. Dipyridyl disulfide (500 mg, 2.3 mmol) and triphenylphosphine (600 mg, 2.3 mmol) were added in 5 min intervals, and the reaction was stirred for 60 minutes at room temperature. The reaction product was precipitated by addition of NaI in acetone (0.1 M). The supernatant was removed with a pipette. The colourless residue of crude 11 was filtered off, washed with cold acetone, and used in the next reaction step without further purification.

Bis(triethylammonium) [2-(α-D-galactopyranosyl)-ethylphosphono]-5-iodouridin-5'-yl phosphate (12)

11 (129 mg, 0.25 mmol) and 7 (135 mg, 0.50 mmol, 2 equiv.) were repeatedly co-evaporated with pyridine (3 mL). The residue was dried under high vacuum and dissolved in anhydrous DMF (2 mL). To this solution, tetrazole (0.45 M in CH$_3$CN, 2.8 mL, 1.25 mmol, 5 equiv.) was added under a nitrogen atmosphere. The reaction was stirred at room temperature for 4 days. The reaction was evaporated to dryness and the yellow powder was purified sequentially by Purification Methods 1 and 2 to afford the triethylammonium salt of 12 in 28% yield (87.5 mg, 0.07 mmol): R$_f$ 0.5 ($^i$PrOH/H$_2$O/aq. NH$_4$OH 6:3:1); $\delta_H$ (400 MHz, D$_2$O) 8.24 (s, 1H, H-6), 5.90 (d, 1H, J$_{1',2'}$ 4.6 Hz, H-1'), 4.37-4.31 (m, 2H, H-2', H-3'), 4.27-4.12 (m, 3H, H-4', H-5'a, H-5' b), 4.03-3.88 (m, 3H, H-3", H-4", H-6"), 3.80 (dd, 1H, J$_{5",6}$" 3.3 Hz, J$_{4",5}$" 9.6 Hz, H-5"), 3.77-3.62 (m, 3H, H-7", H-8"a, H-8"b), 3.16 (q, J 7.4 Hz, NC$\underline{H}_2$CH$_3$, 1.7 equiv.), 2.00-1.58 (m, 4H, H-1"a, H-1"b, H-2"a, H-2"b), 1.24 (t, J 7.4 Hz, NCH$_2$C$\underline{H}_3$, 1.7 equiv.); $\delta_C$ (150.9 MHz, D$_2$O) 163.2 (C-4), 151.6 (C-2), 145.9 (C-6), 89.7 (C-1'), 83.4 (d, J$_{C,P}$ 9.0 Hz, C-4'), 75.8 (d, J$_{C,P}$ 16.5 Hz, C-3"), 73.8 (C-2'), 71.5 (0-7"), 69.6 (C-2'), 69.1, 68.6, 68.3 (C-4"/C-5"/C-6"), 64.7 (C-5'), 61.2 (0-8"), 58.6 (C-5), 46.6 (NCH$_2$CH$_3$), 23.9 (d, J$_{C,P}$ 138.0 Hz, C-1"), 18.3 (d, J$_{C,P}$<5 Hz, C-2"), 8.2 (NCH$_2$C$\underline{H}_3$); $\delta_P$ (161.9 MHz, D$_2$O) 22.3 (d, J$_{P,P}$ 26.8 Hz, C$\underline{P}$OPO), -8.7 (d, J$_{P,P}$ 26.8 Hz, CPOP$\underline{O}$). m/z (ESI) 702.9808 [M-M]$^-$, C$_{17}$H$_{27}$IN$_2$O$_{16}$P$_2$ requires 702.9808.

Bis(sodium) [2-(α-D-galactopyranosyl)-ethylphosphono]-5-(5-formylthien-2-yl)uridin-5'-yl phosphate (2)

To a 2-necked round bottom flask charged with 12 (56.7 mg, 2.3 equiv. TEA salts, 0.07 mmol), 5-formylthien-2-ylboronic acid (20 mg, 0.13 mmol, 1.8 equiv.) and Cs$_2$CO$_3$ (39 mg, 0.16 mmol, 2.3 equiv.) was added degassed H$_2$O (5 mL). The flask was purged with N$_2$. TPPTS (2.5 mg, 0.004 mmol, 0.06 equiv.) and Na$_2$Cl$_4$Pd (0.5 mg, 0.002 mmol, 0.025 equiv.) were added, and the reaction was stirred under N$_2$ for 2 h at 55° C. The reaction was cooled to room temperature and filtered through a Millipore syringe filter (0.22 μm, 33 mm). The filtrate was concentrated in vacuo to give a white powder, which was purified sequentially by Purification Methods 1 and 2. Side product 3, resulting from dehydrohalogenation, eluted first (17.3 mg, 2.0 equiv. TEA, 0.02 mmol, 32% yield), followed by cross-coupling product 2 (38 mg, 2.3 equiv. TEA, 0.04 mmol, 59% yield). Purified 2 was converted into its sodium salt form by elution from a Dowex-Na$^+$ column: R$_f$ 0.6 ($^i$PrOH/H$_2$O/aq. NH$_4$OH 6:3:1); $\delta_H$ (400 MHz, D$_2$O) 9.76 (s, 1H, C$\underline{H}$O), 8.44 (s, 1H, H-6), 7.98 (d, 1H, J 4.2 Hz, H$_{thienyl}$), 7.73 (d, 1H, J=4.2 Hz, H$_{thienyl}$), 6.01 (d, 1H, J$_{1',2'}$, 4.8 Hz, H-1'), 4.46-4.39 (m, 2H, H-2', H-3'), 4.33-4.23 (m, 3H, H-4', H-5'a, H-5' b), 3.95-3.89 (m, 2H, H-3", H-4"), 3.85 (dd, 1H, J$_{6",7"}$<1 Hz, H-6"), 3.71 (dd, 1H, J$_{5",6"}$ 3.4 Hz, J$_{4",5"}$ 9.4 Hz, H-5"), 3.67-3.55 (m, 3H, H-7", H-8"a, H-8"b), 1.95-1.53 (m, 4H, H-1"a, H-1"b, H-2"a, H-2"b); $\delta_C$ (150.9 MHz, D$_2$O) 187.1 (C$\underline{H}$O), 163.5 (C-4), 151.2 (C-2), 144.5 (C-6), 141.3, 139.6, 138.3, 125.2, 108.9 (C5, 4×C$_{thienyl}$), 89.1 (C-1'), 83.5 (d, J$_{C,P}$ 8.9 Hz, C-4'), 75.6 (d, J$_{C,P}$ 18.2 Hz, C-3"), 74.2 (C-2'), 71.4 (C-7"), 69.5, 69.5, 69.0 (C-3'/C-5'/C-6"), 68.3 (C-4"), 64.7 (C-5'), 61.1 (0-8"), 23.8 (d, J$_{C,P}$ 140.0 Hz, C-1"), 18.2 (d, $J_{C,P}$<5 Hz, C-2"); $\delta_P$ (161.9 MHz, D$_2$O) 22.2 (d, $J_{P,P}$ 27.4 Hz, CPOPO), −8.4 (d, $J_{P,P}$ 27.4 Hz, CPOPO). m/z (ESI) 687.0651 [M−H]$^-$, C$_{22}$H$_{29}$N$_2$O$_{17}$P$_2$S$_1$ requires 687.0668.

Bis(triethylammonium) [2-(α-D-galactopyranosyl)-ethylphosphono]uridin-5'-yl phos-phate (3) [10]

R$_f$ 0.44 ($^i$PrOH/H$_2$O/aq. NH$_4$OH 6:3:1); $\delta_H$ (400 MHz, D$_2$O) 7.95 (d, 1H, J 8.2 Hz, H-5), 5.94 (m, 2H, H-1', H-6), 4.36-4.32 (m, 2H, H-2', H-3'), 4.26-4.12 (m, 3H, H-4', H-5'a, H-5' b), 4.02-3.91 (m, 3H, H-3", H-4", H-6"), 3.82-3.77 (m, 1H, H-5"), 3.76-3.53 (m, 3H, H-7", H-8"a, H-8"b), 3.16 (q, J 7.4 Hz, NCH$_2$CH$_3$, 3.2 equiv.), 2.00-1.57 (m, 4H, H-1"a, H-1"b, H-2"a, H-2"b), 1.24 (t, J=7.4 Hz, NCH$_2$CH$_3$, 3.2 equiv.); $\delta_P$ (161.9 MHz, D$_2$O) 22.2 (d, $J_{P,P}$ 26.8 Hz, CPOPO), −8.4 (d, $J_{P,P}$ 26.8 Hz, CPOPO).
Enzymology.
*Streptococcus thermophilus* UDP-Gal 4'-epimerase (GalE) was purchased from Calbiochem. For the determination of K$_m$ [UDP-Gal], GalE (15 µL, 2.5 mg/L), UDP-Gal (15 µL, final concentrations: 10 µM-1 mM) and MnCl$_2$ (15 µL, 1 mM) in Tris/HCl buffer (pH 7) were incubated for 15 minutes at 30° C. (total volume 150 µL, all concentrations are final concentrations). For the determination of K$_i$ [2], GalE (15 µL, 10 mg/L), UDP-Gal (15 µL, 232 µM), 2 (15 µL, final concentrations: 10 µM-1 mM) and MnCl$_2$ (15 µL, 1 mM) in Tris/HCl buffer (pH 7) were incubated for 15 minutes at 30° C. (total volume 150 µL, all concentrations are final concentrations). The reactions were stopped by cooling in dry ice. Samples (injection volume 80 µL) were analyzed immediately by HPLC on a PerkinElmer Series 200 machine equipped with a Supelcosil™ LC-18-T column (5 µm, 25 cm×4.6 mm), a column oven (set to 35° C.), and a diode array detector. The following buffers were used for HPLC analysis [25]: buffer A—potassium phosphate (100 mM), tetrabutylammonium bisulfate hydrogen sulfate (8 mM), pH 6.5; buffer B—buffer A/methanol (70/30), pH 6.5. All buffers were filtered through 0.2 µm filters prior to use. The elution gradient was as follows (flow rate: 1.5 mL/min): 5% buffer B for 2 min, 5 to 50% buffer B linearly for 15 min, 50% B for 1 min, 50 to 100% A for 2 min, and 95% A for 5 min. The depletion of UDP-Gal and the formation of UDP-Glc, the product of the epimerization reaction, were monitored at 254 nm. The formation of UDP-Glc was quantified based on peak area, in reference to a UDP-Glc calibration curve, and used for the calculation of kinetic parameters. K$_m$ and v$_{max}$ values were determined by fitting data points to a Michaelis-Menten curve using GraFit 5.0.10. The K$_i$ value of 2 was determined by linear regression analysis (Dixon plot) using 0, 10, 25, 50, 100, 250, 5000 and 1000 µM of inhibitor with 232 µM UDP-Gal in Tris/HCl buffer. All experiments were carried out in triplicate. Control experiments carried out in the absence of enzyme showed no significant degree of chemical hydrolysis (<2% after 3 h).

Example 7

Biological Results—Part A

The new UDP-Gal derivative 2 was evaluated as a potential inhibitor of UDP-Gal 4'-epimerase (GalE, E. C. 5.1.3.2), an enzyme of the Leloir pathway of galactose metabolism. GalE catalyses the interconversion of UDP-Gal and UDP-Glc and plays an important role in the biosynthesis of bacterial cell-surface carbohydrates such as the O-antigen in gram-negative species. In thermophilic bacteria, GalE is involved in the biosynthesis of exopolysaccharides, and overexpression of GalE in *T. thermophilus* resulted in an increased capacity of biofilm production. In addition, the corresponding enzyme in *trypanosoma* species is a validated anti-parasitic drug target. GalE inhibitors are therefore of interest as potential antibacterial and anti-parasitic agents.

Figure 10:
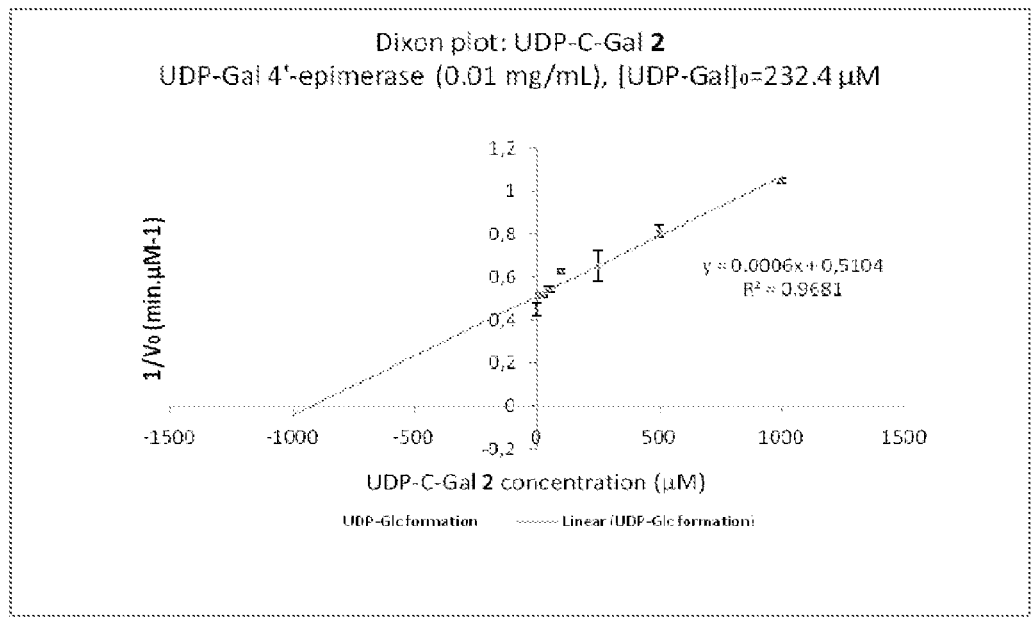
FIG. 10 shows a Dixon plot of the compound UDP-C-Gal 2, which is further described in Example 7 below.

In this study, we used a commercial GalE from *Streptococcus thermophilus* as a model enzyme for the biological characterization of 2. First, we developed an assay protocol that allowed us to follow the GalE-catalysed conversion of UDP-Gal into UDP-Glc by HPLC. For this protocol, we adapted previously published ion-pair conditions for the separation of UDP-Gal and UDP-Glc [see N. Kochanowski, F. Blanchard, R. Cacan, F. Chirat, E. Guedon, A. Marc and J.-L. Goergen, Intracellular nucleotide and nucleotide sugar contents of cultured CHO cells determined by a fast, sensitive, and high-resolution ion-pair RP-HPLC *Anal. Biochem.*, 2006, 348, 243-251, which is incorporated herein by reference in its entirety]. Next, we incubated GalE with the natural substrate UDP-Gal at different concentrations, monitoring the reaction progress with our HPLC protocol. From these experiments, we determined a K$_m$ for UDP-Gal of 233±15 µM. Finally, we co-incubated GalE and UDP-Gal with inhibitor 2. In the presence of the UDP-C-Gal derivative 2, the conversion of UDP-Gal into UDP-Glc was significantly reduced, and we determined a K$_i$ of 426 µM for 2 (see FIG. 10).

Without being bound by theory, two explanations are conceivable for the inhibitory effect of 2 on GalE-catalysed UDP-Gal epimerization: 2 might act either as an alternative substrate of the enzyme, leading to the formation of the corresponding 5-substituted UDP-C-Glc derivative, or as an inhibitor. During the co-incubation experiments, no new peak was observed in the HPLC chromatograms of the enzymatic reactions. This suggests that GalE does not use 2 as a substrate and that 2 may indeed be a true GalE inhibitor.

Example 7

Biological Results—Part B

Figure 11:
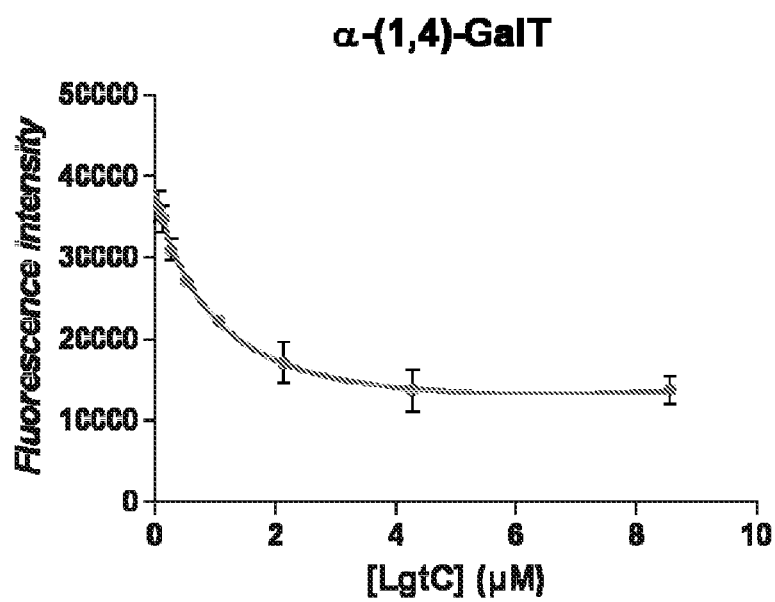
FIG. 11 shows the titration of C-glycosidic fluorophore 2 with a-1.4-GalT; this is described in Example 7 below.
Figure 12:
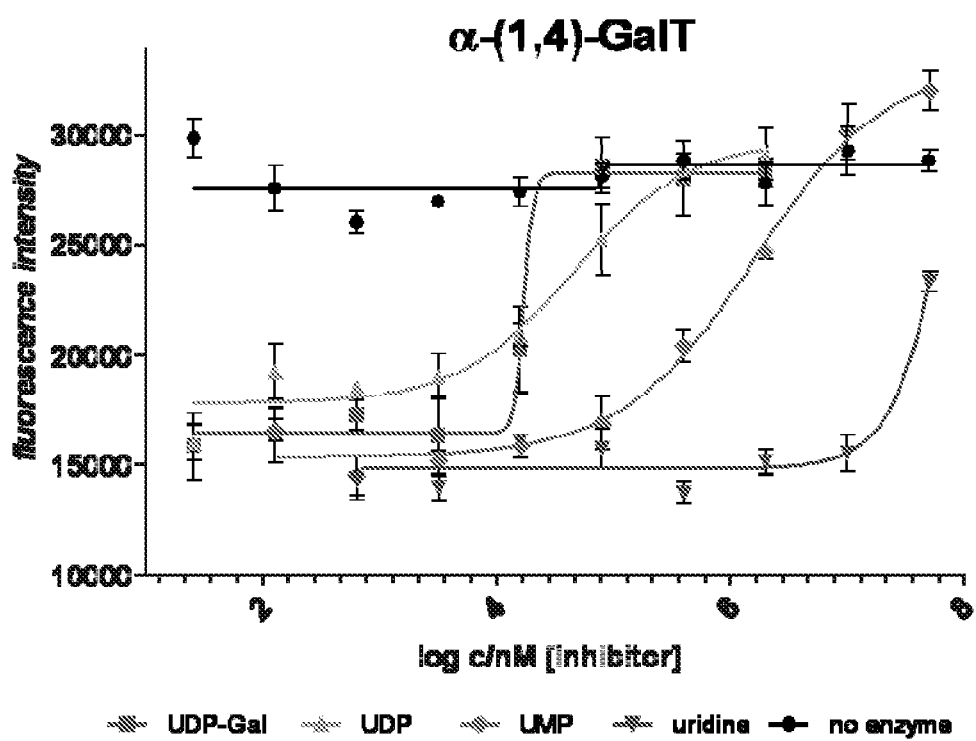
FIG. 12 shows the change in fluorescence of the new C-glycosidic fluorophore 2, in the presence of a-1.4-GalT, upon titration with UDP-Gal, UDP, UMP, or uridine; this is described in Example 7 below.

For the hydrolytically stable C-glycoside analogue 2, we also showed that (i) fluorescence of this compound is quenched upon titration with a bacterial GalT, and (ii) this effect can reversed by titration with UDP-Gal (the natural donor), UDP or, to a lesser extent, UMP. The fluorescence quenching can therefore be exploited to determine the 1050 for UDP-Gal, UDP etc. FIGS. 11 and 12 show these results. The methodology carried out was similar to that for results shown in FIGS. 1*a* & 1*b*.

The present application relates to the following subject matter, as described in the following numbered statements:

A compound of the formula (I):

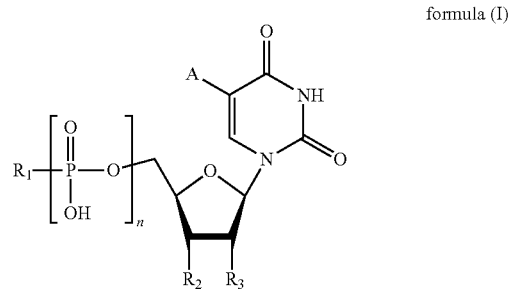

formula (I)

wherein n is 1, 2 or 3;

$R_1$ is selected from —OH, —OPO$_3$H, —OR$_4$, —NHR$_4$;

$R_2$ and $R_3$ are each independently selected from —H, —OH, optionally substituted —O-alkyl and —O-alkanoyl;

$R_4$ is selected from an optionally substituted mono or polysaccharide, -alkyl, -alkenyl, -alkynyl, and L-Z, where L is a linking agent and Z is a binding agent;

A is either (i) a substituted heteroaryl group, the substituent on the heteroaryl group having a double bond conjugated to the heteroaryl group, or (ii) a substituted aryl group, the substituent on the aryl group having a double bond conjugated to the aryl group.

2. A compound according to statement 1, wherein n is 2.

3. A compound according to statement 1 or statement 2, wherein $R_1$ is selected from —OH and —OR$_4$ and $R_4$ is an optionally substituted monosaccharide.

4. A compound according to any one of the preceding statements, wherein the optionally substituted monosaccharide is selected from glucose, galactose, galactosamine, glucosamine, xylose, fucose and glucuronic acid, and acylated derivatives thereof.

5. A compound according to any one of the preceding statements, wherein the substituted heteroaryl group is a substituted thiophene.

6. A compound according to any one of the preceding statements, wherein the substituent on the heteroaryl group is selected from alkenyl and a group of the formula —C(=X)—$R_5$, wherein X is selected from O, S, NH and N-alkyl, and $R_5$ is selected from —H and optionally substituted -alkyl, -alkenyl and -alkynyl.

7. A compound according to any one of the preceding statements, wherein $R_2$ and $R_3$ are each OH.

8. A compound according to any one of the preceding statements, wherein n is 2, $R_1$ is selected from —OH and —OR$_4$ and $R_4$ is an optionally substituted monosaccharide, $R_2$ and $R_3$ are each OH, the substituted heteroaryl group is a substituted thiophene, the substituent on the heteroaryl group is a group of the formula —C(=X)—$R_5$, wherein X is selected from O, S, NH and N-alkyl, and $R_5$ is selected from —H and optionally substituted -alkyl, -alkenyl and -alkynyl.

9. A method for determining the binding affinity of a substance to a glycosyltransferase protein, the method comprising:

contacting in a liquid medium the materials:

a glycosyltransferase protein;

a compound of formula (I) according to any one of statements 1 to 8; and a substance; and, after the contacting, measuring the luminescence of the materials in the liquid medium.

10. A method according to statement 9, wherein the method comprises: providing the glycosyltransferase protein and the compound of formula (I) according to any one of statements 1 to 8 in the liquid medium;

adding the substance to the liquid medium; and measuring the luminescence of the compound of formula (I) before and after adding the substance to the liquid medium to detect a difference in the luminescence.

11. A method according to statement 9, wherein the method comprises:

providing the compound of formula (I) according to any one of statements 1 to 8 and the substance in a liquid medium;

adding the glycosyltransferase protein to the liquid medium; and measuring the luminescence of the compound of formula (I) before and after adding the substance to the liquid medium to detect a difference in the luminescence.

12. A method according to any one of statements 9 to 11, wherein the glycosyltransferase protein is selected from a galactosyltransferase, a N-acetylgalactosyltransferase, a glucosyltransferase, a N-acetylglucosyltransferase, a xylosyltransferase, a glucuronyltransferase, a mannosyltransferase, and a fucosyltransferase.

13. A method according to any one of statements 9 to 12, wherein the liquid medium comprises a protic solvent.

14. A method according to any one of statements 9 to 13, wherein the liquid medium contains a divalent metal ion.

15. A method according to statement 14, wherein the divalent metal ion is $Mn^{2+}$.

16. Use of a compound of formula (I) according to any one of statement 1 to 8 in determining the binding affinity of a substance to a glycosyltransferase protein.

17. A kit for use in the method of any one of statements 9 to 15, the kit comprising one or more containers comprising:

a compound of formula (I) according to any one of statements 1 to 8, and instructions on how to carry out a method for determining the binding affinity of a substance to a glycosyltransferase protein using the compound of formula (I).

18. The kit according to statement 17, which further comprises, optionally in one or more separate containers from the compound of formula (I), (i) a glycosyltransferase protein and/or (ii) a liquid medium suitable for allowing the binding of the compound of formula (I) to the glycosyltransferase protein within the liquid medium.

19. An apparatus for use in the method according to any one of statements 9 to 15, the apparatus comprising a container containing a compound of formula (I) according to the first aspect, and optionally one or more of a liquid medium, a glycosyltransferase protein, and a substance, and wherein the container is adapted such that fluorescence of the compound of formula (I) can be measured.

20. The apparatus according to statement 19, the apparatus further comprising a means for measuring the fluorescence of the compound of formula (I) in the liquid medium.

21. The apparatus according to statement 19 or 20, wherein the container is a multi-well plate for use in a high throughput screening process, at least one the wells containing a compound of formula (I) according to any one of statements 1 to 8, and optionally one or more of a liquid medium, a glycosyltransferase protein, and a substance to be tested.

22. A composition comprising a compound of formula (I) according to any one of statements 1 to 8 and a glycosyltransferase protein.

23. A composition according to statement 22, wherein the composition further comprises a liquid medium.

All publications mentioned herein are incorporated herein by reference.

TABLE E1

Titration experiments with GalT (dilutions E1-E8), in the presence (columns 1-3) or absence (columns 4-6) of $MnCl_2$.

| | 1 | 2 | 3 | 4 | 5 | 6 |
|---|---|---|---|---|---|---|
| A | F + B + M + E1 | F + B + M + E1 | F + B + M + E1 | F + 3 × B + E1 | F + 3 × B + E1 | F + 3 × B + E1 |
| B | F + B + M + E2 | F + B + M + E2 | F + B + M + E2 | F + 3 × B + E2 | F + 3 × B + E2 | F + 3 × B + E2 |
| C | F + B + M + E3 | F + B + M + E3 | F + B + M + E3 | F + 3 × B + E3 | F + 3 × B + E3 | F + 3 × B + E3 |
| D | F + B + M + E4 | F + B + M + E4 | F + B + M + E4 | F + 3 × B + E4 | F + 3 × B + E4 | F + 3 × B + E4 |
| E | F + B + M + E5 | F + B + M + E5 | F + B + M + E5 | F + 3 × B + E5 | F + 3 × B + E5 | F + 3 × B + E5 |
| F | F + B + M + E6 | F + B + M + E6 | F + B + M + E6 | F + 3 × B + E6 | F + 3 × B + E6 | F + 3 × B + E6 |
| G | F + B + M + E7 | F + B + M + E7 | F + B + M + E7 | F + 3 × B + E7 | F + 3 × B + E7 | F + 3 × B + E7 |
| H | F + B + M + E8 | F + B + M + E8 | F + B + M + E8 | F + 3 × B + E8 | F + 3 × B + E8 | F + 3 × B + E8 |

TABLE E2

Titration experiments with $MnCl_2$, (dilutions M1-M8), in the presence (columns 1-3) or absence (columns 4-6) of GalT.

| | 1 | 2 | 3 | 4 | 5 | 6 |
|---|---|---|---|---|---|---|
| A | F + B + E + M1 | F + B + E + M1 | F + B + E + M1 | F + 2 × B + M1 | F + 2 × B + M1 | F + 2 × B + M1 |
| B | F + B + E + M2 | F + B + E + M2 | F + B + E + M2 | F + 2 × B + M2 | F + 2 × B + M2 | F + 2 × B + M2 |
| C | F + B + E + M3 | F + B + E + M3 | F + B + E + M3 | F + 2 × B + M3 | F + 2 × B + M3 | F + 2 × B + M3 |
| D | F + B + E + M4 | F + B + E + M4 | F + B + E + M4 | F + 2 × B + M4 | F + 2 × B + M4 | F + 2 × B + M4 |
| E | F + B + E + M5 | F + B + E + M5 | F + B + E + M5 | F + 2 × B + M5 | F + 2 × B + M5 | F + 2 × B + M5 |
| F | F + B + E + M6 | F + B + E + M6 | F + B + E + M6 | F + 2 × B + M6 | F + 2 × B + M6 | F + 2 × B + M6 |
| G | F + B + E + M7 | F + B + E + M7 | F + B + E + M7 | F + 2 × B + M7 | F + 2 × B + M7 | F + 2 × B + M7 |
| H | F + B + E + M8 | F + B + E + M8 | F + B + E + M8 | F + 2 × B + M8 | F + 2 × B + M8 | F + 2 × B + M8 |

TABLE E3

Competition experiments with UDP-Gal ($I_a$), UDP ($I_b$), UMP ($I_c$) and uridine ($I_d$) at various concentrations.

| | 1 | 2 | 3 | 4 | 5 | 6 | 7 | 8 |
|---|---|---|---|---|---|---|---|---|
| A | F + M + E + $I_a$1 | F + M + E + $I_a$1 | F + M + E + $I_a$1 | F + M + B + $I_a$1 | F + M + E + $I_b$1 | F + M + E + $I_b$1 | F + M + E + $I_b$1 | F + M + B + $I_b$1 |
| B | F + M + E + $I_a$2 | F + M + E + $I_a$2 | F + M + E + $I_a$2 | F + M + B + $I_a$2 | F + M + E + $I_b$2 | F + M + E + $I_b$2 | F + M + E + $I_b$2 | F + M + B + $I_b$2 |
| C | F + M + E + $I_a$3 | F + M + E + $I_a$3 | F + M + E + $I_a$3 | F + M + B + $I_a$3 | F + M + E + $I_b$3 | F + M + E + $I_b$3 | F + M + E + $I_b$3 | F + M + B + $I_b$3 |
| D | F + M + E + $I_a$4 | F + M + E + $I_a$4 | F + M + E + $I_a$4 | F + M + B + $I_a$4 | F + M + E + $I_b$4 | F + M + E + $I_b$4 | F + M + E + $I_b$4 | F + M + B + $I_b$4 |
| E | F + M + E + $I_a$5 | F + M + E + $I_a$5 | F + M + E + $I_a$5 | F + M + B + $I_a$5 | F + M + E + $I_b$5 | F + M + E + $I_b$5 | F + M + E + $I_b$5 | F + M + B + $I_b$5 |
| F | F + M + E + $I_a$6 | F + M + E + $I_a$6 | F + M + E + $I_a$6 | F + M + B + $I_a$6 | F + M + E + $I_b$6 | F + M + E + $I_b$6 | F + M + E + $I_b$6 | F + M + B + $I_b$6 |
| G | F + M + E + $I_a$7 | F + M + E + $I_a$7 | F + M + E + $I_a$7 | F + M + B + $I_a$7 | F + M + E + $I_b$7 | F + M + E + $I_b$7 | F + M + E + $I_b$7 | F + M + B + $I_b$7 |
| H | F + M + E + $I_a$8 | F + M + E + $I_a$8 | F + M + E + $I_a$8 | F + M + B + $I_a$8 | F + M + E + $I_b$8 | F + M + E + $I_b$8 | F + M + E + $I_b$8 | F + M + B + $I_b$8 |

| | 9 | 10 | 11 | 12 | 13 | 14 | 15 | 16 |
|---|---|---|---|---|---|---|---|---|
| A | F + M + E + $I_c$1 | F + M + E + $I_c$1 | F + M + E + $I_c$1 | F + M + B + $I_c$1 | F + M + E + $I_d$1 | F + M + E + $I_d$1 | F + M + E + $I_d$1 | F + M + B + $I_d$1 |
| B | F + M + E + $I_c$2 | F + M + E + $I_c$2 | F + M + E + $I_c$2 | F + M + B + $I_c$2 | F + M + E + $I_d$2 | F + M + E + $I_d$2 | F + M + E + $I_d$2 | F + M + B + $I_d$2 |
| C | F + M + E + $I_c$3 | F + M + E + $I_c$3 | F + M + E + $I_c$3 | F + M + B + $I_c$3 | F + M + E + $I_d$3 | F + M + E + $I_d$3 | F + M + E + $I_d$3 | F + M + B + $I_d$3 |
| D | F + M + E + $I_c$4 | F + M + E + $I_c$4 | F + M + E + $I_c$4 | F + M + B + $I_c$4 | F + M + E + $I_d$4 | F + M + E + $I_d$4 | F + M + E + $I_d$4 | F + M + B + $I_d$4 |
| E | F + M + E + $I_c$5 | F + M + E + $I_c$5 | F + M + E + $I_c$5 | F + M + B + $I_c$5 | F + M + E + $I_d$5 | F + M + E + $I_d$5 | F + M + E + $I_d$5 | F + M + B + $I_d$5 |
| F | F + M + E + $I_c$6 | F + M + E + $I_c$6 | F + M + E + $I_c$6 | F + M + B + $I_c$6 | F + M + E + $I_d$6 | F + M + E + $I_d$6 | F + M + E + $I_d$6 | F + M + B + $I_d$6 |
| G | F + M + E + $I_c$7 | F + M + E + $I_c$7 | F + M + E + $I_c$7 | F + M + B + $I_c$7 | F + M + E + $I_d$7 | F + M + E + $I_d$7 | F + M + E + $I_d$7 | F + M + B + $I_d$7 |
| H | F + M + E + $I_c$8 | F + M + E + $I_c$8 | F + M + E + $I_c$8 | F + M + B + $I_c$8 | F + M + E + $I_d$8 | F + M + E + $I_d$8 | F + M + E + $I_d$8 | F + M + B + $I_d$8 |

TABLE E4

Competition experiments with thiazolidinones (T1-T12) - 1st reading.

|   | 1 | 2 | 3 | 4 | 5 | 6 |
|---|---|---|---|---|---|---|
| A | F + M + B | F + M + B | F + M + U | F + M + U | F + M + B | F + M + B |
| B | F + M + B | F + M + B | F + M + B | F + M + B | F + M + B | F + M + B |
| C | F + M + T1 | F + M + T2 | F + M + T3 | F + M + T4 | F + M + T5 | F + M + T6 |
| D | F + M + T1 | F + M + T2 | F + M + T3 | F + M + T4 | F + M + T5 | F + M + T6 |
| E | F + M + T1 | F + M + T2 | F + M + T3 | F + M + T4 | F + M + T5 | F + M + T6 |
| F | F + M + T1 | F + M + T2 | F + M + T3 | F + M + T4 | F + M + T5 | F + M + T6 |
| G | F + M + T1 | F + M + T2 | F + M + T3 | F + M + T4 | F + M + T5 | F + M + T6 |
| H | F + M + T1 | F + M + T2 | F + M + T3 | F + M + T4 | F + M + T5 | F + M + T6 |

|   | 7 | 8 | 9 | 10 | 11 | 12 |
|---|---|---|---|----|----|----|
| A | F + M + U | F + M + U | F + M + B | F + M + B | F + M + U | F + M + U |
| B | F + M + B | F + M + B | F + M + B | F + M + B | F + M + B | F + M + B |
| C | F + M + T7 | F + M + T8 | F + M + T9 | F + M + T10 | F + M + T11 | F + M + T12 |
| D | F + M + T7 | F + M + T8 | F + M + T9 | F + M + T10 | F + M + T11 | F + M + T12 |
| E | F + M + T7 | F + M + T8 | F + M + T9 | F + M + T10 | F + M + T11 | F + M + T12 |
| F | F + M + T7 | F + M + T8 | F + M + T9 | F + M + T10 | F + M + T11 | F + M + T12 |
| G | F + M + T7 | F + M + T8 | F + M + T9 | F + M + T10 | F + M + T11 | F + M + T12 |
| H | F + M + T7 | F + M + T8 | F + M + T9 | F + M + T10 | F + M + T11 | F + M + T12 |

TABLE E5

Competition experiments with thiazolidinones (T1-T12) - 2nd reading.

|   | 1 | 2 | 3 | 4 | 5 | 6 |
|---|---|---|---|---|---|---|
| A | F + M + B + E1 | F + M + B + E1 | F + M + U + E1 | F + M + U + E1 | F + M + B + E2 | F + M + B + E2 |
| B | F + M + B + T1 | F + M + B + T2 | F + M + B + T3 | F + M + B + T4 | F + M + B + T5 | F + M + B + T6 |
| C | F + M + T1 + E1 | F + M + T2 + E1 | F + M + T3 + E1 | F + M + T4 + E1 | F + M + T5 + E1 | F + M + T6 + E1 |
| D | F + M + T1 + E1 | F + M + T2 + E1 | F + M + T3 + E1 | F + M + T4 + E1 | F + M + T5 + E1 | F + M + T6 + E1 |
| E | F + M + T1 + E2 | F + M + T2 + E2 | F + M + T3 + E2 | F + M + T4 + E2 | F + M + T5 + E2 | F + M + T6 + E2 |
| F | F + M + T1 + E2 | F + M + T2 + E2 | F + M + T3 + E2 | F + M + T4 + E2 | F + M + T5 + E2 | F + M + T6 + E2 |
| G | F + M + T1 + E3 | F + M + T2 + E3 | F + M + T3 + E3 | F + M + T4 + E3 | F + M + T5 + E3 | F + M + T6 + E3 |
| H | F + M + T1 + E3 | F + M + T2 + E3 | F + M + T3 + E3 | F + M + T4 + E3 | F + M + T5 + E3 | F + M + T6 + E3 |

|   | 7 | 8 | 9 | 10 | 11 | 12 |
|---|---|---|---|----|----|----|
| A | F + M + U + E2 | F + M + U + E2 | F + M + B + E3 | F + M + B + E3 | F + M + U + E3 | F + M + U + E3 |
| B | F + M + B + T7 | F + M + B + T8 | F + M + B + T9 | F + M + B + T10 | F + M + B + T11 | F + M + B + T12 |
| C | F + M + T7 + E1 | F + M + T8 + E1 | F + M + T9 + E1 | F + M + T10 + E1 | F + M + T11 + E1 | F + M + T12 + E1 |
| D | F + M + T7 + E1 | F + M + T8 + E1 | F + M + T9 + E1 | F + M + T10 + E1 | F + M + T11 + E1 | F + M + T12 + E1 |
| E | F + M + T7 + E2 | F + M + T8 + E2 | F + M + T9 + E2 | F + M + T10 + E2 | F + M + T11 + E2 | F + M + T12 + E2 |
| F | F + M + T7 + E2 | F + M + T8 + E2 | F + M + T9 + E2 | F + M + T10 + E2 | F + M + T11 + E2 | F + M + T12 + E2 |
| G | F + M + T7 + E3 | F + M + T8 + E3 | F + M + T9 + E3 | F + M + T10 + E3 | F + M + T11 + E3 | F + M + T12 + E3 |
| H | F + M + T7 + E3 | F + M + T8 + E3 | F + M + T9 + E3 | F + M + T10 + E3 | F + M + T11 + E3 | F + M + T12 + E3 |

The invention claimed is:

1. A compound of the formula (I):

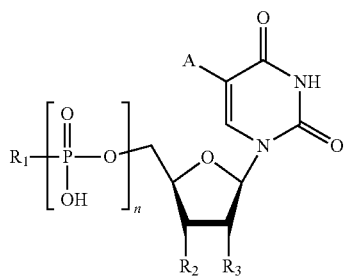

formula (I)

wherein n is 1, 2 or 3;

$R_1$ is selected from —OH, —OPO$_3$H, —OR$_4$, —NHR$_4$, and $R_6$;

$R_2$ and $R_3$ are each independently selected from —H, —OH, optionally substituted —O-alkyl and —O-alkanoyl;

$R_4$ is selected from an optionally substituted mono or polysaccharide, -alkyl, -alkenyl, -alkynyl, and L-Z, where L is a linking agent and Z is a binding agent;

$R_6$ is an optionally substituted hydrocarbon group; and

A is a substituted heteroaryl group, the substituent on the heteroaryl group having a double bond conjugated to the heteroaryl group, wherein the substituted heteroaryl group is selected from a substituted thiophene and a substituted furan and the substituent on the heteroaryl group is selected from alkenyl and a group of the formula —C(=X)—R5, wherein X is selected from O, S, NH and N-alkyl, and R5 is selected from —H and optionally substituted -alkyl, -alkenyl and -alkynyl.

2. The compound according to claim 1, wherein n is 2.

3. The compound according to claim 1, wherein $R_1$ is selected from —OH and —OR$_4$, and $R_4$ is an optionally substituted monosaccharide.

4. The compound according to claim 1, wherein the optionally substituted monosaccharide is selected from glucose, galactose, galactosamine, glucosamine, xylose, fucose and glucuronic acid, and acylated derivatives thereof.

5. The compound according to claim 1, wherein $R_2$ and $R_3$ are each OH.

6. The compound according to claim 1, wherein n is 2, $R_1$ is selected from —OH and —OR$_4$ and $R_4$ is an optionally substituted monosaccharide, and $R_2$ and $R_3$ are each OH.

7. The compound according to claim 1, wherein n is 1 or 2, and $R_1$ is optionally substituted $C_{1\ to\ 3}$ alkyl.

8. The compound according to claim 7, wherein $R_1$ is $C_{1\ to\ 3}$ alkyl substituted with a mono or polysaccharide, and wherein the $C_{1\ to\ 3}$ alkyl is linked to the mono or polysaccharide by a C-glycosidic bond.

9. A method for determining the binding affinity of a substance to a protein selected from a glycosyltransferase protein and a glycoprocessing protein, the method comprising:

contacting in a liquid medium the materials:

a protein selected from a glycosyltransferase protein and a glycoprocessing protein;

a compound of formula (I),

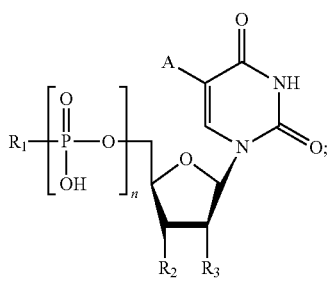

formula (I)

and a substance; and, after the contacting, measuring the luminescence of the materials in the liquid medium, wherein n is 1, 2 or 3;

$R_1$ is selected from —OH, —OPO$_3$H, —OR$_4$, —NHR$_4$, and $R_6$;

$R_2$ and $R_3$ are each independently selected from —H, —OH, optionally substituted —O-alkyl and —O-alkanoyl;

$R_4$ is selected from an optionally substituted mono or polysaccharide, -alkyl, -alkenyl, -alkynyl, and L-Z, where L is a linking agent and Z is a binding agent;

$R_6$ is an optionally substituted hydrocarbon group; and

A is a substituted heteroaryl group, the substituent on the heteroaryl group having a double bond conjugated to the heteroaryl group, wherein the substituted heteroaryl group is selected from a substituted thiophene and a substituted furan and the substituent on the heteroaryl group is selected from alkenyl and a group of the formula —C(=X)—R5, wherein X is selected from O, S, NH and N-alkyl, and R5 is selected from —H and optionally substituted -alkyl, -alkenyl and -alkynyl.

10. The method according to claim 9, wherein the method comprises:

providing the protein selected from a glycosyltransferase protein and a glycoprocessing protein and the compound of formula (I) in the liquid medium;

adding the substance to the liquid medium; and measuring the luminescence of the compound of formula (I) before and after adding the substance to the liquid medium to detect a difference in the luminescence.

11. The method according to claim 9, wherein the method comprises:
providing the compound of formula (I) and the substance in a liquid medium;
adding the protein selected from a glycosyltransferase protein and a glycoprocessing protein into the liquid medium; and
measuring the luminescence of the compound of formula (I) before and after adding the substance to the liquid medium to detect a difference in the luminescence.

12. The method according to claim 9, wherein the glycosyltransferase protein is selected from a galactosyltransferase, a N-acetylgalactosyltransferase, a glucosyltransferase, a N-acetylglucosyltransferase, a xylosyltransferase, a glucuronyltransferase, a mannosyltransferase, and a fucosyltransferase.

13. The method according to claim 9, wherein the glycoprocessing protein is an isomerase that can bind with and/or act upon UDP-galactose and/or UDP-glucose.

14. The method according to according to claim 9, wherein the glycoprocessing protein has an EC number of 5.1 or 5.4.

15. The method according to claim 9, wherein the glycoprocessing protein is a UDP-Gal 4'-epimerase.

16. The method according to claim 9, wherein the liquid medium comprises a protic solvent.

17. The method according to claim 9, wherein the liquid medium contains a divalent metal ion.

18. The method according to claim 17, wherein the divalent metal ion is $Mn^{2+}$.

19. A method for determining binding affinity of a substance to a protein comprising combining the compound of formula (I) according to claim 1 with a protein and determining the binding affinity of the substance to the protein, wherein the protein is selected from a glycosyltransferase protein and a glycoprocessing protein.

20. A kit comprising one or more containers comprising: a compound of formula (I) according to claim 1, and instructions on how to carry out a method for determining the binding affinity of a substance to a protein selected from a glycosyltransferase protein and a glycoprocessing protein using the compound of formula (I).

21. The kit according to claim 20, which further comprises, optionally in one or more separate containers from the compound of formula (I), (i) a protein selected from a glycosyltransferase protein and a glycoprocessing protein, and/or (ii) a liquid medium suitable for allowing the binding of the compound of formula (I) to the protein selected from the glycosyltransferase protein and the glycoprocessing protein within the liquid medium.

22. An apparatus comprising
a container containing a compound of formula (I) according to claim 1, and optionally one or more of a liquid medium, a protein selected from a glycosyltransferase protein and a glycoprocessing protein, and a substance, and wherein the container is adapted such that fluorescence of the compound of formula (I) can be measured.

23. The apparatus according to claim 22, further comprising a means for measuring the fluorescence of the compound of formula (I) in the liquid medium.

24. The apparatus according to claim 22, wherein the container is a multi-well plate for a high throughput screening process, at least one of the wells containing a compound of formula (I), and optionally one or more of a liquid medium, a protein selected from a glycosyltransferase protein and a glycoprocessing protein, and a substance to be tested.

25. A composition comprising a compound of formula (I), formula (I)

and a protein selected from a glycosyltransferase protein and a glycoprocessing protein, wherein
n is 1, 2 or 3;
$R_1$ is selected from —OH, —OPO$_3$H, —NHR$_4$, and $R_6$;
$R_2$ and $R_3$ are each independently selected from —H, —OH, optionally substituted —O-alkyl and —O-alkanoyl;
$R_4$ is selected from an optionally substituted mono or polysaccharide, -alkyl, -alkenyl, -alkynyl, and L-Z, where L is a linking agent and Z is a binding agent;
$R_6$ is an optionally substituted hydrocarbon group; and
A is a substituted heteroaryl group, the substituent on the heteroaryl group having a double bond conjugated to the heteroaryl group, wherein the substituted heteroaryl group is selected from a substituted thiophene and a substituted furan and the substituent on the heteroaryl group is selected from alkenyl and a group of the formula —C(=X)—R5, wherein X is selected from O, S, NH and N-alkyl, and R5 is selected from —H and optionally substituted -alkyl, -alkenyl and -alkynyl.

26. The composition according to claim 25, wherein the glycosyltransferase protein is selected from a galactosyltransferase, a N-acetylgalactosyltransferase, a glucosyltransferase, a N-acetylglucosyltransferase, a xylosyltransferase, a glucuronyltransferase, a mannosyltransferase, and a fucosyltransferase.

27. The composition according to claim 25, wherein the glycoprocessing protein is an isomerase that can bind with and/or act upon UDP-galactose and/or UDP-glucose.

28. The composition according to claim 25, wherein the glycoprocessing protein has an EC number of 5.1 or 5.4.

29. The composition according to claim 25, wherein the glycoprocessing protein is a UDP-Gal 4'-epimerase.

30. The composition according to claim 25, wherein the composition further comprises a liquid medium.

31. The compound according to claim 1, wherein the compound binds to a protein selected from a glycosyltransferase protein and a glycoprocessing protein.

32. The compound according to claim 1, wherein the compound has a fluorescence intensity greater than 100 absorbance units at a concentration of 100 μM of the compound.

* * * * *

SEQUENCE LISTING

<160> NUMBER OF SEQ ID NOS: 33

<210> SEQ ID NO 1
<211> LENGTH: 354
<212> TYPE: PRT
<213> ORGANISM: Homo sapiens

<400> SEQUENCE: 1

```
Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
            20                  25                  30

Gly Tyr Gly Val Leu Ser Pro Arg Ser Leu Met Pro Gly Ser Leu Glu
        35                  40                  45

Arg Gly Phe Cys Met Ala Val Arg Glu Pro Asp His Leu Gln Arg Val
    50                  55                  60
```

```
Ser Leu Pro Arg Met Val Tyr Pro Gln Pro Lys Val Leu Thr Pro Cys
 65                  70                  75                  80

Arg Lys Asp Val Leu Val Val Thr Pro Trp Leu Ala Pro Ile Val Trp
                 85                  90                  95

Glu Gly Thr Phe Asn Ile Asp Ile Leu Asn Glu Gln Phe Arg Leu Gln
            100                 105                 110

Asn Thr Thr Ile Gly Leu Thr Val Phe Ala Ile Lys Lys Tyr Val Ala
        115                 120                 125

Phe Leu Lys Leu Phe Leu Glu Thr Ala Glu Lys His Phe Met Val Gly
    130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Gly
                165                 170                 175

Ala Tyr Lys Arg Trp Gln Asp Val Ser Met Arg Arg Met Glu Met Ile
            180                 185                 190

Ser Asp Phe Cys Glu Arg Arg Phe Leu Ser Glu Val Asp Tyr Leu Val
        195                 200                 205

Cys Val Asp Val Asp Met Glu Phe Arg Asp His Val Gly Val Glu Ile
210                 215                 220

Leu Thr Pro Leu Phe Gly Thr Leu His Pro Ser Phe Tyr Gly Ser Ser
225                 230                 235                 240

Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Met Gly Ala Phe Phe Gly Gly
            260                 265                 270

Ser Val Gln Glu Val Gln Arg Leu Thr Arg Ala Cys His Gln Ala Met
        275                 280                 285

Met Val Asp Gln Ala Asn Gly Ile Glu Ala Val Trp His Asp Glu Ser
290                 295                 300

His Leu Asn Lys Tyr Leu Leu Arg His Lys Pro Thr Lys Val Leu Ser
305                 310                 315                 320

Pro Glu Tyr Leu Trp Asp Gln Gln Leu Leu Gly Trp Pro Ala Val Leu
                325                 330                 335

Arg Lys Leu Arg Phe Thr Ala Val Pro Lys Asn His Gln Ala Val Arg
            340                 345                 350

Asn Pro

<210> SEQ ID NO 2
<211> LENGTH: 354
<212> TYPE: PRT
<213> ORGANISM: Homo sapiens

<400> SEQUENCE: 2

Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
                20                  25                  30

Gly Tyr Gly Val Leu Ser Pro Arg Ser Leu Met Pro Gly Ser Leu Glu
            35                  40                  45

Arg Gly Phe Cys Met Ala Val Arg Glu Pro Asp His Leu Gln Arg Val
        50                  55                  60

Ser Leu Pro Arg Met Val Tyr Pro Gln Pro Lys Val Leu Thr Pro Cys
 65                  70                  75                  80
```

```
Arg Lys Asp Val Leu Val Val Thr Pro Trp Leu Ala Pro Ile Val Trp
                85                  90                  95
Glu Gly Thr Phe Asn Ile Asp Ile Leu Asn Glu Gln Phe Arg Leu Gln
            100                 105                 110
Asn Thr Thr Ile Gly Leu Thr Val Phe Ala Ile Lys Lys Tyr Val Ala
        115                 120                 125
Phe Leu Lys Leu Phe Leu Glu Thr Ala Glu Lys His Phe Met Val Gly
130                 135                 140
His Arg Val His Tyr Tyr Val Phe Thr Asp Gln Pro Ala Ala Val Pro
145                 150                 155                 160
Arg Val Thr Leu Gly Thr Gly Arg Gln Leu Ser Val Leu Glu Val Arg
                165                 170                 175
Ala Tyr Lys Arg Trp Gln Asp Val Ser Met Arg Arg Met Glu Met Ile
            180                 185                 190
Ser Asp Phe Cys Glu Arg Arg Phe Leu Ser Glu Val Asp Tyr Leu Val
        195                 200                 205
Cys Val Asp Val Asp Met Glu Phe Arg Asp His Val Gly Val Glu Ile
210                 215                 220
Leu Thr Pro Leu Phe Gly Thr Leu His Pro Gly Phe Tyr Gly Ser Ser
225                 230                 235                 240
Arg Glu Ala Phe Thr Tyr Glu Arg Arg Pro Gln Ser Gln Ala Tyr Ile
                245                 250                 255
Pro Lys Asp Glu Gly Asp Phe Tyr Tyr Leu Gly Gly Phe Phe Gly Gly
            260                 265                 270
Ser Val Gln Glu Val Gln Arg Leu Thr Arg Ala Cys His Gln Ala Met
        275                 280                 285
Met Val Asp Gln Ala Asn Gly Ile Glu Ala Val Trp His Asp Glu Ser
290                 295                 300
His Leu Asn Lys Tyr Leu Leu Arg His Lys Pro Thr Lys Val Leu Ser
305                 310                 315                 320
Pro Glu Tyr Leu Trp Asp Gln Gln Leu Leu Gly Trp Pro Ala Val Leu
                325                 330                 335
Arg Lys Leu Arg Phe Thr Ala Val Pro Lys Asn His Gln Ala Val Arg
            340                 345                 350
Asn Pro

<210> SEQ ID NO 3
<211> LENGTH: 354
<212> TYPE: PRT
<213> ORGANISM: Artificial
<220> FEATURE:
<223> OTHER INFORMATION: ABBB

<400> SEQUENCE: 3

Met Ala Glu Val Leu Arg Thr Leu Ala Gly Lys Pro Lys Cys His Ala
1               5                   10                  15
Leu Arg Pro Met Ile Leu Phe Leu Ile Met Leu Val Leu Val Leu Phe
                20                  25                  30
Gly Tyr Gly Val Leu Ser Pro Arg Ser Leu Met Pro Gly Ser Leu Glu
            35                  40                  45
Arg Gly Phe Cys Met Ala Val Arg Glu Pro Asp His Leu Gln Arg Val
        50                  55                  60
Ser Leu Pro Arg Met Val Tyr Pro Gln Pro Lys Val Leu Thr Pro Cys
65                  70                  75                  80
Arg Lys Asp Val Leu Val Val Thr Pro Trp Leu Ala Pro Ile Val Trp
```

85                  90                  95
Glu Gly Thr Phe Asn Ile Asp Ile Leu Asn Glu Gln Phe Arg Leu Gln
                100                 105                 110
Asn Thr Thr Ile Gly Leu Thr Val Phe Ala Ile Lys Lys Tyr Val Ala
                115                 120                 125
Phe Leu Lys Leu Phe Leu Glu Thr Ala Glu Lys His Phe Met Val Gly
                130                 135                 140
His Arg Val His Tyr Tyr Val Phe Thr Asp Gln Pro Ala Ala Val Pro
145                 150                 155                 160
Arg Val Thr Leu Gly Thr Gly Arg Gln Leu Ser Val Leu Glu Val Arg
                165                 170                 175
Ala Tyr Lys Arg Trp Gln Asp Val Ser Met Arg Arg Met Glu Met Ile
                180                 185                 190
Ser Asp Phe Cys Glu Arg Arg Phe Leu Ser Glu Val Asp Tyr Leu Val
                195                 200                 205
Cys Val Asp Val Asp Met Glu Phe Arg Asp His Val Gly Val Glu Ile
                210                 215                 220
Leu Thr Pro Leu Phe Gly Thr Leu His Pro Ser Phe Tyr Gly Ser Ser
225                 230                 235                 240
Arg Glu Ala Phe Thr Tyr Glu Arg Arg Pro Gln Ser Gln Ala Tyr Ile
                245                 250                 255
Pro Lys Asp Glu Gly Asp Phe Tyr Tyr Met Gly Ala Phe Phe Gly Gly
                260                 265                 270
Ser Val Gln Glu Val Gln Arg Leu Thr Arg Ala Cys His Gln Ala Met
                275                 280                 285
Met Val Asp Gln Ala Asn Gly Ile Glu Ala Val Trp His Asp Glu Ser
                290                 295                 300
His Leu Asn Lys Tyr Leu Leu Arg His Lys Pro Thr Lys Val Leu Ser
305                 310                 315                 320
Pro Glu Tyr Leu Trp Asp Gln Gln Leu Leu Gly Trp Pro Ala Val Leu
                325                 330                 335
Arg Lys Leu Arg Phe Thr Ala Val Pro Lys Asn His Gln Ala Val Arg
                340                 345                 350
Asn Pro

<210> SEQ ID NO 4
<211> LENGTH: 354
<212> TYPE: PRT
<213> ORGANISM: Artificial
<220> FEATURE:
<223> OTHER INFORMATION: AABB

<400> SEQUENCE: 4

Met Ala Glu Val Leu Arg Thr Leu Ala Gly Lys Pro Lys Cys His Ala
1               5                   10                  15
Leu Arg Pro Met Ile Leu Phe Leu Ile Met Leu Val Leu Val Leu Phe
                20                  25                  30
Gly Tyr Gly Val Leu Ser Pro Arg Ser Leu Met Pro Gly Ser Leu Glu
                35                  40                  45
Arg Gly Phe Cys Met Ala Val Arg Glu Pro Asp His Leu Gln Arg Val
                50                  55                  60
Ser Leu Pro Arg Met Val Tyr Pro Gln Pro Lys Val Leu Thr Pro Cys
65                  70                  75                  80
Arg Lys Asp Val Leu Val Val Thr Pro Trp Leu Ala Pro Ile Val Trp
                85                  90                  95

Glu Gly Thr Phe Asn Ile Asp Ile Leu Asn Glu Gln Phe Arg Leu Gln
            100                 105                 110

Asn Thr Thr Ile Gly Leu Thr Val Phe Ala Ile Lys Lys Tyr Val Ala
            115                 120                 125

Phe Leu Lys Leu Phe Leu Glu Thr Ala Glu Lys His Phe Met Val Gly
130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Arg
                165                 170                 175

Ala Tyr Lys Arg Trp Gln Asp Val Ser Met Arg Met Glu Met Ile
                180                 185                 190

Ser Asp Phe Cys Glu Arg Arg Phe Leu Ser Glu Val Asp Tyr Leu Val
                195                 200                 205

Cys Val Asp Val Asp Met Glu Phe Arg Asp His Val Gly Val Glu Ile
            210                 215                 220

Leu Thr Pro Leu Phe Gly Thr Leu His Pro Gly Phe Tyr Gly Ser Ser
225                 230                 235                 240

Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Met Gly Ala Phe Phe Gly Gly
            260                 265                 270

Ser Val Gln Glu Val Gln Arg Leu Thr Arg Ala Cys His Gln Ala Met
            275                 280                 285

Met Val Asp Gln Ala Asn Gly Ile Glu Ala Val Trp His Asp Glu Ser
            290                 295                 300

His Leu Asn Lys Tyr Leu Leu Arg His Lys Pro Thr Lys Val Leu Ser
305                 310                 315                 320

Pro Glu Tyr Leu Trp Asp Gln Gln Leu Leu Gly Trp Pro Ala Val Leu
                325                 330                 335

Arg Lys Leu Arg Phe Thr Ala Val Pro Lys Asn His Gln Ala Val Arg
                340                 345                 350

Asn Pro

<210> SEQ ID NO 5
<211> LENGTH: 354
<212> TYPE: PRT
<213> ORGANISM: Artificial
<220> FEATURE:
<223> OTHER INFORMATION: AAGlyB

<400> SEQUENCE: 5

Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
                20                  25                  30

Gly Tyr Gly Val Leu Ser Pro Arg Ser Leu Met Pro Gly Ser Leu Glu
            35                  40                  45

Arg Gly Phe Cys Met Ala Val Arg Glu Pro Asp His Leu Gln Arg Val
        50                  55                  60

Ser Leu Pro Arg Met Val Tyr Pro Gln Pro Lys Val Leu Thr Pro Cys
65                  70                  75                  80

Arg Lys Asp Val Leu Val Val Thr Pro Trp Leu Ala Pro Ile Val Trp
                85                  90                  95

```
Glu Gly Thr Phe Asn Ile Asp Ile Leu Asn Glu Gln Phe Arg Leu Gln
                100                 105                 110

Asn Thr Thr Ile Gly Leu Thr Val Phe Ala Ile Lys Lys Tyr Val Ala
            115                 120                 125

Phe Leu Lys Leu Phe Leu Glu Thr Ala Glu Lys His Phe Met Val Gly
        130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Arg
                165                 170                 175

Ala Tyr Lys Arg Trp Gln Asp Val Ser Met Arg Arg Met Glu Met Ile
            180                 185                 190

Ser Asp Phe Cys Glu Arg Arg Phe Leu Ser Glu Val Asp Tyr Leu Val
        195                 200                 205

Cys Val Asp Val Asp Met Glu Phe Arg Asp His Val Gly Val Glu Ile
210                 215                 220

Leu Thr Pro Leu Phe Gly Thr Leu His Pro Gly Phe Tyr Gly Ser Ser
225                 230                 235                 240

Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Gly Gly Ala Phe Phe Gly Gly
            260                 265                 270

Ser Val Gln Glu Val Gln Arg Leu Thr Arg Ala Cys His Gln Ala Met
        275                 280                 285

Met Val Asp Gln Ala Asn Gly Ile Glu Ala Val Trp His Asp Glu Ser
290                 295                 300

His Leu Asn Lys Tyr Leu Leu Arg His Lys Pro Thr Lys Val Leu Ser
305                 310                 315                 320

Pro Glu Tyr Leu Trp Asp Gln Leu Leu Gly Trp Pro Ala Val Leu
                325                 330                 335

Arg Lys Leu Arg Phe Thr Ala Val Pro Lys Asn His Gln Ala Val Arg
            340                 345                 350

Asn Pro

<210> SEQ ID NO 6
<211> LENGTH: 354
<212> TYPE: PRT
<213> ORGANISM: Artificial
<220> FEATURE:
<223> OTHER INFORMATION: GTB - M214T

<400> SEQUENCE: 6

Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
            20                  25                  30

Gly Tyr Gly Val Leu Ser Pro Arg Ser Leu Met Pro Gly Ser Leu Glu
        35                  40                  45

Arg Gly Phe Cys Met Ala Val Arg Glu Pro Asp His Leu Gln Arg Val
    50                  55                  60

Ser Leu Pro Arg Met Val Tyr Pro Gln Pro Lys Val Leu Thr Pro Cys
65                  70                  75                  80

Arg Lys Asp Val Leu Val Val Thr Pro Trp Leu Ala Pro Ile Val Trp
                85                  90                  95

Glu Gly Thr Phe Asn Ile Asp Ile Leu Asn Glu Gln Phe Arg Leu Gln
```

```
            100                 105                 110
Asn Thr Thr Ile Gly Leu Thr Val Phe Ala Ile Lys Lys Tyr Val Ala
        115                 120                 125

Phe Leu Lys Leu Phe Leu Glu Thr Ala Glu Lys His Phe Met Val Gly
        130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Gly
                165                 170                 175

Ala Tyr Lys Arg Trp Gln Asp Val Ser Met Arg Met Glu Met Ile
        180                 185                 190

Ser Asp Phe Cys Glu Arg Arg Phe Leu Ser Glu Val Asp Tyr Leu Val
        195                 200                 205

Cys Val Asp Val Asp Thr Glu Phe Arg Asp His Val Gly Val Glu Ile
        210                 215                 220

Leu Thr Pro Leu Phe Gly Thr Leu His Pro Ser Phe Tyr Gly Ser Ser
225                 230                 235                 240

Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Met Gly Ala Phe Phe Gly Gly
        260                 265                 270

Ser Val Gln Glu Val Gln Arg Leu Thr Arg Ala Cys His Gln Ala Met
        275                 280                 285

Met Val Asp Gln Ala Asn Gly Ile Glu Ala Val Trp His Asp Glu Ser
        290                 295                 300

His Leu Asn Lys Tyr Leu Leu Arg His Lys Pro Thr Lys Val Leu Ser
305                 310                 315                 320

Pro Glu Tyr Leu Trp Asp Gln Gln Leu Leu Gly Trp Pro Ala Val Leu
                325                 330                 335

Arg Lys Leu Arg Phe Thr Ala Val Pro Lys Asn His Gln Ala Val Arg
        340                 345                 350

Asn Pro

<210> SEQ ID NO 7
<211> LENGTH: 354
<212> TYPE: PRT
<213> ORGANISM: Artificial
<220> FEATURE:
<223> OTHER INFORMATION: GTB - M214R

<400> SEQUENCE: 7

Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
                20                  25                  30

Gly Tyr Gly Val Leu Ser Pro Arg Ser Leu Met Pro Gly Ser Leu Glu
            35                  40                  45

Arg Gly Phe Cys Met Ala Val Arg Glu Pro Asp His Leu Gln Arg Val
        50                  55                  60

Ser Leu Pro Arg Met Val Tyr Pro Gln Pro Lys Val Leu Thr Pro Cys
65                  70                  75                  80

Arg Lys Asp Val Leu Val Val Thr Pro Trp Leu Ala Pro Ile Val Trp
                85                  90                  95

Glu Gly Thr Phe Asn Ile Asp Ile Leu Asn Glu Gln Phe Arg Leu Gln
            100                 105                 110
```

Asn Thr Thr Ile Gly Leu Thr Val Phe Ala Ile Lys Lys Tyr Val Ala
            115                 120                 125

Phe Leu Lys Leu Phe Leu Glu Thr Ala Glu Lys His Phe Met Val Gly
        130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Gly
                165                 170                 175

Ala Tyr Lys Arg Trp Gln Asp Val Ser Met Arg Arg Met Glu Met Ile
            180                 185                 190

Ser Asp Phe Cys Glu Arg Arg Phe Leu Ser Glu Val Asp Tyr Leu Val
        195                 200                 205

Cys Val Asp Val Asp Arg Glu Phe Arg Asp His Val Gly Val Glu Ile
210                 215                 220

Leu Thr Pro Leu Phe Gly Thr Leu His Pro Ser Phe Tyr Gly Ser Ser
225                 230                 235                 240

Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Met Gly Ala Phe Phe Gly Gly
            260                 265                 270

Ser Val Gln Glu Val Gln Arg Leu Thr Arg Ala Cys His Gln Ala Met
        275                 280                 285

Met Val Asp Gln Ala Asn Gly Ile Glu Ala Val Trp His Asp Glu Ser
290                 295                 300

His Leu Asn Lys Tyr Leu Leu Arg His Lys Pro Thr Lys Val Leu Ser
305                 310                 315                 320

Pro Glu Tyr Leu Trp Asp Gln Gln Leu Leu Gly Trp Pro Ala Val Leu
                325                 330                 335

Arg Lys Leu Arg Phe Thr Ala Val Pro Lys Asn His Gln Ala Val Arg
            340                 345                 350

Asn Pro

<210> SEQ ID NO 8
<211> LENGTH: 354
<212> TYPE: PRT
<213> ORGANISM: Artificial
<220> FEATURE:
<223> OTHER INFORMATION: GTB - M214V

<400> SEQUENCE: 8

Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
            20                  25                  30

Gly Tyr Gly Val Leu Ser Pro Arg Ser Leu Met Pro Gly Ser Leu Glu
        35                  40                  45

Arg Gly Phe Cys Met Ala Val Arg Glu Pro Asp His Leu Gln Arg Val
    50                  55                  60

Ser Leu Pro Arg Met Val Tyr Pro Gln Pro Lys Val Leu Thr Pro Cys
65                  70                  75                  80

Arg Lys Asp Val Leu Val Val Thr Pro Trp Leu Ala Pro Ile Val Trp
                85                  90                  95

Glu Gly Thr Phe Asn Ile Asp Ile Leu Asn Glu Gln Phe Arg Leu Gln
            100                 105                 110

Asn Thr Thr Ile Gly Leu Thr Val Phe Ala Ile Lys Lys Tyr Val Ala
            115                 120                 125

Phe Leu Lys Leu Phe Leu Glu Thr Ala Glu Lys His Phe Met Val Gly
    130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Gly
                165                 170                 175

Ala Tyr Lys Arg Trp Gln Asp Val Ser Met Arg Arg Met Glu Met Ile
            180                 185                 190

Ser Asp Phe Cys Glu Arg Arg Phe Leu Ser Glu Val Asp Tyr Leu Val
        195                 200                 205

Cys Val Asp Val Asp Val Glu Phe Arg Asp His Val Gly Val Glu Ile
    210                 215                 220

Leu Thr Pro Leu Phe Gly Thr Leu His Pro Ser Phe Tyr Gly Ser Ser
225                 230                 235                 240

Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Met Gly Ala Phe Phe Gly Gly
            260                 265                 270

Ser Val Gln Glu Val Gln Arg Leu Thr Arg Ala Cys His Gln Ala Met
        275                 280                 285

Met Val Asp Gln Ala Asn Gly Ile Glu Ala Val Trp His Asp Glu Ser
    290                 295                 300

His Leu Asn Lys Tyr Leu Leu Arg His Lys Pro Thr Lys Val Leu Ser
305                 310                 315                 320

Pro Glu Tyr Leu Trp Asp Gln Gln Leu Leu Gly Trp Pro Ala Val Leu
                325                 330                 335

Arg Lys Leu Arg Phe Thr Ala Val Pro Lys Asn His Gln Ala Val Arg
            340                 345                 350

Asn Pro

<210> SEQ ID NO 9
<211> LENGTH: 368
<212> TYPE: PRT
<213> ORGANISM: Bos taurus

<400> SEQUENCE: 9

Met Asn Val Lys Gly Lys Val Ile Leu Ser Met Leu Val Val Ser Thr
1               5                   10                  15

Val Ile Val Val Phe Trp Glu Tyr Ile His Ser Pro Glu Gly Ser Leu
                20                  25                  30

Phe Trp Ile Asn Pro Ser Arg Asn Pro Glu Val Gly Gly Ser Ser Ile
            35                  40                  45

Gln Lys Gly Trp Trp Leu Pro Arg Trp Phe Asn Asn Gly Tyr His Glu
    50                  55                  60

Glu Asp Gly Asp Ile Asn Glu Glu Lys Glu Gln Arg Asn Glu Asp Glu
65                  70                  75                  80

Ser Lys Leu Lys Leu Ser Asp Trp Phe Asn Pro Phe Lys Arg Pro Glu
                85                  90                  95

Val Val Thr Met Thr Lys Trp Lys Ala Pro Val Val Trp Glu Gly Thr
            100                 105                 110

Tyr Asn Arg Ala Val Leu Asp Asn Tyr Tyr Ala Lys Gln Lys Ile Thr
        115                 120                 125

Val Gly Leu Thr Val Phe Ala Val Gly Arg Tyr Ile Glu His Tyr Leu
130                 135                 140

Glu Glu Phe Leu Thr Ser Ala Asn Lys His Phe Met Val Gly His Pro
145                 150                 155                 160

Val Ile Phe Tyr Ile Met Val Asp Asp Val Ser Arg Met Pro Leu Ile
                165                 170                 175

Glu Leu Gly Pro Leu Arg Ser Phe Lys Val Phe Lys Ile Lys Pro Glu
                180                 185                 190

Lys Arg Trp Gln Asp Ile Ser Met Met Arg Met Lys Thr Ile Gly Glu
            195                 200                 205

His Ile Val Ala His Ile Gln His Glu Val Asp Phe Leu Phe Cys Met
210                 215                 220

Asp Val Asp Gln Val Phe Gln Asp Lys Phe Gly Val Glu Thr Leu Gly
225                 230                 235                 240

Glu Ser Val Ala Gln Leu Gln Ala Trp Trp Tyr Lys Ala Asp Pro Asn
                245                 250                 255

Asp Phe Thr Tyr Glu Arg Arg Lys Glu Ser Ala Ala Tyr Ile Pro Phe
                260                 265                 270

Gly Glu Gly Asp Phe Tyr Tyr His Ala Ala Ile Phe Gly Gly Thr Pro
            275                 280                 285

Thr Gln Val Leu Asn Ile Thr Gln Glu Cys Phe Lys Gly Ile Leu Lys
290                 295                 300

Asp Lys Lys Asn Asp Ile Glu Ala Gln Trp His Asp Glu Ser His Leu
305                 310                 315                 320

Asn Lys Tyr Phe Leu Leu Asn Lys Pro Thr Lys Ile Leu Ser Pro Glu
                325                 330                 335

Tyr Cys Trp Asp Tyr His Ile Gly Leu Pro Ala Asp Ile Lys Leu Val
                340                 345                 350

Lys Met Ser Trp Gln Thr Lys Glu Tyr Asn Val Val Arg Asn Asn Val
            355                 360                 365

<210> SEQ ID NO 10
<211> LENGTH: 311
<212> TYPE: PRT
<213> ORGANISM: Neisseria meningitidis

<400> SEQUENCE: 10

Met Asp Ile Val Phe Ala Ala Asp Asp Asn Tyr Ala Ala Tyr Leu Cys
1               5                   10                  15

Val Ala Ala Lys Ser Val Glu Ala Ala His Pro Asp Thr Glu Ile Arg
                20                  25                  30

Phe His Val Leu Asp Ala Gly Ile Ser Glu Ala Asn Arg Ala Ala Val
            35                  40                  45

Ala Ala Asn Leu Arg Gly Gly Gly Asn Ile Arg Phe Ile Asp Val
    50                  55                  60

Asn Pro Glu Asp Phe Ala Gly Phe Pro Leu Asn Ile Arg His Ile Ser
65                  70                  75                  80

Ile Thr Thr Tyr Ala Arg Leu Lys Leu Gly Glu Tyr Ile Ala Asp Cys
                85                  90                  95

Asp Lys Val Leu Tyr Leu Asp Ile Asp Val Leu Val Arg Asp Ser Leu
            100                 105                 110

Thr Pro Leu Trp Asp Thr Asp Leu Gly Asp Asn Trp Leu Gly Ala Cys
        115                 120                 125

Ile Asp Leu Phe Val Glu Arg Gln Glu Gly Tyr Lys Gln Lys Ile Gly
130                 135                 140

-continued

```
Met Ala Asp Gly Glu Tyr Tyr Phe Asn Ala Gly Val Leu Leu Ile Asn
145                 150                 155                 160

Leu Lys Lys Trp Arg Arg His Asp Ile Phe Lys Met Ser Cys Glu Trp
                165                 170                 175

Val Glu Gln Tyr Lys Asp Val Met Gln Tyr Gln Asp Gln Asp Ile Leu
            180                 185                 190

Asn Gly Leu Phe Lys Gly Gly Val Cys Tyr Ala Asn Ser Arg Phe Asn
        195                 200                 205

Phe Met Pro Thr Asn Tyr Ala Phe Met Ala Asn Trp Phe Ala Ser Arg
    210                 215                 220

His Thr Asp Pro Leu Tyr Arg Asp Arg Thr Asn Thr Val Met Pro Val
225                 230                 235                 240

Ala Val Ser His Tyr Cys Gly Ser Ala Lys Pro Trp His Arg Asp Cys
                245                 250                 255

Thr Ala Trp Gly Ala Glu Arg Phe Thr Glu Leu Gly Gly Ser Leu Thr
                260                 265                 270

Thr Val Pro Glu Glu Trp Arg Gly Lys Leu Ala Val Pro His Arg Met
            275                 280                 285

Phe Ser Thr Lys Arg Met Leu Gln Arg Trp Arg Lys Leu Ser Ala
        290                 295                 300

Arg Phe Leu Arg Lys Ile Tyr
305                 310

<210> SEQ ID NO 11
<211> LENGTH: 402
<212> TYPE: PRT
<213> ORGANISM: Bos taurus

<400> SEQUENCE: 11

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Val Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Pro Phe Arg Asn Arg Gln
            180                 185                 190

Glu His Leu Lys Tyr Trp Leu Tyr Tyr Leu His Pro Ile Leu Gln Arg
```

|     |     |     |     | 195 |     |     |     |     | 200 |     |     |     |     | 205 |     |     |
| --- | --- | --- | --- | --- | --- | --- | --- | --- | --- | --- | --- | --- | --- | --- | --- | --- |

Gln Gln Leu Asp Tyr Gly Ile Tyr Val Ile Asn Gln Ala Gly Glu Ser
210                     215                     220

Met Phe Asn Arg Ala Lys Leu Leu Asn Val Gly Phe Lys Glu Ala Leu
225                     230                     235                     240

Lys Asp Tyr Asp Tyr Asn Cys Phe Val Phe Ser Asp Val Asp Leu Ile
                        245                     250                     255

Pro Met Asn Asp His Asn Thr Tyr Arg Cys Phe Ser Gln Pro Arg His
                260                     265                     270

Ile Ser Val Ala Met Asp Lys Phe Gly Phe Ser Leu Pro Tyr Val Gln
        275                     280                     285

Tyr Phe Gly Gly Val Ser Ala Leu Ser Lys Gln Gln Phe Leu Ser Ile
290                     295                     300

Asn Gly Phe Pro Asn Asn Tyr Trp Gly Trp Gly Gly Glu Asp Asp Asp
305                     310                     315                     320

Ile Tyr Asn Arg Leu Ala Phe Arg Gly Met Ser Val Ser Arg Pro Asn
                325                     330                     335

Ala Val Ile Gly Lys Cys Arg Met Ile Arg His Ser Arg Asp Lys Lys
                340                     345                     350

Asn Glu Pro Asn Pro Gln Arg Phe Asp Arg Ile Ala His Thr Lys Glu
                355                     360                     365

Thr Met Leu Ser Asp Gly Leu Asn Ser Leu Thr Tyr Met Val Leu Glu
370                     375                     380

Val Gln Arg Tyr Pro Leu Tyr Thr Lys Ile Thr Val Asp Ile Gly Thr
385                     390                     395                     400

Pro Ser

<210> SEQ ID NO 12
<211> LENGTH: 398
<212> TYPE: PRT
<213> ORGANISM: Homo sapiens

<400> SEQUENCE: 12

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Ser
            35                  40                  45

Arg Leu Pro Gln Leu Val Gly Val Ser Thr Pro Leu Gln Gly Gly Ser
        50                  55                  60

Asn Ser Ala Ala Ala Ile Gly Gln Ser Ser Gly Glu Leu Arg Thr Gly
65                  70                  75                  80

Gly Ala Arg Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
                100                 105                 110

Asn Leu Thr Ser Val Pro Val Pro His Thr Thr Ala Leu Ser Leu Pro
            115                 120                 125

Ala Cys Pro Glu Glu Ser Pro Leu Leu Val Gly Pro Met Leu Ile Glu
        130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His

```
                165                 170                 175
Lys Val Ala Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ala Gly Asp Thr Ile Phe Asn Arg
    210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
            245                 250                 255

His Asn Ala Tyr Arg Cys Phe Ser Gln Pro Arg His Ile Ser Val Ala
        260                 265                 270

Met Asp Lys Phe Gly Phe Ser Leu Pro Tyr Val Gln Tyr Phe Gly Gly
    275                 280                 285

Val Ser Ala Leu Ser Lys Gln Gln Phe Leu Thr Ile Asn Gly Phe Pro
290                 295                 300

Asn Asn Tyr Trp Gly Trp Gly Gly Glu Asp Asp Ile Phe Asn Arg
305                 310                 315                 320

Leu Val Phe Arg Gly Met Ser Ile Ser Arg Pro Asn Ala Val Val Gly
            325                 330                 335

Arg Cys Arg Met Ile Arg His Ser Arg Asp Lys Lys Asn Glu Pro Asn
        340                 345                 350

Pro Gln Arg Phe Asp Arg Ile Ala His Thr Lys Glu Thr Met Leu Ser
    355                 360                 365

Asp Gly Leu Asn Ser Leu Thr Tyr Gln Val Leu Asp Val Gln Arg Tyr
370                 375                 380

Pro Leu Tyr Thr Gln Ile Thr Val Asp Ile Gly Thr Pro Ser
385                 390                 395

<210> SEQ ID NO 13
<211> LENGTH: 273
<212> TYPE: PRT
<213> ORGANISM: Helicobacter pylori

<400> SEQUENCE: 13

Met Arg Val Phe Ala Ile Ser Leu Asn Gln Lys Val Cys Asp Thr Phe
1               5                   10                  15

Gly Leu Val Phe Arg Asp Thr Thr Leu Leu Asn Ser Ile Asn Ala
            20                  25                  30

Thr His His Gln Ala Gln Ile Phe Asp Ala Ile Tyr Ser Lys Thr Phe
        35                  40                  45

Glu Gly Gly Leu His Pro Leu Val Lys Lys His Leu His Pro Tyr Phe
    50                  55                  60

Ile Thr Gln Asn Ile Lys Asp Met Gly Ile Thr Thr Asn Leu Ile Ser
65                  70                  75                  80

Glu Val Ser Lys Phe Tyr Tyr Ala Leu Lys Tyr His Ala Lys Phe Met
            85                  90                  95

Ser Leu Gly Glu Leu Gly Cys Tyr Ala Ser His Tyr Ser Leu Trp Glu
        100                 105                 110

Lys Cys Ile Glu Leu Asn Glu Ala Ile Cys Ile Leu Glu Asp Asp Ile
    115                 120                 125

Thr Leu Lys Glu Asp Phe Lys Glu Gly Leu Asp Phe Leu Glu Lys His
130                 135                 140
```

Ile Gln Glu Leu Gly Tyr Ile Arg Leu Met His Leu Leu Tyr Asp Ala
145                 150                 155                 160

Ser Val Lys Ser Glu Pro Leu Ser His Lys Asn His Glu Ile Gln Glu
            165                 170                 175

Arg Val Gly Ile Ile Lys Ala Tyr Ser Glu Gly Val Gly Thr Gln Gly
        180                 185                 190

Tyr Val Ile Thr Pro Lys Ile Ala Lys Val Phe Leu Lys Cys Ser Arg
        195                 200                 205

Lys Trp Val Val Pro Val Asp Thr Ile Met Asp Ala Thr Phe Ile His
210                 215                 220

Gly Val Lys Asn Leu Val Leu Gln Pro Phe Val Ile Ala Asp Asp Glu
225                 230                 235                 240

Gln Ile Ser Thr Ile Ala Arg Lys Glu Glu Pro Tyr Ser Pro Lys Ile
            245                 250                 255

Ala Leu Met Arg Glu Leu His Phe Lys Tyr Leu Lys Tyr Trp Gln Phe
            260                 265                 270

Val

<210> SEQ ID NO 14
<211> LENGTH: 275
<212> TYPE: PRT
<213> ORGANISM: Neisseria meningitidis

<400> SEQUENCE: 14

Met Gln Asn His Val Ile Ser Leu Ala Ser Ala Ala Glu Arg Arg Ala
1               5                   10                  15

His Ile Ala Asp Thr Phe Gly Arg His Gly Ile Pro Phe Gln Phe Phe
            20                  25                  30

Asp Ala Leu Met Pro Ser Glu Arg Leu Glu Gln Ala Met Ala Glu Leu
        35                  40                  45

Val Pro Gly Leu Ser Ala His Pro Tyr Leu Ser Gly Val Glu Lys Ala
    50                  55                  60

Cys Phe Met Ser His Ala Val Leu Trp Lys Gln Ala Leu Asp Glu Gly
65                  70                  75                  80

Leu Pro Tyr Ile Thr Val Phe Glu Asp Val Leu Leu Gly Glu Gly
            85                  90                  95

Ala Glu Lys Phe Leu Ala Glu Asp Ala Trp Leu Gln Glu Arg Phe Asp
            100                 105                 110

Pro Asp Thr Ala Phe Ile Val Arg Leu Glu Thr Met Phe Met His Val
        115                 120                 125

Leu Thr Ser Pro Ser Gly Val Ala Asp Tyr Cys Gly Arg Ala Phe Pro
130                 135                 140

Leu Leu Glu Ser Glu His Trp Gly Thr Ala Gly Tyr Ile Ile Ser Arg
145                 150                 155                 160

Lys Ala Met Arg Phe Phe Leu Asp Arg Phe Ala Ala Leu Pro Pro Glu
            165                 170                 175

Gly Leu His Pro Val Asp Leu Met Met Phe Ser Asp Phe Asp Arg
        180                 185                 190

Glu Gly Met Pro Val Cys Gln Leu Asn Pro Ala Leu Cys Ala Gln Glu
        195                 200                 205

Leu His Tyr Ala Lys Phe His Asp Gln Asn Ser Ala Leu Gly Ser Leu
    210                 215                 220

Ile Glu His Asp Arg Leu Leu Asn Arg Lys Gln Gln Arg Arg Asp Ser
225                 230                 235                 240

```
Pro Ala Asn Thr Phe Lys His Arg Leu Ile Arg Ala Leu Thr Lys Ile
            245                 250                 255

Ser Arg Glu Arg Glu Lys Arg Gln Arg Arg Glu Gln Phe Ile Val
        260                 265                 270

Pro Phe Gln
        275

<210> SEQ ID NO 15
<211> LENGTH: 445
<212> TYPE: PRT
<213> ORGANISM: Homo sapiens

<400> SEQUENCE: 15

Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
            20                  25                  30

Ala Pro Gly Arg Pro Pro Ser Val Ser Ala Leu Asp Gly Asp Pro Ala
                35                  40                  45

Ser Leu Thr Arg Glu Val Ile Arg Leu Ala Gln Asp Ala Glu Val Glu
    50                  55                  60

Leu Glu Arg Gln Arg Gly Leu Leu Gln Gln Ile Gly Asp Ala Leu Ser
65                  70                  75                  80

Ser Gln Arg Gly Arg Val Pro Thr Ala Ala Pro Pro Ala Gln Pro Arg
                85                  90                  95

Val Pro Val Thr Pro Ala Pro Ala Val Ile Pro Ile Leu Val Ile Ala
            100                 105                 110

Cys Asp Arg Ser Thr Val Arg Arg Cys Leu Asp Lys Leu Leu His Tyr
            115                 120                 125

Arg Pro Ser Ala Glu Leu Phe Pro Ile Ile Val Ser Gln Asp Cys Gly
        130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
                165                 170                 175

Arg Lys Phe Gln Gly Tyr Tyr Lys Ile Ala Arg His Tyr Arg Trp Ala
            180                 185                 190

Leu Gly Gln Val Phe Arg Gln Phe Arg Phe Pro Ala Ala Val Val Val
        195                 200                 205

Glu Asp Asp Leu Glu Val Ala Pro Asp Phe Phe Glu Tyr Phe Arg Ala
    210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ala Ser Arg Pro Glu
                245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Lys Ala Phe Trp
        275                 280                 285

Asp Asp Trp Met Arg Arg Pro Glu Gln Arg Gly Arg Ala Cys Ile
    290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335
```

```
Gln Phe Val His Phe Thr Gln Leu Asp Leu Ser Tyr Leu Gln Arg Glu
                340                 345                 350

Ala Tyr Asp Arg Asp Phe Leu Ala Arg Val Tyr Gly Ala Pro Gln Leu
            355                 360                 365

Gln Val Glu Lys Val Arg Thr Asn Asp Arg Lys Glu Leu Gly Glu Val
        370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Thr Phe Gln Phe Arg Gly Arg Val His Leu Ala
            420                 425                 430

Pro Pro Pro Thr Trp Glu Gly Tyr Asp Pro Ser Trp Asn
        435                 440                 445

<210> SEQ ID NO 16
<211> LENGTH: 741
<212> TYPE: PRT
<213> ORGANISM: Homo sapiens

<400> SEQUENCE: 16

Met Ala Leu Phe Thr Pro Trp Lys Leu Ser Ser Gln Lys Leu Gly Phe
1               5                   10                  15

Phe Leu Val Thr Phe Gly Phe Ile Trp Gly Met Met Leu Leu His Phe
                20                  25                  30

Thr Ile Gln Gln Arg Thr Gln Pro Glu Ser Ser Met Leu Arg Glu
            35                  40                  45

Gln Ile Leu Asp Leu Ser Lys Arg Tyr Ile Lys Ala Leu Ala Glu Glu
        50                  55                  60

Asn Arg Asn Val Val Asp Gly Pro Tyr Ala Gly Val Met Thr Ala Tyr
65                  70                  75                  80

Asp Leu Lys Lys Thr Leu Ala Val Leu Leu Asp Asn Ile Leu Gln Arg
                85                  90                  95

Ile Gly Lys Leu Glu Ser Lys Val Asp Asn Leu Val Val Asn Gly Thr
                100                 105                 110

Gly Thr Asn Ser Thr Asn Ser Thr Thr Ala Val Pro Ser Leu Val Ala
            115                 120                 125

Leu Glu Lys Ile Asn Val Ala Asp Ile Ile Asn Gly Ala Gln Glu Lys
        130                 135                 140

Cys Val Leu Pro Pro Met Asp Gly Tyr Pro His Cys Glu Gly Lys Ile
145                 150                 155                 160

Lys Trp Met Lys Asp Met Trp Arg Ser Asp Pro Cys Tyr Ala Asp Tyr
                165                 170                 175

Gly Val Asp Gly Ser Thr Cys Ser Phe Phe Ile Tyr Leu Ser Glu Val
                180                 185                 190

Glu Asn Trp Cys Pro His Leu Pro Trp Arg Ala Lys Asn Pro Tyr Glu
        195                 200                 205

Glu Ala Asp His Asn Ser Leu Ala Glu Ile Arg Thr Asp Phe Asn Ile
    210                 215                 220

Leu Tyr Ser Met Met Lys Lys His Glu Glu Phe Arg Trp Met Arg Leu
225                 230                 235                 240

Arg Ile Arg Arg Met Ala Asp Ala Trp Ile Gln Ala Ile Lys Ser Leu
                245                 250                 255

Ala Glu Lys Gln Asn Leu Glu Lys Arg Lys Arg Lys Lys Val Leu Val
```

His Leu Gly Leu Leu Thr Lys Glu Ser Gly Phe Lys Ile Ala Glu Thr
                    275                 280                 285
Ala Phe Ser Gly Gly Pro Leu Gly Glu Leu Val Gln Trp Ser Asp Leu
                290                 295                 300
Ile Thr Ser Leu Tyr Leu Leu Gly His Asp Ile Arg Ile Ser Ala Ser
305                 310                 315                 320
Leu Ala Glu Leu Lys Glu Ile Met Lys Lys Val Val Gly Asn Arg Ser
                    325                 330                 335
Gly Cys Pro Thr Val Gly Asp Arg Ile Val Glu Leu Ile Tyr Ile Asp
                    340                 345                 350
Ile Val Gly Leu Ala Gln Phe Lys Lys Thr Leu Gly Pro Ser Trp Val
                    355                 360                 365
His Tyr Gln Cys Met Leu Arg Val Leu Asp Ser Phe Gly Thr Glu Pro
                    370                 375                 380
Glu Phe Asn His Ala Asn Tyr Ala Gln Ser Lys Gly His Lys Thr Pro
385                 390                 395                 400
Trp Gly Lys Trp Asn Leu Asn Pro Gln Gln Phe Tyr Thr Met Phe Pro
                    405                 410                 415
His Thr Pro Asp Asn Ser Phe Leu Gly Phe Val Val Glu Gln His Leu
                    420                 425                 430
Asn Ser Ser Asp Ile His His Ile Asn Glu Ile Lys Arg Gln Asn Gln
                    435                 440                 445
Ser Leu Val Tyr Gly Lys Val Asp Ser Phe Trp Lys Asn Lys Lys Ile
                    450                 455                 460
Tyr Leu Asp Ile Ile His Thr Tyr Met Glu Val His Ala Thr Val Tyr
465                 470                 475                 480
Gly Ser Ser Thr Lys Asn Ile Pro Ser Tyr Val Lys Asn His Gly Ile
                    485                 490                 495
Leu Ser Gly Arg Asp Leu Gln Phe Leu Leu Arg Glu Thr Lys Leu Phe
                    500                 505                 510
Val Gly Leu Gly Phe Pro Tyr Glu Gly Pro Ala Pro Leu Glu Ala Ile
                    515                 520                 525
Ala Asn Gly Cys Ala Phe Leu Asn Pro Lys Phe Asn Pro Pro Lys Ser
                    530                 535                 540
Ser Lys Asn Thr Asp Phe Phe Ile Gly Lys Pro Thr Leu Arg Glu Leu
545                 550                 555                 560
Thr Ser Gln His Pro Tyr Ala Glu Val Phe Ile Gly Arg Pro His Val
                    565                 570                 575
Trp Thr Val Asp Leu Asn Asn Gln Glu Glu Val Glu Asp Ala Val Lys
                    580                 585                 590
Ala Ile Leu Asn Gln Lys Ile Glu Pro Tyr Met Pro Tyr Glu Phe Thr
                    595                 600                 605
Cys Glu Gly Met Leu Gln Arg Ile Asn Ala Phe Ile Glu Lys Gln Asp
                    610                 615                 620
Phe Cys His Gly Gln Val Met Trp Pro Pro Leu Ser Ala Leu Gln Val
625                 630                 635                 640
Lys Leu Ala Glu Pro Gly Gln Ser Cys Lys Gln Val Cys Gln Glu Ser
                    645                 650                 655
Gln Leu Ile Cys Glu Pro Ser Phe Phe Gln His Leu Asn Lys Asp Lys
                    660                 665                 670
Asp Met Leu Lys Tyr Lys Val Thr Cys Gln Ser Ser Glu Leu Ala Lys
                    675                 680                 685

```
Asp Ile Leu Val Pro Ser Phe Asp Pro Lys Asn Lys His Cys Val Phe
            690             695             700

Gln Gly Asp Leu Leu Leu Phe Ser Cys Ala Gly Ala His Pro Arg His
705             710             715             720

Gln Arg Val Cys Pro Cys Arg Asp Phe Ile Lys Gly Gln Val Ala Leu
                725             730             735

Cys Lys Asp Cys Leu
            740

<210> SEQ ID NO 17
<211> LENGTH: 1046
<212> TYPE: PRT
<213> ORGANISM: Homo sapiens

<400> SEQUENCE: 17

Met Ala Ser Ser Val Gly Asn Val Ala Asp Ser Thr Glu Pro Thr Lys
1               5                   10                  15

Arg Met Leu Ser Phe Gln Gly Leu Ala Glu Leu Ala His Arg Glu Tyr
            20                  25                  30

Gln Ala Gly Asp Phe Glu Ala Ala Glu Arg His Cys Met Gln Leu Trp
        35                  40                  45

Arg Gln Glu Pro Asp Asn Thr Gly Val Leu Leu Leu Ser Ser Ile
    50                  55                  60

His Phe Gln Cys Arg Arg Leu Asp Arg Ser Ala His Phe Ser Thr Leu
65                  70                  75                  80

Ala Ile Lys Gln Asn Pro Leu Leu Ala Glu Ala Tyr Ser Asn Leu Gly
                85                  90                  95

Asn Val Tyr Lys Glu Arg Gly Gln Leu Gln Glu Ala Ile Glu His Tyr
            100                 105                 110

Arg His Ala Leu Arg Leu Lys Pro Asp Phe Ile Asp Gly Tyr Ile Asn
        115                 120                 125

Leu Ala Ala Ala Leu Val Ala Ala Gly Asp Met Glu Gly Ala Val Gln
    130                 135                 140

Ala Tyr Val Ser Ala Leu Gln Tyr Asn Pro Asp Leu Tyr Cys Val Arg
145                 150                 155                 160

Ser Asp Leu Gly Asn Leu Leu Lys Ala Leu Gly Arg Leu Glu Glu Ala
                165                 170                 175

Lys Ala Cys Tyr Leu Lys Ala Ile Glu Thr Gln Pro Asn Phe Ala Val
            180                 185                 190

Ala Trp Ser Asn Leu Gly Cys Val Phe Asn Ala Gln Gly Glu Ile Trp
        195                 200                 205

Leu Ala Ile His His Phe Glu Lys Ala Val Thr Leu Asp Pro Asn Phe
    210                 215                 220

Leu Asp Ala Tyr Ile Asn Leu Gly Asn Val Leu Lys Glu Ala Arg Ile
225                 230                 235                 240

Phe Asp Arg Ala Val Ala Ala Tyr Leu Arg Ala Leu Ser Leu Ser Pro
                245                 250                 255

Asn His Ala Val Val His Gly Asn Leu Ala Cys Val Tyr Tyr Glu Gln
            260                 265                 270

Gly Leu Ile Asp Leu Ala Ile Asp Thr Tyr Arg Arg Ala Ile Glu Leu
        275                 280                 285

Gln Pro His Phe Pro Asp Ala Tyr Cys Asn Leu Ala Asn Ala Leu Lys
    290                 295                 300

Glu Lys Gly Ser Val Ala Glu Ala Glu Asp Cys Tyr Asn Thr Ala Leu
```

```
                305                 310                 315                 320
Arg Leu Cys Pro Thr His Ala Asp Ser Leu Asn Asn Leu Ala Asn Ile
                325                 330                 335
Lys Arg Glu Gln Gly Asn Ile Glu Glu Ala Val Arg Leu Tyr Arg Lys
                340                 345                 350
Ala Leu Glu Val Phe Pro Glu Phe Ala Ala His Ser Asn Leu Ala
                355                 360                 365
Ser Val Leu Gln Gln Gln Gly Lys Leu Gln Glu Ala Leu Met His Tyr
            370                 375                 380
Lys Glu Ala Ile Arg Ile Ser Pro Thr Phe Ala Asp Ala Tyr Ser Asn
385                 390                 395                 400
Met Gly Asn Thr Leu Lys Glu Met Gln Asp Val Gln Gly Ala Leu Gln
                405                 410                 415
Cys Tyr Thr Arg Ala Ile Gln Ile Asn Pro Ala Phe Ala Asp Ala His
                420                 425                 430
Ser Asn Leu Ala Ser Ile His Lys Asp Ser Gly Asn Ile Pro Glu Ala
            435                 440                 445
Ile Ala Ser Tyr Arg Thr Ala Leu Lys Leu Lys Pro Asp Phe Pro Asp
450                 455                 460
Ala Tyr Cys Asn Leu Ala His Cys Leu Gln Ile Val Cys Asp Trp Thr
465                 470                 475                 480
Asp Tyr Asp Glu Arg Met Lys Lys Leu Val Ser Ile Val Ala Asp Gln
                485                 490                 495
Leu Glu Lys Asn Arg Leu Pro Ser Val His Pro His His Ser Met Leu
                500                 505                 510
Tyr Pro Leu Ser His Gly Phe Arg Lys Ala Ile Ala Glu Arg His Gly
            515                 520                 525
Asn Leu Cys Leu Asp Lys Ile Asn Val Leu His Lys Pro Pro Tyr Glu
            530                 535                 540
His Pro Lys Asp Leu Lys Leu Ser Asp Gly Arg Leu Arg Val Gly Tyr
545                 550                 555                 560
Val Ser Ser Asp Phe Gly Asn His Pro Thr Ser His Leu Met Gln Ser
                565                 570                 575
Ile Pro Gly Met His Asn Pro Asp Lys Phe Glu Val Phe Cys Tyr Ala
            580                 585                 590
Leu Ser Pro Asp Asp Gly Thr Asn Phe Arg Val Lys Val Met Ala Glu
            595                 600                 605
Ala Asn His Phe Ile Asp Leu Ser Gln Ile Pro Cys Asn Gly Lys Ala
            610                 615                 620
Ala Asp Arg Ile His Gln Asp Gly Ile His Ile Leu Val Asn Met Asn
625                 630                 635                 640
Gly Tyr Thr Lys Gly Ala Arg Asn Glu Leu Phe Ala Leu Arg Pro Ala
                645                 650                 655
Pro Ile Gln Ala Met Trp Leu Gly Tyr Pro Gly Thr Ser Gly Ala Leu
                660                 665                 670
Phe Met Asp Tyr Ile Ile Thr Asp Gln Glu Thr Ser Pro Ala Glu Val
            675                 680                 685
Ala Glu Gln Tyr Ser Glu Lys Leu Ala Tyr Met Pro His Thr Phe Phe
            690                 695                 700
Ile Gly Asp His Ala Asn Met Phe Pro His Leu Lys Lys Lys Ala Val
705                 710                 715                 720
Ile Asp Phe Lys Ser Asn Gly His Ile Tyr Asp Asn Arg Ile Val Leu
                725                 730                 735
```

```
Asn Gly Ile Asp Leu Lys Ala Phe Leu Asp Ser Leu Pro Asp Val Lys
            740                 745                 750
Ile Val Lys Met Lys Cys Pro Asp Gly Gly Asp Asn Ala Asp Ser Ser
        755                 760                 765
Asn Thr Ala Leu Asn Met Pro Val Ile Pro Met Asn Thr Ile Ala Glu
    770                 775                 780
Ala Val Ile Glu Met Ile Asn Arg Gly Gln Ile Gln Ile Thr Ile Asn
785                 790                 795                 800
Gly Phe Ser Ile Ser Asn Gly Leu Ala Thr Thr Gln Ile Asn Asn Lys
                805                 810                 815
Ala Ala Thr Gly Glu Glu Val Pro Arg Thr Ile Ile Val Thr Thr Arg
            820                 825                 830
Ser Gln Tyr Gly Leu Pro Glu Asp Ala Ile Val Tyr Cys Asn Phe Asn
        835                 840                 845
Gln Leu Tyr Lys Ile Asp Pro Ser Thr Leu Gln Met Trp Ala Asn Ile
    850                 855                 860
Leu Lys Arg Val Pro Asn Ser Val Leu Trp Leu Arg Phe Pro Ala
865                 870                 875                 880
Val Gly Glu Pro Asn Ile Gln Gln Tyr Ala Gln Asn Met Gly Leu Pro
                885                 890                 895
Gln Asn Arg Ile Ile Phe Ser Pro Val Ala Pro Lys Glu His Val
            900                 905                 910
Arg Arg Gly Gln Leu Ala Asp Val Cys Leu Asp Thr Pro Leu Cys Asn
        915                 920                 925
Gly His Thr Thr Gly Met Asp Val Leu Trp Ala Gly Thr Pro Met Val
    930                 935                 940
Thr Met Pro Gly Glu Thr Leu Ala Ser Arg Val Ala Ala Ser Gln Leu
945                 950                 955                 960
Thr Cys Leu Gly Cys Leu Glu Leu Ile Ala Lys Asn Arg Gln Glu Tyr
                965                 970                 975
Glu Asp Ile Ala Val Lys Leu Gly Thr Asp Leu Glu Tyr Leu Lys Lys
            980                 985                 990
Val Arg Gly Lys Val Trp Lys Gln Arg Ile Ser Ser Pro Leu Phe Asn
        995                 1000                1005
Thr Lys Gln Tyr Thr Met Glu Leu Glu Arg Leu Tyr Leu Gln Met
    1010                1015                1020
Trp Glu His Tyr Ala Ala Gly Asn Lys Pro Asp His Met Ile Lys
    1025                1030                1035
Pro Val Glu Val Thr Glu Ser Ala
    1040                1045

<210> SEQ ID NO 18
<211> LENGTH: 355
<212> TYPE: PRT
<213> ORGANISM: Escherichia coli

<400> SEQUENCE: 18

Met Ser Gly Gln Gly Lys Arg Leu Met Val Met Ala Gly Gly Thr Gly
1               5                   10                  15
Gly His Val Phe Pro Gly Leu Ala Val Ala His His Leu Met Ala Gln
                20                  25                  30
Gly Trp Gln Val Arg Trp Leu Gly Thr Ala Asp Arg Met Glu Ala Asp
            35                  40                  45
Leu Val Pro Lys His Gly Ile Glu Ile Asp Phe Ile Arg Ile Ser Gly
```

```
            50                  55                  60
Leu Arg Gly Lys Gly Ile Lys Ala Leu Ile Ala Ala Pro Leu Arg Ile
 65                  70                  75                  80

Phe Asn Ala Trp Arg Gln Ala Arg Ala Ile Met Lys Ala Tyr Lys Pro
                 85                  90                  95

Asp Val Val Leu Gly Met Gly Tyr Val Ser Gly Pro Gly Gly Leu
                100                 105                 110

Ala Ala Trp Ser Leu Gly Ile Pro Val Val Leu His Glu Gln Asn Gly
                115                 120                 125

Ile Ala Gly Leu Thr Asn Lys Trp Leu Ala Lys Ile Ala Thr Lys Val
            130                 135                 140

Met Gln Ala Phe Pro Gly Ala Phe Pro Asn Ala Glu Val Val Gly Asn
145                 150                 155                 160

Pro Val Arg Thr Asp Val Leu Ala Leu Pro Leu Pro Gln Gln Arg Leu
                165                 170                 175

Ala Gly Arg Glu Gly Pro Val Arg Val Leu Val Val Gly Gly Ser Gln
                180                 185                 190

Gly Ala Arg Ile Leu Asn Gln Thr Met Pro Gln Val Ala Ala Lys Leu
            195                 200                 205

Gly Asp Ser Val Thr Ile Trp His Gln Ser Gly Lys Gly Ser Gln Gln
210                 215                 220

Ser Val Glu Gln Ala Tyr Ala Glu Ala Gly Gln Pro Gln His Lys Val
225                 230                 235                 240

Thr Glu Phe Ile Asp Asp Met Ala Ala Tyr Ala Trp Ala Asp Val
                245                 250                 255

Val Val Cys Arg Ser Gly Ala Leu Thr Val Ser Glu Ile Ala Ala Ala
                260                 265                 270

Gly Leu Pro Ala Leu Phe Val Pro Phe Gln His Lys Asp Arg Gln Gln
                275                 280                 285

Tyr Trp Asn Ala Leu Pro Leu Glu Lys Ala Gly Ala Ala Lys Ile Ile
            290                 295                 300

Glu Gln Pro Gln Leu Ser Val Asp Ala Val Ala Asn Thr Leu Ala Gly
305                 310                 315                 320

Trp Ser Arg Glu Thr Leu Leu Thr Met Ala Glu Arg Ala Arg Ala Ala
                325                 330                 335

Ser Ile Pro Asp Ala Thr Glu Arg Val Ala Asn Glu Val Ser Arg Val
                340                 345                 350

Ala Arg Ala
        355

<210> SEQ ID NO 19
<211> LENGTH: 256
<212> TYPE: PRT
<213> ORGANISM: Bacillus subtilis

<400> SEQUENCE: 19

Met Pro Lys Val Ser Val Ile Met Thr Ser Tyr Asn Lys Ser Asp Tyr
 1               5                  10                  15

Val Ala Lys Ser Ile Ser Ser Ile Leu Ser Gln Thr Phe Ser Asp Phe
                20                  25                  30

Glu Leu Phe Ile Met Asp Asp Asn Ser Asn Glu Glu Thr Leu Asn Val
            35                  40                  45

Ile Arg Pro Phe Leu Asn Asp Asn Arg Val Arg Phe Tyr Gln Ser Asp
         50                  55                  60
```

```
Ile Ser Gly Val Lys Glu Arg Thr Glu Lys Thr Arg Tyr Ala Ala Leu
 65                  70                  75                  80

Ile Asn Gln Ala Ile Glu Met Ala Glu Gly Glu Tyr Ile Thr Tyr Ala
                 85                  90                  95

Thr Asp Asp Asn Ile Tyr Met Pro Asp Arg Leu Leu Lys Met Val Arg
            100                 105                 110

Glu Leu Asp Thr His Pro Glu Lys Ala Val Ile Tyr Ser Ala Ser Lys
        115                 120                 125

Thr Tyr His Leu Asn Glu Asn Arg Asp Ile Val Lys Glu Thr Val Arg
    130                 135                 140

Pro Ala Ala Gln Val Thr Trp Asn Ala Pro Cys Ala Ile Asp His Cys
145                 150                 155                 160

Ser Val Met His Arg Tyr Ser Val Leu Glu Lys Val Lys Glu Lys Phe
                165                 170                 175

Gly Ser Tyr Trp Asp Glu Ser Pro Ala Phe Tyr Arg Ile Gly Asp Ala
            180                 185                 190

Arg Phe Phe Trp Arg Val Asn His Phe Tyr Pro Phe Tyr Pro Leu Asp
        195                 200                 205

Glu Glu Leu Asp Leu Asn Tyr Ile Thr Asp Gln Ser Ile His Phe Gln
    210                 215                 220

Leu Phe Glu Leu Glu Lys Asn Glu Phe Val Arg Asn Leu Pro Pro Gln
225                 230                 235                 240

Arg Asn Cys Arg Glu Leu Arg Glu Ser Leu Lys Lys Leu Gly Met Gly
                245                 250                 255

<210> SEQ ID NO 20
<211> LENGTH: 372
<212> TYPE: PRT
<213> ORGANISM: Homo sapiens

<400> SEQUENCE: 20

Met Ser Arg Leu Leu Gly Gly Thr Leu Glu Arg Val Cys Lys Ala Val
  1               5                  10                  15

Leu Leu Leu Cys Leu Leu His Phe Leu Val Ala Val Ile Leu Tyr Phe
                 20                  25                  30

Asp Val Tyr Ala Gln His Leu Ala Phe Phe Ser Arg Phe Ser Ala Arg
             35                  40                  45

Gly Pro Ala His Ala Leu His Pro Ala Ser Ser Ser Ser Ser Ser Ser
         50                  55                  60

Ser Asn Cys Ser Arg Pro Asn Ala Thr Ala Ser Ser Ser Gly Leu Pro
 65                  70                  75                  80

Glu Val Pro Ser Ala Leu Pro Gly Pro Thr Ala Pro Thr Leu Pro Pro
                 85                  90                  95

Cys Pro Asp Ser Pro Pro Gly Leu Val Gly Arg Leu Leu Ile Glu Phe
            100                 105                 110

Thr Ser Pro Met Pro Leu Glu Arg Val Gln Arg Glu Asn Pro Gly Val
        115                 120                 125

Leu Met Gly Gly Arg Tyr Thr Pro Pro Asp Cys Thr Pro Ala Gln Thr
    130                 135                 140

Val Ala Val Ile Ile Pro Phe Arg His Arg Glu His Leu Arg Tyr
145                 150                 155                 160

Trp Leu His Tyr Leu His Pro Ile Leu Arg Arg Gln Arg Leu Arg Tyr
                165                 170                 175

Gly Val Tyr Val Ile Asn Gln His Gly Glu Asp Thr Phe Asn Arg Ala
            180                 185                 190
```

-continued

```
Lys Leu Leu Asn Val Gly Phe Leu Glu Ala Leu Lys Glu Asp Ala Ala
            195                 200                 205

Tyr Asp Cys Phe Ile Phe Ser Asp Val Asp Leu Val Pro Met Asp Asp
    210                 215                 220

Arg Asn Leu Tyr Arg Cys Gly Asp Gln Pro Arg His Phe Ala Ile Ala
225                 230                 235                 240

Met Asp Lys Phe Gly Phe Arg Leu Pro Tyr Ala Gly Tyr Phe Gly Gly
            245                 250                 255

Val Ser Gly Leu Ser Lys Ala Gln Phe Leu Arg Ile Asn Gly Phe Pro
                260                 265                 270

Asn Glu Tyr Trp Gly Trp Gly Gly Glu Asp Asp Ile Phe Asn Arg
            275                 280                 285

Ile Ser Leu Thr Gly Met Lys Ile Ser Arg Pro Asp Ile Arg Ile Gly
    290                 295                 300

Arg Tyr Arg Met Ile Lys His Asp Arg Asp Lys His Asn Glu Pro Asn
305                 310                 315                 320

Pro Gln Arg Phe Thr Lys Ile Gln Asn Thr Lys Leu Thr Met Lys Arg
            325                 330                 335

Asp Gly Ile Gly Ser Val Arg Tyr Gln Val Leu Glu Val Ser Arg Gln
            340                 345                 350

Pro Leu Phe Thr Asn Ile Thr Val Asp Ile Gly Arg Pro Pro Ser Trp
            355                 360                 365

Pro Pro Arg Gly
        370

<210> SEQ ID NO 21
<211> LENGTH: 393
<212> TYPE: PRT
<213> ORGANISM: Homo sapiens

<400> SEQUENCE: 21

Met Leu Arg Arg Leu Leu Glu Arg Pro Cys Thr Leu Ala Leu Leu Val
1               5                   10                  15

Gly Ser Gln Leu Ala Val Met Met Tyr Leu Ser Leu Gly Gly Phe Arg
            20                  25                  30

Ser Leu Ser Ala Leu Phe Gly Arg Asp Gln Gly Pro Thr Phe Asp Tyr
        35                  40                  45

Ser His Pro Arg Asp Val Tyr Ser Asn Leu Ser His Leu Pro Gly Ala
    50                  55                  60

Pro Gly Gly Pro Pro Ala Pro Gln Gly Leu Pro Tyr Cys Pro Glu Arg
65                  70                  75                  80

Ser Pro Leu Leu Val Gly Pro Val Ser Val Ser Phe Ser Pro Val Pro
            85                  90                  95

Ser Leu Ala Glu Ile Val Glu Arg Asn Pro Arg Val Glu Pro Gly Gly
            100                 105                 110

Arg Tyr Arg Pro Ala Gly Cys Glu Pro Arg Ser Arg Thr Ala Ile Ile
            115                 120                 125

Val Pro His Arg Ala Arg Glu His Leu Arg Leu Leu Leu Tyr His
    130                 135                 140

Leu His Pro Phe Leu Gln Arg Gln Gln Leu Ala Tyr Gly Ile Tyr Val
145                 150                 155                 160

Ile His Gln Ala Gly Asn Gly Thr Phe Asn Arg Ala Lys Leu Leu Asn
            165                 170                 175

Val Gly Val Arg Glu Ala Leu Arg Asp Glu Glu Trp Asp Cys Leu Phe
```

```
                180                 185                 190
Leu His Asp Val Asp Leu Leu Pro Glu Asn Asp His Asn Leu Tyr Val
            195                 200                 205
Cys Asp Pro Arg Gly Pro Arg His Val Ala Val Ala Met Asn Lys Phe
210                 215                 220
Gly Tyr Ser Leu Pro Tyr Pro Gln Tyr Phe Gly Val Ser Ala Leu
225                 230                 235                 240
Thr Pro Asp Gln Tyr Leu Lys Met Asn Gly Phe Pro Asn Glu Tyr Trp
            245                 250                 255
Gly Trp Gly Gly Glu Asp Asp Ile Ala Thr Arg Val Arg Leu Ala
            260                 265                 270
Gly Met Lys Ile Ser Arg Pro Pro Thr Ser Val Gly His Tyr Lys Met
            275                 280                 285
Val Lys His Arg Gly Asp Lys Gly Asn Glu Glu Asn Pro His Arg Phe
            290                 295                 300
Asp Leu Leu Val Arg Thr Gln Asn Ser Trp Thr Gln Asp Gly Met Asn
305                 310                 315                 320
Ser Leu Thr Tyr Gln Leu Leu Ala Arg Glu Leu Gly Pro Leu Tyr Thr
            325                 330                 335
Asn Ile Thr Ala Asp Ile Gly Thr Asp Pro Arg Gly Pro Arg Ala Pro
            340                 345                 350
Ser Gly Pro Arg Tyr Pro Pro Gly Ser Ser Gln Ala Phe Arg Gln Glu
            355                 360                 365
Met Leu Gln Arg Arg Pro Pro Ala Arg Pro Gly Pro Leu Ser Thr Ala
            370                 375                 380
Asn His Thr Ala Leu Arg Gly Ser His
385                 390

<210> SEQ ID NO 22
<211> LENGTH: 344
<212> TYPE: PRT
<213> ORGANISM: Homo sapiens

<400> SEQUENCE: 22

Met Gly Phe Asn Leu Thr Phe His Leu Ser Tyr Lys Phe Arg Leu Leu
1               5                   10                  15
Leu Leu Leu Thr Leu Cys Leu Thr Val Val Gly Trp Ala Thr Ser Asn
            20                  25                  30
Tyr Phe Val Gly Ala Ile Gln Glu Ile Pro Lys Ala Lys Glu Phe Met
            35                  40                  45
Ala Asn Phe His Lys Thr Leu Ile Leu Gly Lys Gly Lys Thr Leu Thr
50                  55                  60
Asn Glu Ala Ser Thr Lys Lys Val Glu Leu Asp Asn Cys Pro Ser Val
65                  70                  75                  80
Ser Pro Tyr Leu Arg Gly Gln Ser Lys Leu Ile Phe Lys Pro Asp Leu
            85                  90                  95
Thr Leu Glu Glu Val Gln Ala Glu Asn Pro Lys Val Ser Arg Gly Arg
            100                 105                 110
Tyr Arg Pro Gln Glu Cys Lys Ala Leu Gln Arg Val Ala Ile Leu Val
            115                 120                 125
Pro His Arg Asn Arg Glu Lys His Leu Met Tyr Leu Leu Glu His Leu
            130                 135                 140
His Pro Phe Leu Gln Arg Gln Gln Leu Asp Tyr Gly Ile Tyr Val Ile
145                 150                 155                 160
```

```
His Gln Ala Glu Gly Lys Lys Phe Asn Arg Ala Lys Leu Leu Asn Val
            165                 170                 175

Gly Tyr Leu Glu Ala Leu Lys Glu Glu Asn Trp Asp Cys Phe Ile Phe
        180                 185                 190

His Asp Val Asp Leu Val Pro Glu Asn Asp Phe Asn Leu Tyr Lys Cys
            195                 200                 205

Glu Glu His Pro Lys His Leu Val Val Gly Arg Asn Ser Thr Gly Tyr
    210                 215                 220

Arg Leu Arg Tyr Ser Gly Tyr Phe Gly Gly Val Thr Ala Leu Ser Arg
225                 230                 235                 240

Glu Gln Phe Phe Lys Val Asn Gly Phe Ser Asn Asn Tyr Trp Gly Trp
                245                 250                 255

Gly Gly Glu Asp Asp Asp Leu Arg Leu Arg Val Glu Leu Gln Arg Met
            260                 265                 270

Lys Ile Ser Arg Pro Leu Pro Glu Val Gly Lys Tyr Thr Met Val Phe
        275                 280                 285

His Thr Arg Asp Lys Gly Asn Glu Val Asn Ala Glu Arg Met Lys Leu
    290                 295                 300

Leu His Gln Val Ser Arg Val Trp Arg Thr Asp Gly Leu Ser Ser Cys
305                 310                 315                 320

Ser Tyr Lys Leu Val Ser Val Glu His Asn Pro Leu Tyr Ile Asn Ile
                325                 330                 335

Thr Val Asp Phe Trp Phe Gly Ala
            340

<210> SEQ ID NO 23
<211> LENGTH: 388
<212> TYPE: PRT
<213> ORGANISM: Homo sapiens

<400> SEQUENCE: 23

Met Arg Ala Arg Arg Gly Leu Leu Arg Leu Pro Arg Arg Ser Leu Leu
1               5                   10                  15

Ala Ala Leu Phe Phe Phe Ser Leu Ser Ser Ser Leu Leu Tyr Phe Val
            20                  25                  30

Tyr Val Ala Pro Gly Ile Val Asn Thr Tyr Leu Phe Met Met Gln Ala
        35                  40                  45

Gln Gly Ile Leu Ile Arg Asp Asn Val Arg Thr Ile Gly Ala Gln Val
    50                  55                  60

Tyr Glu Gln Val Leu Arg Ser Ala Tyr Ala Lys Arg Asn Ser Ser Val
65                  70                  75                  80

Asn Asp Ser Asp Tyr Pro Leu Asp Leu Asn His Ser Glu Thr Phe Leu
                85                  90                  95

Gln Thr Thr Thr Phe Leu Pro Glu Asp Phe Thr Tyr Phe Ala Asn His
            100                 105                 110

Thr Cys Pro Glu Arg Leu Pro Ser Met Lys Gly Pro Ile Asp Ile Asn
        115                 120                 125

Met Ser Glu Ile Gly Met Asp Tyr Ile His Glu Leu Phe Ser Lys Asp
    130                 135                 140

Pro Thr Ile Lys Leu Gly Gly His Trp Lys Pro Ser Asp Cys Met Pro
145                 150                 155                 160

Arg Trp Lys Val Ala Ile Leu Ile Pro Phe Arg Asn Arg His Glu His
                165                 170                 175

Leu Pro Val Leu Phe Arg His Leu Leu Pro Met Leu Gln Arg Gln Arg
            180                 185                 190
```

Leu Gln Phe Ala Phe Tyr Val Glu Gln Val Gly Thr Gln Pro Phe
            195                 200                 205

Asn Arg Ala Met Leu Phe Asn Val Gly Phe Gln Glu Ala Met Lys Asp
210                 215                 220

Leu Asp Trp Asp Cys Leu Ile Phe His Asp Val Asp His Ile Pro Glu
225                 230                 235                 240

Ser Asp Arg Asn Tyr Tyr Gly Cys Gly Gln Met Pro Arg His Phe Ala
            245                 250                 255

Thr Lys Leu Asp Lys Tyr Met Tyr Leu Leu Pro Tyr Thr Glu Phe Phe
            260                 265                 270

Gly Gly Val Ser Gly Leu Thr Val Glu Gln Phe Arg Lys Ile Asn Gly
            275                 280                 285

Phe Pro Asn Ala Phe Trp Gly Trp Gly Gly Glu Asp Asp Asp Leu Trp
            290                 295                 300

Asn Arg Val Gln Asn Ala Gly Tyr Ser Val Ser Arg Pro Glu Gly Asp
305                 310                 315                 320

Thr Gly Lys Tyr Lys Ser Ile Pro His His Arg Gly Glu Val Gln
            325                 330                 335

Phe Leu Gly Arg Tyr Ala Leu Leu Arg Lys Ser Lys Glu Arg Gln Gly
            340                 345                 350

Leu Asp Gly Leu Asn Asn Leu Asn Tyr Phe Ala Asn Ile Thr Tyr Asp
            355                 360                 365

Ala Leu Tyr Lys Asn Ile Thr Val Asn Leu Thr Pro Glu Leu Ala Gln
            370                 375                 380

Val Asn Glu Tyr
385

<210> SEQ ID NO 24
<211> LENGTH: 382
<212> TYPE: PRT
<213> ORGANISM: Homo sapiens

<400> SEQUENCE: 24

Met Ser Val Leu Arg Arg Met Met Arg Val Ser Asn Arg Ser Leu Leu
1               5                   10                  15

Ala Phe Ile Phe Phe Ser Leu Ser Ser Ser Cys Leu Tyr Phe Ile
            20                  25                  30

Tyr Val Ala Pro Gly Ile Ala Asn Thr Tyr Leu Phe Met Val Gln Ala
            35                  40                  45

Arg Gly Ile Met Leu Arg Glu Asn Val Lys Thr Ile Gly His Met Ile
50                  55                  60

Arg Leu Tyr Thr Asn Lys Asn Ser Thr Leu Asn Gly Thr Asp Tyr Pro
65                  70                  75                  80

Glu Gly Asn Asn Ser Ser Asp Tyr Leu Val Gln Thr Thr Thr Tyr Leu
            85                  90                  95

Pro Glu Asn Phe Thr Tyr Ser Pro Tyr Leu Pro Cys Pro Glu Lys Leu
            100                 105                 110

Pro Tyr Met Arg Gly Phe Leu Asn Val Asn Val Ser Glu Val Ser Phe
            115                 120                 125

Asp Glu Ile His Gln Leu Phe Ser Lys Asp Leu Asp Ile Glu Pro Gly
            130                 135                 140

Gly His Trp Arg Pro Lys Asp Cys Lys Pro Arg Trp Lys Val Ala Val
145                 150                 155                 160

Leu Ile Pro Phe Arg Asn Arg His Glu His Leu Pro Ile Phe Phe Leu

His Leu Ile Pro Met Leu Gln Lys Gln Arg Leu Glu Phe Ala Phe Tyr
            165                 170                 175

Val Ile Glu Gln Thr Gly Thr Gln Pro Phe Asn Arg Ala Met Leu Phe
        180                 185                 190

Asn Val Gly Phe Lys Glu Ala Met Lys Asp Ser Val Trp Asp Cys Val
    210                 215                 220

Ile Phe His Asp Val Asp His Leu Pro Glu Asn Asp Arg Asn Tyr Tyr
225                 230                 235                 240

Gly Cys Gly Glu Met Pro Arg His Phe Ala Ala Lys Leu Asp Lys Tyr
                245                 250                 255

Met Tyr Ile Leu Pro Tyr Lys Glu Phe Phe Gly Gly Val Ser Gly Leu
            260                 265                 270

Thr Val Glu Gln Phe Arg Lys Ile Asn Gly Phe Pro Asn Ala Phe Trp
        275                 280                 285

Gly Trp Gly Gly Glu Asp Asp Asp Leu Trp Asn Arg Val His Tyr Ala
    290                 295                 300

Gly Tyr Asn Val Thr Arg Pro Glu Gly Asp Leu Gly Lys Tyr Lys Ser
305                 310                 315                 320

Ile Pro His His His Arg Gly Glu Val Gln Phe Leu Gly Arg Tyr Lys
                325                 330                 335

Leu Leu Arg Tyr Ser Lys Glu Arg Gln Tyr Ile Asp Gly Leu Asn Asn
            340                 345                 350

Leu Ile Tyr Arg Pro Lys Ile Leu Val Asp Arg Leu Tyr Thr Asn Ile
        355                 360                 365

Ser Val Asn Leu Met Pro Glu Leu Ala Pro Ile Glu Asp Tyr
    370                 375                 380

<210> SEQ ID NO 25
<211> LENGTH: 327
<212> TYPE: PRT
<213> ORGANISM: Homo sapiens

<400> SEQUENCE: 25

Met Phe Pro Ser Arg Arg Lys Ala Ala Gln Leu Pro Trp Glu Asp Gly
1               5                   10                  15

Arg Ser Gly Leu Leu Ser Gly Gly Leu Pro Arg Lys Cys Ser Val Phe
            20                  25                  30

His Leu Phe Val Ala Cys Leu Ser Leu Gly Phe Phe Ser Leu Leu Trp
        35                  40                  45

Leu Gln Leu Ser Cys Ser Gly Asp Val Ala Arg Ala Val Arg Gly Gln
    50                  55                  60

Gly Gln Glu Thr Ser Gly Pro Pro Arg Ala Cys Pro Pro Glu Pro Pro
65                  70                  75                  80

Pro Glu His Trp Glu Glu Asp Ala Ser Trp Gly Pro His Arg Leu Ala
                85                  90                  95

Val Leu Val Pro Phe Arg Glu Arg Phe Glu Glu Leu Leu Val Phe Val
            100                 105                 110

Pro His Met Arg Arg Phe Leu Ser Arg Lys Lys Ile Arg His His Ile
        115                 120                 125

Tyr Val Leu Asn Gln Val Asp His Phe Arg Phe Asn Arg Ala Ala Leu
    130                 135                 140

Ile Asn Val Gly Phe Leu Glu Ser Ser Asn Ser Thr Asp Tyr Ile Ala
145                 150                 155                 160

```
Met His Asp Val Asp Leu Leu Pro Leu Asn Glu Glu Leu Asp Tyr Gly
                165                 170                 175
Phe Pro Glu Ala Gly Pro Phe His Val Ala Ser Pro Glu Leu His Pro
            180                 185                 190
Leu Tyr His Tyr Lys Thr Tyr Val Gly Gly Ile Leu Leu Leu Ser Lys
        195                 200                 205
Gln His Tyr Arg Leu Cys Asn Gly Met Ser Asn Arg Phe Trp Gly Trp
    210                 215                 220
Gly Arg Glu Asp Asp Glu Phe Tyr Arg Arg Ile Lys Gly Ala Gly Leu
225                 230                 235                 240
Gln Leu Phe Arg Pro Ser Gly Ile Thr Thr Gly Tyr Lys Thr Phe Arg
                245                 250                 255
His Leu His Asp Pro Ala Trp Arg Lys Arg Asp Gln Lys Arg Ile Ala
            260                 265                 270
Ala Gln Lys Gln Glu Gln Phe Lys Val Asp Arg Glu Gly Gly Leu Asn
        275                 280                 285
Thr Val Lys Tyr His Val Ala Ser Arg Thr Ala Leu Ser Val Gly Gly
    290                 295                 300
Ala Pro Cys Thr Val Leu Asn Ile Met Leu Asp Cys Asp Lys Thr Ala
305                 310                 315                 320
Thr Pro Trp Cys Thr Phe Ser
                325

<210> SEQ ID NO 26
<211> LENGTH: 332
<212> TYPE: PRT
<213> ORGANISM: Streptococcus thermophilus

<400> SEQUENCE: 26

Met Ala Ile Leu Val Leu Gly Gly Ala Gly Tyr Ile Gly Ser His Met
1               5                   10                  15
Val Asp Arg Leu Val Glu Lys Gly Gln Glu Lys Val Val Val Val Asp
            20                  25                  30
Ser Leu Val Thr Gly His Arg Ala Ala Val His Pro Asp Ala Ile Phe
        35                  40                  45
Tyr Gln Gly Asp Leu Ser Asp Gln Asp Phe Met Arg Lys Val Phe Lys
    50                  55                  60
Glu Asn Pro Asp Val Asp Ala Val Ile His Phe Ala Ala Tyr Ser Leu
65                  70                  75                  80
Val Gly Glu Ser Met Glu Lys Pro Leu Lys Tyr Phe Asp Asn Asn Thr
                85                  90                  95
Ala Gly Met Val Lys Leu Leu Glu Val Met Asn Glu Cys Gly Val Lys
            100                 105                 110
Tyr Ile Val Phe Ser Ser Thr Ala Ala Thr Tyr Gly Ile Pro Glu Glu
        115                 120                 125
Ile Pro Ile Leu Glu Thr Thr Pro Gln Asn Pro Ile Asn Pro Tyr Gly
    130                 135                 140
Glu Ser Lys Leu Met Met Glu Thr Ile Met Lys Trp Ser Asp Gln Ala
145                 150                 155                 160
Tyr Gly Ile Lys Tyr Val Pro Leu Arg Tyr Phe Asn Val Ala Gly Ala
                165                 170                 175
Asn Leu Met Val Arg Leu Val Arg Thr Arg Ser Glu Thr His Leu Leu
            180                 185                 190
Pro Ile Ile Leu Gln Val Ala Gln Gly Val Arg Glu Lys Ile Met Ile
        195                 200                 205
```

```
Phe Gly Asp Asp Tyr Asn Thr Pro Asp Gly Thr Asn Val Arg Asp Tyr
        210                 215                 220

Val His Pro Phe Asp Leu Ala Asp Ala His Leu Leu Ala Val Glu Tyr
225                 230                 235                 240

Leu Arg Lys Gly Asn Glu Ser Thr Ala Phe Asn Leu Gly Ser Ser Thr
                245                 250                 255

Gly Phe Ser Asn Leu Gln Ile Leu Glu Ala Ala Arg Lys Val Thr Gly
                260                 265                 270

Lys Glu Ile Pro Ala Glu Lys Ala Asp Arg Arg Pro Gly Asp Pro Asp
            275                 280                 285

Ile Leu Ile Ala Ser Ser Glu Lys Ala Arg Thr Val Leu Gly Trp Lys
        290                 295                 300

Pro Gln Phe Asp Asn Ile Glu Lys Ile Ile Ala Ser Ala Trp Ala Trp
305                 310                 315                 320

His Ser Ser His Pro Lys Gly Tyr Asp Asp Arg Gly
                325                 330

<210> SEQ ID NO 27
<211> LENGTH: 348
<212> TYPE: PRT
<213> ORGANISM: Homo sapiens

<400> SEQUENCE: 27

Met Ala Glu Lys Val Leu Val Thr Gly Gly Ala Gly Tyr Ile Gly Ser
1               5                   10                  15

His Thr Val Leu Glu Leu Leu Glu Ala Gly Tyr Leu Pro Val Val Ile
                20                  25                  30

Asp Asn Phe His Asn Ala Phe Arg Gly Gly Gly Ser Leu Pro Glu Ser
            35                  40                  45

Leu Arg Arg Val Gln Glu Leu Thr Gly Arg Ser Val Glu Phe Glu Glu
        50                  55                  60

Met Asp Ile Leu Asp Gln Gly Ala Leu Gln Arg Leu Phe Lys Lys Tyr
65                  70                  75                  80

Ser Phe Met Ala Val Ile His Phe Ala Gly Leu Lys Ala Val Gly Glu
                85                  90                  95

Ser Val Gln Lys Pro Leu Asp Tyr Tyr Arg Val Asn Leu Thr Gly Thr
                100                 105                 110

Ile Gln Leu Leu Glu Ile Met Lys Ala His Gly Val Lys Asn Leu Val
            115                 120                 125

Phe Ser Ser Ser Ala Thr Val Tyr Gly Asn Pro Gln Tyr Leu Pro Leu
        130                 135                 140

Asp Glu Ala His Pro Thr Gly Gly Cys Thr Asn Pro Tyr Gly Lys Ser
145                 150                 155                 160

Lys Phe Phe Ile Glu Glu Met Ile Arg Asp Leu Cys Gln Ala Asp Lys
                165                 170                 175

Thr Trp Asn Ala Val Leu Leu Arg Tyr Phe Asn Pro Thr Gly Ala His
                180                 185                 190

Ala Ser Gly Cys Ile Gly Glu Asp Pro Gln Gly Ile Pro Asn Asn Leu
            195                 200                 205

Met Pro Tyr Val Ser Gln Val Ala Ile Gly Arg Arg Glu Ala Leu Asn
        210                 215                 220

Val Phe Gly Asn Asp Tyr Asp Thr Glu Asp Gly Thr Gly Val Arg Asp
225                 230                 235                 240

Tyr Ile His Val Val Asp Leu Ala Lys Gly His Ile Ala Ala Leu Arg
```

```
                      245                 250                 255
Lys Leu Lys Glu Gln Cys Gly Cys Arg Ile Tyr Asn Leu Gly Thr Gly
            260                 265                 270

Thr Gly Tyr Ser Val Leu Gln Met Val Gln Ala Met Glu Lys Ala Ser
        275                 280                 285

Gly Lys Lys Ile Pro Tyr Lys Val Val Ala Arg Arg Glu Gly Asp Val
    290                 295                 300

Ala Ala Cys Tyr Ala Asn Pro Ser Leu Ala Gln Glu Glu Leu Gly Trp
305                 310                 315                 320

Thr Ala Ala Leu Gly Leu Asp Arg Met Cys Glu Asp Leu Trp Arg Trp
            325                 330                 335

Gln Lys Gln Asn Pro Ser Gly Phe Gly Thr Gln Ala
            340                 345

<210> SEQ ID NO 28
<211> LENGTH: 338
<212> TYPE: PRT
<213> ORGANISM: Escherichia coli

<400> SEQUENCE: 28

Met Arg Val Leu Val Thr Gly Gly Ser Gly Tyr Ile Gly Ser His Thr
1               5                   10                  15

Cys Val Gln Leu Leu Gln Asn Gly His Asp Val Ile Ile Leu Asp Asn
            20                  25                  30

Leu Cys Asn Ser Lys Arg Ser Val Leu Pro Val Ile Glu Arg Leu Gly
        35                  40                  45

Gly Lys His Pro Thr Phe Val Glu Gly Asp Ile Arg Asn Glu Ala Leu
    50                  55                  60

Met Thr Glu Ile Leu His Asp His Ala Ile Asp Thr Val Ile His Phe
65                  70                  75                  80

Ala Gly Leu Lys Ala Val Gly Glu Ser Val Gln Lys Pro Leu Glu Tyr
                85                  90                  95

Tyr Asp Asn Asn Val Asn Gly Thr Leu Arg Leu Ile Ser Ala Met Arg
            100                 105                 110

Ala Ala Asn Val Lys Asn Phe Ile Phe Ser Ser Ser Ala Thr Val Tyr
        115                 120                 125

Gly Asp Gln Pro Lys Ile Pro Tyr Val Glu Ser Phe Pro Thr Gly Thr
    130                 135                 140

Pro Gln Ser Pro Tyr Gly Lys Ser Lys Leu Met Val Glu Gln Ile Leu
145                 150                 155                 160

Thr Asp Leu Gln Lys Ala Gln Pro Asp Trp Ser Ile Ala Leu Leu Arg
                165                 170                 175

Tyr Phe Asn Pro Val Gly Ala His Pro Ser Gly Asp Met Gly Glu Asp
            180                 185                 190

Pro Gln Gly Ile Pro Asn Asn Leu Met Pro Tyr Ile Ala Gln Val Ala
        195                 200                 205

Val Gly Arg Arg Asp Ser Leu Ala Ile Phe Gly Asn Asp Tyr Pro Thr
    210                 215                 220

Glu Asp Gly Thr Gly Val Arg Asp Tyr Ile His Val Met Asp Leu Ala
225                 230                 235                 240

Asp Gly His Val Val Ala Met Glu Lys Leu Ala Asn Lys Pro Gly Val
                245                 250                 255

His Ile Tyr Asn Leu Gly Ala Gly Val Gly Asn Ser Val Leu Asp Val
            260                 265                 270
```

```
Val Asn Ala Phe Ser Lys Ala Cys Gly Lys Pro Val Asn Tyr His Phe
            275                 280                 285

Ala Pro Arg Arg Glu Gly Asp Leu Pro Ala Tyr Trp Ala Asp Ala Ser
290                 295                 300

Lys Ala Asp Arg Glu Leu Asn Trp Arg Val Thr Arg Thr Leu Asp Glu
305                 310                 315                 320

Met Ala Gln Asp Thr Trp His Trp Gln Ser Arg His Pro Gln Gly Tyr
                325                 330                 335

Pro Asp

<210> SEQ ID NO 29
<211> LENGTH: 338
<212> TYPE: PRT
<213> ORGANISM: Haemophilus influenzae

<400> SEQUENCE: 29

Met Ala Ile Leu Val Thr Gly Gly Ala Gly Tyr Ile Gly Ser His Thr
1               5                   10                  15

Val Val Glu Leu Leu Asn Val Gly Lys Glu Val Val Leu Asp Asn
            20                  25                  30

Leu Cys Asn Ser Ser Pro Lys Ser Leu Glu Arg Val Lys Gln Ile Thr
            35                  40                  45

Gly Lys Glu Ala Lys Phe Tyr Glu Gly Asp Ile Leu Asp Arg Ala Leu
50                  55                  60

Leu Gln Lys Ile Phe Ala Glu Asn Glu Ile Asn Ser Val Ile His Phe
65                  70                  75                  80

Ala Gly Leu Lys Ala Val Gly Glu Ser Val Gln Lys Pro Thr Glu Tyr
                85                  90                  95

Tyr Met Asn Asn Val Ala Gly Thr Leu Val Leu Ile Gln Glu Met Lys
            100                 105                 110

Lys Ala Gly Val Trp Asn Phe Val Phe Ser Ser Ala Thr Val Tyr
            115                 120                 125

Gly Asp Pro Lys Ile Ile Pro Ile Thr Glu Asp Cys Glu Val Gly Gly
130                 135                 140

Thr Thr Asn Pro Tyr Gly Thr Ser Lys Tyr Met Val Glu Gln Ile Leu
145                 150                 155                 160

Arg Asp Thr Ala Lys Ala Glu Pro Lys Phe Ser Met Thr Ile Leu Arg
                165                 170                 175

Tyr Phe Asn Pro Val Gly Ala His Glu Ser Gly Leu Ile Gly Glu Asp
            180                 185                 190

Pro Asn Gly Ile Pro Asn Asn Leu Leu Pro Tyr Ile Ser Gln Val Ala
            195                 200                 205

Ile Gly Lys Leu Ala Gln Leu Ser Val Phe Gly Ser Asp Tyr Asp Thr
210                 215                 220

His Asp Gly Thr Gly Val Arg Asp Tyr Ile His Val Val Asp Leu Ala
225                 230                 235                 240

Val Gly His Leu Lys Ala Leu Gln Arg His Glu Asn Asp Ala Gly Leu
                245                 250                 255

His Ile Tyr Asn Leu Gly Thr Gly His Gly Tyr Ser Val Leu Asp Met
            260                 265                 270

Val Lys Ala Phe Glu Lys Ala Asn Asn Ile Thr Ile Ala Tyr Lys Leu
275                 280                 285

Val Glu Arg Arg Ser Gly Asp Ile Ala Thr Cys Tyr Ser Asp Pro Ser
290                 295                 300
```

Leu Ala Ala Lys Glu Leu Gly Trp Val Ala Glu Arg Gly Leu Glu Lys
305                 310                 315                 320

Met Met Gln Asp Thr Trp Asn Trp Gln Lys Asn Asn Pro Lys Gly Tyr
                325                 330                 335

Arg Asp

<210> SEQ ID NO 30
<211> LENGTH: 339
<212> TYPE: PRT
<213> ORGANISM: Neisseria meningitides

<400> SEQUENCE: 30

Met Lys Lys Ile Leu Val Thr Gly Gly Thr Gly Phe Ile Gly Ser His
1               5                   10                  15

Thr Val Val Ser Leu Leu Lys Ser Gly His Gln Val Val Ile Leu Asp
                20                  25                  30

Asn Leu Cys Asn Ser Ser Ile Asn Ile Leu Pro Arg Leu Lys Thr Ile
            35                  40                  45

Thr Gly Gln Glu Ile Pro Phe Tyr Gln Gly Asp Ile Arg Asp Arg Glu
50                  55                  60

Ile Leu Arg Arg Ile Phe Ala Glu Asn Arg Ile Asp Ser Val Ile His
65                  70                  75                  80

Phe Ala Gly Leu Lys Ala Val Gly Glu Ser Val Ala Glu Pro Met Lys
                85                  90                  95

Tyr Tyr Asp Asn Asn Val Ser Gly Ser Leu Val Leu Ala Glu Glu Met
            100                 105                 110

Ala Arg Ala Gly Val Phe Ser Ile Val Phe Ser Ser Ser Ala Thr Val
        115                 120                 125

Tyr Gly Asp Pro Gly Lys Val Pro Tyr Thr Glu Asp Met Pro Pro Gly
130                 135                 140

Asp Thr Thr Ser Pro Tyr Gly Ala Ser Lys Ser Met Val Glu Arg Ile
145                 150                 155                 160

Leu Thr Asp Ile Gln Lys Ala Asp Pro Arg Trp Ser Met Ile Leu Leu
                165                 170                 175

Arg Tyr Phe Asn Pro Ile Gly Ala His Glu Ser Gly Leu Ile Gly Glu
            180                 185                 190

Gln Pro Asn Gly Ile Pro Asn Asn Leu Leu Pro Tyr Ile Cys Gln Val
        195                 200                 205

Ala Ala Gly Lys Leu Pro Gln Leu Ala Val Phe Gly Asp Asp Tyr Pro
210                 215                 220

Thr Pro Asp Gly Thr Gly Met Arg Asp Tyr Ile His Val Met Asp Leu
225                 230                 235                 240

Ala Glu Gly His Val Ala Ala Met Gln Ala Lys Ser Asn Val Ala Gly
                245                 250                 255

Thr His Leu Leu Asn Leu Gly Ser Gly Arg Ala Ser Ser Val Leu Glu
            260                 265                 270

Ile Ile Arg Ala Phe Glu Ala Ala Ser Gly Leu Thr Ile Pro Tyr Glu
        275                 280                 285

Val Lys Pro Arg Arg Ala Gly Asp Leu Ala Cys Phe Tyr Ala Asp Pro
290                 295                 300

Ser Tyr Thr Lys Ala Gln Ile Gly Trp Gln Thr Gln Arg Asp Leu Thr
305                 310                 315                 320

Gln Met Met Glu Asp Ser Trp Arg Trp Val Ser Asn Asn Pro Asn Gly
                325                 330                 335

Tyr Asp Asp

<210> SEQ ID NO 31
<211> LENGTH: 395
<212> TYPE: PRT
<213> ORGANISM: Trypanosoma brucei

<400> SEQUENCE: 31

Met Arg Val Leu Val Cys Gly Ala Gly Tyr Ile Gly Ser His Phe
1               5                   10                  15

Val Arg Ala Leu Leu Arg Asp Thr Asn His Ser Val Val Ile Val Asp
            20                  25                  30

Ser Leu Gly Thr His Gly Lys Ser Asp His Val Glu Thr Arg Glu
        35                  40                  45

Asn Val Ala Arg Lys Leu Gln Gln Ser Asp Gly Pro Lys Pro Pro Trp
50                  55                  60

Ala Asp Arg Tyr Ala Ala Leu Glu Val Gly Asp Val Arg Asn Glu Asp
65                  70                  75                  80

Phe Leu Asn Gly Val Phe Thr Arg His Gly Pro Ile Asp Ala Val Val
                85                  90                  95

His Met Cys Ala Phe Leu Ala Val Gly Glu Ser Val Arg Asp Pro Leu
            100                 105                 110

Lys Tyr Tyr Asp Asn Asn Val Val Gly Ile Leu Arg Leu Leu Gln Ala
        115                 120                 125

Met Leu Leu His Lys Cys Asp Lys Ile Ile Phe Ser Ser Ser Ala Ala
130                 135                 140

Ile Phe Gly Asn Pro Thr Met Gly Ser Val Ser Thr Asn Ala Glu Pro
145                 150                 155                 160

Ile Asp Ile Asn Ala Lys Lys Ser Pro Glu Ser Pro Tyr Gly Glu Ser
                165                 170                 175

Lys Leu Ile Ala Glu Arg Met Ile Arg Asp Cys Ala Glu Ala Tyr Gly
            180                 185                 190

Ile Lys Gly Ile Cys Leu Arg Tyr Phe Asn Ala Cys Gly Ala His Glu
        195                 200                 205

Asp Gly Asp Ile Gly Glu His Tyr Gln Gly Ser Thr His Leu Ile Pro
210                 215                 220

Ile Ile Leu Gly Arg Val Met Ser Asp Ile Ala Pro Asp Gln Arg Leu
225                 230                 235                 240

Thr Ile His Glu Asp Ala Ser Thr Asp Lys Arg Met Pro Ile Phe Gly
                245                 250                 255

Thr Asp Tyr Pro Thr Pro Asp Gly Thr Cys Val Arg Asp Tyr Val His
            260                 265                 270

Val Cys Asp Leu Ala Ser Ala His Ile Leu Ala Leu Asp Tyr Val Glu
        275                 280                 285

Lys Leu Gly Pro Asn Asp Lys Ser Lys Tyr Phe Ser Val Phe Asn Leu
290                 295                 300

Gly Thr Ser Arg Gly Tyr Ser Val Arg Glu Val Ile Glu Val Ala Arg
305                 310                 315                 320

Lys Thr Thr Gly His Pro Ile Pro Val Arg Glu Cys Gly Arg Arg Glu
                325                 330                 335

Gly Asp Pro Ala Tyr Leu Val Ala Ala Ser Asp Lys Ala Arg Glu Val
            340                 345                 350

Leu Gly Trp Lys Pro Lys Tyr Asp Thr Leu Glu Ala Ile Met Glu Thr
        355                 360                 365

Ser Trp Lys Phe Gln Arg Thr His Pro Asn Gly Tyr Ala Ser Gln Glu
370                 375                 380

Asn Gly Thr Pro Gly Gly Arg Thr Thr Lys Leu
385                 390                 395

<210> SEQ ID NO 32
<211> LENGTH: 367
<212> TYPE: PRT
<213> ORGANISM: Escherichia coli

<400> SEQUENCE: 32

Met Tyr Asp Tyr Ile Ile Val Gly Ser Gly Leu Phe Gly Ala Val Cys
1               5                   10                  15

Ala Asn Glu Leu Lys Lys Leu Asn Lys Lys Val Leu Val Ile Glu Lys
            20                  25                  30

Arg Asn His Ile Gly Gly Asn Ala Tyr Thr Glu Asp Cys Glu Gly Ile
        35                  40                  45

Gln Ile His Lys Tyr Gly Ala His Ile Phe His Thr Asn Asp Lys Tyr
    50                  55                  60

Ile Trp Asp Tyr Val Asn Asp Leu Val Glu Phe Asn Arg Phe Thr Asn
65                  70                  75                  80

Ser Pro Leu Ala Ile Tyr Lys Asp Lys Leu Phe Asn Leu Pro Phe Asn
                85                  90                  95

Met Asn Thr Phe His Gln Met Trp Gly Val Lys Asp Pro Gln Glu Ala
            100                 105                 110

Gln Asn Ile Ile Asn Ala Gln Lys Lys Tyr Gly Asp Lys Val Pro
        115                 120                 125

Glu Asn Leu Glu Glu Gln Ala Ile Ser Leu Val Gly Glu Asp Leu Tyr
    130                 135                 140

Gln Ala Leu Ile Lys Gly Tyr Thr Glu Lys Gln Trp Gly Arg Ser Ala
145                 150                 155                 160

Lys Glu Leu Pro Ala Phe Ile Ile Lys Arg Ile Pro Val Arg Phe Thr
                165                 170                 175

Phe Asp Asn Asn Tyr Phe Ser Asp Arg Tyr Gln Gly Ile Pro Val Gly
            180                 185                 190

Gly Tyr Thr Lys Leu Ile Glu Lys Met Leu Glu Gly Val Asp Val Lys
        195                 200                 205

Leu Gly Ile Asp Phe Leu Lys Asp Lys Asp Ser Leu Ala Ser Lys Ala
    210                 215                 220

His Arg Ile Ile Tyr Thr Gly Pro Ile Asp Gln Tyr Phe Asp Tyr Arg
225                 230                 235                 240

Phe Gly Ala Leu Glu Tyr Arg Ser Leu Lys Phe Glu Thr Glu Arg His
                245                 250                 255

Glu Phe Pro Asn Phe Gln Gly Asn Ala Val Ile Asn Phe Thr Asp Ala
            260                 265                 270

Asn Val Pro Tyr Thr Arg Ile Ile Glu His Lys His Phe Asp Tyr Val
        275                 280                 285

Glu Thr Lys His Thr Val Val Thr Lys Glu Tyr Pro Leu Glu Trp Lys
    290                 295                 300

Val Gly Asp Glu Pro Tyr Tyr Pro Val Asn Asp Asn Lys Asn Met Glu
305                 310                 315                 320

Leu Phe Lys Lys Tyr Arg Glu Leu Ala Ser Arg Glu Asp Lys Val Ile
                325                 330                 335

Phe Gly Gly Arg Leu Ala Glu Tyr Lys Tyr Tyr Asp Met His Gln Val
            340                 345                 350

```
Ile Ser Ala Ala Leu Tyr Gln Val Lys Asn Ile Met Ser Thr Asp
        355                 360                 365
```

<210> SEQ ID NO 33
<211> LENGTH: 404
<212> TYPE: PRT
<213> ORGANISM: Mycoplasma genitalium

<400> SEQUENCE: 33

```
Met Asn Val Ile Leu Ser Val Met Leu Phe Ser Ser Pro Ser Cys Val
1               5                   10                  15

Asn Ile Asn Ser Phe Asp Ile Leu Ile Val Gly Ala Gly Ile Ser Gly
            20                  25                  30

Ile Val Leu Ala Asn Ile Leu Ala Asn His Asn Lys Arg Val Leu Ile
        35                  40                  45

Val Glu Lys Arg Asp His Ile Gly Gly Asn Cys Tyr Asp Lys Val Asp
    50                  55                  60

Ser Lys Thr Gln Leu Leu Phe His Gln Tyr Gly Pro His Ile Phe His
65                  70                  75                  80

Thr Asn Asn Gln Thr Val Ile Asn Phe Ile Ser Pro Phe Phe Glu Leu
                85                  90                  95

Asn Asn Tyr His His Arg Val Gly Leu Lys Leu Lys Asn Asn Leu Asp
            100                 105                 110

Leu Thr Leu Pro Phe Asp Phe Gln Gln Ile Tyr Lys Leu Met Gly Lys
        115                 120                 125

Asp Gly Arg Lys Leu Val Ser Phe Phe Lys Glu Asn Phe Ser Leu Asn
    130                 135                 140

Thr His Leu Ser Leu Ala Glu Leu Gln Leu Ile Asp Asn Pro Leu Ala
145                 150                 155                 160

Gln Lys Leu Tyr Gln Phe Leu Ile Ser Asn Val Tyr Lys Pro Tyr Ser
                165                 170                 175

Val Lys Met Trp Gly Leu Pro Phe Ala Met Ile Asn Glu Asn Val Ile
            180                 185                 190

Asn Arg Val Lys Ile Val Leu Ser Glu Gln Ser Ser Tyr Phe Pro Asp
        195                 200                 205

Ala Ile Ile Gln Gly Leu Pro Lys Ser Gly Tyr Thr Asn Ser Phe Leu
    210                 215                 220

Lys Met Leu Ala Asn Pro Leu Ile Asp Val Gln Leu Asn Cys Lys Asp
225                 230                 235                 240

Asn Leu Leu Val Tyr Gln Asp Glu Lys Leu Phe Phe Asn Asn Asn Leu
                245                 250                 255

Ile Glu Lys Pro Val Val Tyr Cys Gly Leu Ile Asp Lys Leu Phe Asn
            260                 265                 270

Phe Cys Phe Gly His Leu Gln Tyr Arg Ser Leu Ala Phe Ser Trp Lys
        275                 280                 285

Arg Phe Asn Gln Lys Tyr Gln Thr Tyr Pro Val Val Asn Met Pro
    290                 295                 300

Leu Ala Lys Ser Ile Thr Arg Ser Val Glu Tyr Lys Gln Leu Thr Asn
305                 310                 315                 320

Gln Gly Ser Phe Lys Pro Gln Thr Ile Val Ser Phe Glu Thr Pro Gly
                325                 330                 335

Ser Tyr Ala Ile Asn Asp Pro Arg Phe Asn Glu Pro Tyr Tyr Pro Ile
            340                 345                 350

Asn Asn Thr Leu Asn Asp Thr Leu Phe Lys Lys Tyr Trp Lys Lys Ala
```

```
        355                 360                 365
Ser Lys Leu Lys Asn Leu His Leu Leu Gly Arg Leu Ala Thr Tyr Gln
    370                 375                 380

Tyr Ile Asp Met Asp Lys Ala Ile Leu Leu Ser Ile Lys Lys Ala Gln
385                 390                 395                 400

Gln Leu Leu Ser
```